(12) United States Patent
Frost et al.

(10) Patent No.: US 8,470,792 B2
(45) Date of Patent: Jun. 25, 2013

(54) COMPOSITIONS AND METHODS FOR SELECTIVE INHIBITION OF VEGF

(75) Inventors: Phillip Frost, Miami Beach, FL (US); Nadine Dejneka, Wynnewood, PA (US); Ottrina S. Bond, Aventura, FL (US); Naveed Shams, Danville, CA (US)

(73) Assignee: Opko Pharmaceuticals, LLC., Miami, FL (US)

( * ) Notice: Subject to any disclaimer, the term of this patent is extended or adjusted under 35 U.S.C. 154(b) by 0 days.

(21) Appl. No.: 12/631,078

(22) Filed: Dec. 4, 2009

(65) Prior Publication Data

US 2010/0151007 A1    Jun. 17, 2010

Related U.S. Application Data

(60) Provisional application No. 61/119,779, filed on Dec. 4, 2008, provisional application No. 61/171,571, filed on Apr. 22, 2009, provisional application No. 61/219,808, filed on Jun. 24, 2009.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search
USPC ............................. 536/23.1, 24.3, 24.33, 24.5
See application file for complete search history.

(56) References Cited

U.S. PATENT DOCUMENTS

| | | |
|---|---|---|
| 4,235,871 A | 11/1980 | Papahadjopoulos et al. |
| 4,394,448 A | 7/1983 | Szoka, Jr. et al. |
| 4,501,728 A | 2/1985 | Geho et al. |
| 4,670,388 A | 6/1987 | Rubin et al. |
| 4,837,028 A | 6/1989 | Allen |
| 4,920,016 A | 4/1990 | Allen et al. |
| 5,019,369 A | 5/1991 | Presant et al. |
| 5,139,941 A | 8/1992 | Muzyczka et al. |
| 5,252,479 A | 10/1993 | Srivastava |
| 5,322,933 A | 6/1994 | Davies et al. |
| 5,498,521 A | 3/1996 | Dryja et al. |

(Continued)

FOREIGN PATENT DOCUMENTS

| | | |
|---|---|---|
| CA | 2359180 A1 | 8/2000 |
| EP | 0308066 A2 | 3/1989 |

(Continued)

OTHER PUBLICATIONS

Reich et al. (Retina, 2004 vol. 24:132-138, made of record on Applicant's Information Disclosure Statement filed Jun. 8, 2010).*

(Continued)

*Primary Examiner* — Terra Cotta Gibbs
(74) *Attorney, Agent, or Firm* — Pepper Hamilton LLP

(57) ABSTRACT

Disclosed herein are siRNA compositions and methods useful for inhibiting expression of vascular endothelial growth factor (VEGF) isoforms. Such compositions and methods further involve siRNA capable of selectively targeting angiogenic VEGF isoforms while selectively sparing anti-angiogenic isoforms. Diseases which involve angiogenesis stimulated by overexpression of VEGF, such as diabetic retinopathy, age related macular degeneration and many types of cancer, can be treated by administering small interfering RNAs as disclosed.

58 Claims, 40 Drawing Sheets

U.S. PATENT DOCUMENTS

| | | | |
|---|---|---|---|
| 5,550,289 A | 8/1996 | Eppstein et al. |
| 5,580,859 A | 12/1996 | Felgner et al. |
| 5,588,961 A | 12/1996 | Leone et al. |
| 5,589,466 A | 12/1996 | Felgner et al. |
| 5,624,803 A | 4/1997 | Noonberg et al. |
| 5,639,736 A | 6/1997 | Robinson |
| 5,639,872 A | 6/1997 | Robinson |
| 5,661,135 A | 8/1997 | Robinson |
| 5,683,986 A | 11/1997 | Carter |
| 5,712,257 A | 1/1998 | Carter |
| 5,728,068 A | 3/1998 | Leone et al. |
| 5,801,156 A | 9/1998 | Robinson et al. |
| 5,814,620 A | 9/1998 | Robinson et al. |
| 5,843,016 A | 12/1998 | Lugnani et al. |
| 5,902,598 A | 5/1999 | Chen et al. |
| 6,015,894 A | 1/2000 | Bennett et al. |
| 6,020,462 A | 2/2000 | Semenza |
| 6,037,329 A | 3/2000 | Baird et al. |
| 6,121,000 A | 9/2000 | Wright et al. |
| 6,150,092 A | 11/2000 | Uchida et al. |
| 6,165,709 A | 12/2000 | Friend et al. |
| 6,177,401 B1 | 1/2001 | Ullrigh et al. |
| 6,219,557 B1 | 4/2001 | Havinis |
| 6,331,313 B1 | 12/2001 | Wong et al. |
| 6,355,271 B1 | 3/2002 | Bell et al. |
| 6,375,972 B1 | 4/2002 | Guo et al. |
| 6,433,145 B1 | 8/2002 | LaFleur et al. |
| 6,479,729 B1 * | 11/2002 | Campochiaro et al. | 800/18 |
| 6,506,559 B1 | 1/2003 | Fire et al. |
| 6,852,510 B2 | 2/2005 | Bremel et al. |
| 7,056,704 B2 | 6/2006 | Tuschl et al. |
| 7,090,864 B2 | 8/2006 | Pardridge et al. |
| 7,148,342 B2 | 12/2006 | Tolentino et al. |
| 7,176,303 B2 * | 2/2007 | Freier et al. | 536/24.5 |
| 7,199,107 B2 * | 4/2007 | Dobie et al. | 514/44 A |
| 7,345,027 B2 | 3/2008 | Tolentino et al. |
| 7,468,431 B2 * | 12/2008 | Bhanot et al. | 536/24.5 |
| 7,674,895 B2 | 3/2010 | Reich et al. |
| 7,709,628 B2 * | 5/2010 | Freier et al. | 536/24.5 |
| 7,750,143 B2 | 7/2010 | Tolentino et al. |
| 2001/0021772 A1 | 9/2001 | Uhlmann et al. |
| 2002/0054902 A1 | 5/2002 | Pardridge |
| 2002/0086356 A1 | 7/2002 | Tuschl et al. |
| 2002/0132788 A1 | 9/2002 | Lewis et al. |
| 2002/0162126 A1 | 10/2002 | Beach et al. |
| 2002/0165158 A1 | 11/2002 | King |
| 2002/0173478 A1 | 11/2002 | Gewirtz |
| 2002/0183683 A1 | 12/2002 | Lerner |
| 2003/0138407 A1 | 7/2003 | Lu et al. |
| 2003/0153519 A1 | 8/2003 | Kay et al. |
| 2003/0216335 A1 | 11/2003 | Lockridge et al. |
| 2004/0018176 A1 | 1/2004 | Tolentino et al. |
| 2004/0018716 A1 | 1/2004 | Kitou et al. |
| 2004/0096848 A1 | 5/2004 | Thru et al. |
| 2004/0115640 A1 | 6/2004 | Myers et al. |
| 2004/0180357 A1 | 9/2004 | Reich et al. |
| 2004/0220129 A1 | 11/2004 | Reich et al. |
| 2004/0248174 A1 | 12/2004 | Reich et al. |
| 2004/0259247 A1 | 12/2004 | Tuschl et al. |
| 2005/0019927 A1 | 1/2005 | Hildinger et al. |
| 2005/0048529 A1 | 3/2005 | McSwiggen |
| 2005/0159380 A1 | 7/2005 | Guerciolini et al. |
| 2005/0187174 A1 | 8/2005 | Richards et al. |
| 2005/0197315 A1 | 9/2005 | Taira et al. |
| 2005/0222061 A1 | 10/2005 | Schulte |
| 2005/0246794 A1 | 11/2005 | Khvorova et al. |
| 2006/0003915 A1 | 1/2006 | Drumm et al. |
| 2006/0094032 A1 | 5/2006 | Fougerolles et al. |
| 2006/0182783 A1 | 8/2006 | Hughes et al. |
| 2006/0217332 A1 | 9/2006 | Vargeese et al. |
| 2006/0223770 A1 | 10/2006 | Fougerolles et al. |
| 2006/0286073 A1 | 12/2006 | Tolentino et al. |
| 2006/0292120 A1 | 12/2006 | Tolentino et al. |
| 2007/0003523 A1 | 1/2007 | Tolentino et al. |
| 2007/0037760 A1 | 2/2007 | Tolentino et al. |
| 2007/0037761 A1 | 2/2007 | Tolentino et al. |
| 2007/0037762 A1 | 2/2007 | Tolentino et al. |
| 2007/0149471 A1 | 6/2007 | Reich et al. |
| 2007/0178068 A1 | 8/2007 | Reich et al. |
| 2008/0188437 A1 | 8/2008 | Tolentino et al. |
| 2009/0061478 A1 | 3/2009 | Poulsen et al. |
| 2009/0104259 A1 | 4/2009 | Tolentino et al. |

FOREIGN PATENT DOCUMENTS

| | | |
|---|---|---|
| EP | 1144623 B1 | 8/2002 |
| EP | 1229134 A2 | 8/2002 |
| EP | 1578933 B1 | 3/2010 |
| IL | 166274 | 9/2010 |
| NZ | 537833 | 12/2010 |
| WO | WO93/24641 A2 | 12/1993 |
| WO | WO94/08026 A1 | 4/1994 |
| WO | WO94/13788 A1 | 6/1994 |
| WO | WO94/24274 A1 | 10/1994 |
| WO | WO94/29469 A2 | 12/1994 |
| WO | WO 95/04142 A2 | 2/1995 |
| WO | WO95/35367 A1 | 12/1995 |
| WO | WO97/00957 A1 | 1/1997 |
| WO | WO97/18855 A1 | 5/1997 |
| WO | WO97/20579 A2 | 6/1997 |
| WO | WO98/19847 A1 | 5/1998 |
| WO | WO98/22132 A1 | 5/1998 |
| WO | WO98/48009 A2 | 10/1998 |
| WO | WO99/12572 A1 | 3/1999 |
| WO | WO99/32619 A1 | 7/1999 |
| WO | WO98/56361 A1 | 12/1999 |
| WO | WO00/08141 A2 | 2/2000 |
| WO | WO 00/44895 A1 | 8/2000 |
| WO | WO00/44914 A1 | 8/2000 |
| WO | WO00/63364 A2 | 10/2000 |
| WO | WO01/36646 A1 | 5/2001 |
| WO | WO01/52904 A2 | 7/2001 |
| WO | WO01/57206 A2 | 8/2001 |
| WO | WO01/68836 A2 | 9/2001 |
| WO | WO 01/75164 A2 | 10/2001 |
| WO | WO01/77350 A2 | 10/2001 |
| WO | WO01/82900 A1 | 11/2001 |
| WO | WO01/83729 A2 | 11/2001 |
| WO | WO01/98522 A2 | 12/2001 |
| WO | WO02/08242 A1 | 1/2002 |
| WO | WO02/11666 2 | 2/2002 |
| WO | WO 02/44321 A2 | 6/2002 |
| WO | WO02/055692 A2 | 7/2002 |
| WO | WO02/055693 A2 | 7/2002 |
| WO | WO02/083184 A2 | 10/2002 |
| WO | WO02/088320 A2 | 11/2002 |
| WO | WO 02/096927 A2 | 12/2002 |
| WO | WO02/096957 A1 | 12/2002 |
| WO | WO03/000018 A2 | 1/2003 |
| WO | WO 03/012105 A2 | 2/2003 |
| WO | WO03/066805 A2 | 8/2003 |
| WO | WO03/070910 A2 | 8/2003 |
| WO | WO03/087367 A2 | 10/2003 |
| WO | WO03/087368 A2 | 10/2003 |
| WO | WO03/099298 A1 | 12/2003 |
| WO | WO 2004/009769 A2 | 1/2004 |
| WO | WO2004/013310 A2 | 2/2004 |
| WO | WO2004/065546 A2 | 8/2004 |
| WO | WO2004/094606 A2 | 11/2004 |
| WO | WO2005/028649 A1 | 3/2005 |
| WO | WO2006/110813 A2 | 10/2006 |
| WO | WO 2007/067981 A2 | 6/2007 |
| WO | WO 2007/146953 A2 | 12/2007 |
| WO | WO 2008/030996 A2 | 3/2008 |
| WO | WO 2008/110777 A2 | 9/2008 |

OTHER PUBLICATIONS

Scanlon, KJ (Current Pharmaceutical Biotechnology, 2004 vol. 5:415-420).*

Vickers et al. (Journal of Biological Chemistry, 2003 vol. 278: 7108-7118, Epub date Dec. 23, 2002).*

U.S. Appl. No. 12/636,075, Tolentino et al., Dec. 11, 2009.

Houck et al., The Vascular Endothelial Growth Factor Family: Identification of a Fourth Molecular Species and Characterization of Alternative Splicing of RNA, 1991, Mol. Endo., 5(12):1806-1814.

Elbashir et al., RNA Interference is Mediated by 21- and 22-Nucleotide RNAs, 2001, Genes and Development, 15:188-200.

Shi et al., Inhibition of Renal Cell Carcinoma Angiogenesis and Growth by Antisense Oligonucleotides Targeting Vascular Endothelial Growth Factor, 2002, British J. Cancer, 87(1):119-126.

Brantl, Antisense-RNA Regulation and RNA Interference, 2002, Biochimica et Biophysica Acta, 1575:15-25.

Kleinman et al., Sequence- and Target-Independent Angiogenesis Suppression by siRNA Via TLR3, Apr. 3, 2008, Nature, 452:591-598.

Berkhout, An Eye-Opener for RNAi Therapeutics, 2008, J. Formos Med. Assoc., 107(10):749-750.

Elbashir et al., Analysis of Gene Function in Somatic Mammalian Cells Using Small Interfering RNAs, 2002, Methods, 26:199-213.

Bates et al., $VEGF_{165}b$, an Inhibitory Splice Variant of Vascular Endothelial Growth Factor, Is Down-Regulated in Renal Cell Carcinoma, Jul. 15, 2002, Cancer Res., 62:4123-4131.

Sato et al., Human cDNA for Vascular Endothelial Growth Factor Isoform VEGF121, 1999, GenBank Accession No. AF214570.

Belletti et al., Modulation of in Vivo Growth of Thyroid Tumor-Derived Cell Lines by Sense and Antisense Vascular Endothelial Growth Factor Gene, 1999, Oncogene, 18:4860-4869.

Tolentino et al., Intravitreal Injection of Vascular Endothelial Growth Factor Small Interfering RNA Inhibits Growth and Leakage in a Nonhuman Primate, Laser-Induced Model of Choroidal Neovascularization, 2004, Retina, 24(1):132-138.

Lu et al., Delivering siRNA In Vivo for Functional Genomics and Novel Therapeutics, from RNA Interference Technology, 2005, Cambridge University Press, New York, USA, Appasani ed., pp. 303-317.

Downward, Science, Medicine and the Future, RNA Interference, May 22, 2004, BMJ, 328:1245-1248.

Nielsen, Systemic Delivery. The Last Hurdle? Mar. 10, 2005, Gene Therapy, 12:956-957.

Reich et al., Small Interfering RNA (siRNA) Targeting VEGF Effectively Inhibits Ocular Neovascularization in a Mouse Model, May 30, 2003, Molecular Vision, 9(31):210-216.

Shu et al., Sphingosine Kinase Mediates Vascular Endothelial Growth Factor-Induced Activation of Ras and Mitogen-Activated Protein Kinases, Nov. 2002, Mol. Cell Biol., 22(22):7758-7768.

Samarsky et al., RNAi in Drug Development: Practical Considerations, From RNA Interference Technology, 2005, Cambridge University Press, New York, USA, Appasani, ed., pp. 384-395.

McCaffrey et al., RNA Interference in Adult Mice, Jul. 4, 2002, Nature, 418:38-39.

Hasan et al., VEGF Antagonists, 2001, Expert Opinion in Biological Therapeutics, 1(4):703-718.

Levy et al., Post-Transcriptional Regulation of Vascular Endothelial Growth Factor by Hypoxia, Feb. 2, 1996, J. Biol. Chem., 271(5):2746-2753.

Elbashir et al., Duplexes of 21-Nucleotide RNAs Mediate RNA Interference in Cultured Mammalian Cells, May 24, 2001, Nature, 411:494-498.

Konopatskaya et al., VEGF(165)b, an Endogenous C-terminal Splice Variant or VEGF, Inhibits Retinal Neovascularization in Mice, May 1, 2006, Molecular Vision, 12(67-69):626-632.

Rennel et al., The Endogenous Anti-Angiogenic VEGF Isoform, VEGF(165)b Inhibits Human Tumour Growth in Mice, Apr. 2008, British Journal of Cancer, 98(7): 1250-1257.

Rennel et al., Recombinant Human VEGF165b Protein is an Effective Anti-Cancer Agent in Mice, Sep. 1, 2008, European Journal of Cancer, 44(13):1883-1894.

Acheampong, et al., Distribution of Brimonidine into Anterior and Posterior Tissues of Monkey, Rabbit, and Rat Eyes, *Drug Metabol. ISM & Disposition* (Apr. 1, 2002), 30(4):421-429.

Adamis, et al., Inhibition of Vascular Endothelial Growth Factor Prevents Retinal Ischemia-Associated Iris Neovascularization in a Nonhuman Primate, *Arch. Ophthal.* (Jan. 1996), 114(1):66-71.

Addis-Lieser, et al., Opposing Regulatory Roles of Complement Factor 5 in the Development of Bleomycin-Induced Pulmonary Fibrosis, *J. Immunol.* (Aug. 1, 2005), 175(3):1894-1902.

Agami, RNAi and Related Mechanisms and Their Potential Use for Therapy, *Curr. Opin. Chem. Biol.* (Oct. 18, 2002), 6(6):829-834.

Agrawal, et al., Antisense Therapeutics: Is It As Simple As Complementary Base Recognition?, *Mol. Med. Today* (Feb. 1, 2000), 6(2):72-81.

Alexion Pharmaceuticals, Alexion Pharmaceuticals Initiates Treatment in Pivotal Phase III Eculizummab Program in Paraxysmal Nocturnal Emoglobinuria Patients, *News and Information* @www.alexionpharm.com. (Sep. 23, 2004).

Altschul, et al., Basic Local Alignment Search Tool, *J. Mol. Biol.* (Oct. 5, 1990), 215(3):403-410.

Altschul, et al., Gapped BLAST and PSI-BLAST: a New Generation of Protein Database Search Programs, *Nucleic Acids. Res.* (Sep. 1, 1997), 25(17):3389-3402.

Amarzguioui, Secondary structure prediction and in vitro accessability of mRNA as tools in the selection of target sites for ribozymes, *Nucleic Acids Res.* (Nov. 1, 2000), 28(21):4113-4124.

Ambati, et al., Transscleral Drug Delivery to the Retina and Choroid, *Prog. Retin. Eye Res.* (Mar. 2002), 21(2):145-151.

Ames, et al., Identification of a Selective Nonpeptide Antagonist of the Anaphylatoxin C3a Receptor That Demonstrates Antiinflammatory Activity in Animal Models, *J. Immunol.* (May 15, 2001), 166(10):6341-6348.

Anderson, et al., A Role for Local Inflammation in the Formation of Drusen in the Aging Eye, *Am. J. Ophthalmol.* (Sep. 2002), 134(3):411-431.

Anderson, et al., Vitronectin Gene Expression in the Adult Human Retina, Invest. Ophthalmol. Vis. Sci. (Dec. 1999), 40(13):3305-3315.

Anderson, Human Gene Therapy, *Nature* (Apr. 30, 1998), 392:S25-S31.

Andra, et al., Generation and Characterization of Transgenic Mice Expressing Cobra Venom Factor, *Molecular Immunology* (Oct. 2002), 39(5-6):357-365.

Asahara, et al., Introduction of Gene into the Rabbit Eye by Iontophoresis: Preliminary Report, *JPN J. of Ophthalmol.* (Jan.-Feb. 2001), 45(1):31-39.

Avgeropoulos, et al., New treatment strategies for malignant gliomas, *The Oncologist* (Jun. 1999), 4(3):209-224.

Banan, et al., The Ins and Outs of RNAi in Mammalian Cells, *Curr. Pharm. Biotechnol.* (Oct. 2004), 5(5):441-450.

Banks, et al., Delivery across the blood-brain barrier of antisense directed against Amyloid β: reversal of learning and memory deficits in mice overexpressing Amyloid precursor protein, *J. Pharmaco. Exp. Ther.* (Jun. 1, 2001), 297(3):1113-1121.

Bao, et al., C5a Promotes Development of Experimental Lupus Nephritis which Can be Blocked with a Specific Receptor Antagonist, *Eur. J. Immunol.* (Aug. 2005), 35(8):2496-2506.

Bartz, et al., Production of High-Titer Human Immunodeficiency Virus Type 1 Pseudotyped with Vesiculuar Stomatitis Virus Glycoprotein, *Methods* (Aug. 1, 1997), 12(4):337-342.

Bass, The Short Answer, *Nature* (May 24, 2001), 411:428-429.

Bennett, et al., Humoral Response After Administration of E1-deleted Adenoviruses: Immune Privilege of the Subretinal Space, *Hum. Gene. Ther.* (Sep. 10, 1996), 7(14):1763-1769 (Abstract).

Bernstein, et al., Role for a bidentate ribonuclease in the initiation step of RNA interference, *Nature* (Jan. 18, 2001), 409(6818):363-366.

Blinder, et al., Effect of Lesion Size, Visual Acuity, and Lesion Composition on Visual Acuity Change with and without Verteporfin Therapy for Choroidal Neovascularization Secondary to Age-Related Macular Degeneration: TAP and VIP Report No. 1,*Am. J. Ophthal.* (Sep. 2003), 136(3):407-418.

Blom, et al., Complement Inhibitor C4b-binding Protein—Friend or Foe in the Innate Immune System?,*Mol. Immunol.* (Apr. 2004), 40(18):1333-1346.

Boado, Antisense drug delivery through the blood-brain barrier, *Adv. Drug Delivery Reviews* (Jul. 1995), 15(1-3):73-107.

Boado, et al., Drug delivery of antisense molecules to the brain for treatment of Alzheimer's disease and cerebral AIDS, *J. Pharm. Sci.* (Nov. 1998), 87(11):1308-1315.

Bok, Evidence for an Inflammatory Process in Age-Related Macular Degeneration Gains New Support, *PNAS USA* (May 17, 2005), 102(20):7053-7054.

Bonilha, et al., Ezrin Promotes Morphogenesis of Apical Microvilli and Basal Infoldings in Retinal Pigment Epithelium, *J. Cell Biol.* (Dec. 27, 1999), 147(7):1533-1548.

Boocock, et al., Expression of Vascular Endothelial Growth Factor and its Receptors flt and KDR in Ovarian Carcinoma, *J. Natl. Cancer Inst.* (Apr. 5, 1995), 8(7):506-516.

Bora, et al., Role of Complement and Complement Membrane Attack Complex in Laser-induced Choroidal Neovascularization, *J. Immun.* (Jan. 1, 2005), 174(1):491-497.

Bressler, et al., Verteporfin Therapy of Subfoveal Choroidal Neovascularization in Patients with Age-Related Macular Degeneration, *Arch. Ophthalmol.* (Nov. 2002), 120(11):1443-1454.

Brummelkamp, et al., A System for Stable Expression of Short Interfering RNAs in Mammalian Cells, *Science* (Apr. 19, 2002), 296(5567):550-553.

Bullard, et al., Direct Comparison of Nick-Joining Activity of the Nucleic Acid Ligases from Bacteriophage T4, *Biochem. J.* (Aug. 15, 2006), 398(1):135-144.

Bustin, Absolute Quantification of mRNA Using Real-time Reverse Transcription Polymerase Chain Reaction Assays, *J. Mol. Endocrinol.* (Oct. 2000), 25(2):169-193.

Cai, et al., A Direct Role for C1 Inhibitor in Regulation of Leukocyte Adhesion, *J. Immunol.* (May 15, 2005), 174(10):6462-6466.

Campochiaro, Gene therapy for retinal and choroidal diseases, *Expert Opn. Biol. Ther.* (Jun. 2002), 2(5):537-544.

Capeans, et al., A c-*myc* Antisense Oligonucleotide Inhibits Human Retinal Pigment Epithelial Cell Proliferation, *Exp. Eye Res.* (May 1998), 66(5):581-589.

Caplen, A New Approach to the Inhibition of Gene Expression, *Biotechnol.* (Feb. 1, 2002), 20(2):49-51.

Caplen, et al., Specific inhibition of gene expression by small double-stranded RNAs in invertebrate and vertebrate systems, *Proc. Natl Acad Sci* (Aug. 14, 2001), 98(17):9742-9747.

Caplen, Gene Therapy Progress and Prospect. Downregulating Gene Expression: The Impact of RNA Interference, *Gene Therapy* (Aug. 2004), 11(16):1241-1248.

Caplen, RNAi as a Gene Therapy Approach, *Expert Opin. Biol. Ther.* (Jul. 2003), 3(4):575-586.

Carlson, et al., Perineurium in the *Drosophila* (Diptera: Drosophilidae) Embryo and Its Role in the Blood-Brain/Nerve Barrier, *Int. J. Insect Morphol. Embryol.* (Apr. 1998), 27(2):61-66.

Chan, et al., Expression of chemokine receptors, CXCR4 and CXCR5, and chemokines, BLC and SDF-1, in the eyes of patients with primary intraocular lymphoma, *Ophthalmology* (Feb. 2003), 110(2):421-426.

Chen, et al., Prevention of Hyperacute Rejection of Pig-to-Monkey Cardiac Xenografts by Chinese Cobra Venom Factor, *Transplant Proc.* (Nov.-Dec. 2001), 33(7-8):3857-3858.

Chirila, et al., The Use of Synthetic Polymers for Delivery of Therapeutic Antisense Oligodeoxynucleotides, *Biomaterials* (Jan. 2002), 23(2):321-342.

Cho, Small Interfering RNA-induced TLR3 Activation Inhibits Blood and Lymphatic Vessel Growth, *PNAS USA* (Apr. 28, 2009), 106(17):7137-7142.

Coburn, et al., siRNAs: a New Wave of RNA-Based Therapeutics, *J. Antimicrob. Chemother.* (Apr. 2003), 51(4):753-756.

Collins, et al., The Human β-Subunit of Rod Photoreceptor cGMP Phosphodiesterase: Complete Retinal cDNA Sequence and Evidence for Expression in Brain, *Genomics* (Jul. 1992), 13(3):698-704.

Conley, et al., Candidate Gene Analysis Suggests a Role for Fatty Acid Biosynthesis and Regulation of the Complement System in the Etiology of Age-Related Maculopathy, *Human Mol. Genetics* (Jul. 15, 2005), 14(14):1991-2002.

Crooke, Progress in Antisense Technology: The End of the Beginning, *Methods Enzymol.* (2000), 313:3-45.

Daiger, Was the Human Genome Project Worth the Effort?, *Science* (Apr. 15, 2005), 308(5720):362-364.

Davis, et al., The Age-Related Eye Disease Study Severity Scale for Age-Related Macular Degeneration: AREDS *Report No. 17, Arch. Ophthalmol.* (Nov. 2005), 123(11):1484-1498.

Deonarain, Ligand-Targeted Receptor-Mediated Vectors for Gene Delivery, *Expert Opin. Ther. Pat.* (Jan. 1998), 8(1):53-69.

Detrick, et al., Inhibition of Human Cytomegalovirus Replication in a Human Retinal Epithelial Cell Model by Antisense Oligonucleotides, *Invest. Ophthalmol. Vis. Sci.* (Jan. 2001), 42(1):163-169.

Devroe, et al., Retrovirus-delivered siRNA, *BMC Biotech.* (Aug. 28, 2002), 2:1-5.

Dornburg, Reticuloendotheliosis Viruses and Derived Vectors, *Gene Therap.* (Jul. 1995), 2(5):301-310.

Dorsett, et al., siRNAs: Applications in Functional Genomics and Potential as Therapeutics, *Nat. Rev. Drug Discov.* (Apr. 2004), 3(4):318-329.

Dragun, et al., ICAM-1 Antisense Oligodesoxynucleotides Prevent Reperfusion Injury and Enhance Immediate Graft Function in Renal Transplantation, *Kidney Int.* (1998), 54(2):590-602.

Dryja, et al., Mutations in the gene encoding the α subunit of the rod cGMP-gated channel in autosomal recessive retinitis pigmentosa, *PNAS USA* (Oct. 24, 1995), 92(22):10177-10181.

Dyer, et al., The Role of Complement in Immunological Demyelination of the Mammalian Spinal Cord, *Spinal Cord* (Jul. 1, 2005), 43(7):417-425.

Dzitoyeva, et al., Intra-abdominal injection of double stranded RNA into anesthetized adult *Drosophila* triggers RNA interference in the central nervous system, *Mol. Psychiatry* (Nov. 2001), 6(6):665-670.

EBI Accession No. GSN-ADY90830—Retrieved from online database Jun. 16, 2005, VEGF siRNA SEQ ID No. 3868, XP002468091.

EBI Accession No. GSN-ADY90830—Retrieved from online database Jun. 16, 2005, VEGF siRNA SEQ ID No. 3867, XP002468090.

Edwards, et al., Complement Factor H Polymorphism and Age-Related Macular Degeneration, *Science* (Apr. 15, 2005), 308(5720):421-424.

Eglitis, et al., Retroviral Vectors for Introduction of Genes into Mammalian Cells, *BioTechniques* (Jul. 1, 1988), 6(7):608-614.

Elbashir, et al., Functional Anatomy of siRNAs for Mediating Efficient RNAi in *Drosophila* Melanogaster Embryo Lysate, *EMBO J.* (Dec. 3, 2001), 20(23):6877-6888.

Engstrom, et al., Complement C3 is a Risk Factor for the Development of Diabetes: a Population-Based Cohort Study, *Diabetes* (Feb. 2005), 54(2):570-575.

Epstein, Antisense Inhibition of Phosphodiesterase Expression, *Methods* (Jan. 1998), 14(1):21-33.

Erickson, RNAi Revs Up, *Start-Up Emerging Medical Ventures* (Art. #2002900168) (Oct. 1, 2002), pp. 1-12.

Far, et al., The Activity of siRNA in Mammalian Cells is Related to Structural Target Accessibility: a Comparison with Antisense Oligonucleotides, *Nucleic Acids Res.* (Aug. 1, 2003), 31(15):4417-4424.

Finehout, et al., Complement Protein Isoforms in CSF as Possible Biomarkers for Neurodegenerative Disease, *Dis Markers* (May 16, 2005), 21(2):93-101 (Abstract).

Fire, et al., Potent and Specific Genetic Interference by Double-Stranded RNA in *Caenorhabditis Elegans, Nature* (Feb. 19, 1998), 391(6669):806-811.

Fisher, et al., Transduction with Recombinant Adeno-Associated Virus for Gene Therapy is Limited by Leading-Strand Synthesis, *J. Virol.* (Jan. 1996), 70(1):520-532.

Fjose, et al., RNAi and MicroRNAs: from Animal Models to Disease Therapy, *Birth Defects Res.* (Jun. 2006), 78(2):150-171.

Fujita, et al., Complement Activation Accelerates Glomerular Injury in Diabetic Rats, *Nephron* (Feb. 1999), 81(2):208-214.

Fung, et al., Inhibition of Complement, Neutrophil, and Platelet Activation by an Anti-Factor D Monoclonal Antibody in Simulated Cardiopulmonary Bypass Circuits, *J. Thorac. Cardiovasc. Surg.* (Jul. 2001), 122(1):113-122.

Gabizon, et al., Liposome Formulations With Prolonged Circulation Time in Blood and Enhanced Uptake by Tumors, *PNAS USA* (Sep. 1988), 85(18):6949-6953.

Gan, et al., Specific Interference of Gene Function by Double-Stranded RNA in Neuronal Cell Lines, Program No. 772.10, 2001 Neuroscience Meeting Planner. San Diego, CA (Nov. 14, 2001) (Abstract only).

Ganesh, et al., Structure of Vaccinia Complement Protein in Complex with Heparin and Potential Implications for Complement Regulation, *PNAS USA* (Jun. 15, 2004), 101(24):8924-8929.

Gardlik, et al., Vectors and Delivery Systems in Gene Therapy, *Med. Sci. Monit.* (Apr. 2005), 11(4):RA110-121.

Garrett, et al., In vivo use of oligonucleotides to inhibit choroidal neovascularisation in the eye, *J Gene Med* (Jul.-Aug. 2001), 3(4):373-383.
GENBANK Accession No. AJ 245445, 1999 (Einspanier—Fltl).
Gompels, et al., C1 inhibitor deficiency: consensus document, *Clin Exp. Immunol.* (Mar. 2005), 139(3):379-394.
Goncalves, A concise peer into the background, initial thoughts and practices of human gene therapy, *BioEssays* (May 2005), 27(5):506-517.
Grishok, et al., Genes and Mechanisms Related to RNA Interference Regulate Expression of the Small Temporal RNAs that Control *C. elegans* Development Timing, *Cell* (Jul. 13, 2001), 106:23-34.
Groothuis, The blood-brain and blood-tumor barriers: a review of strategies for increasing drug delivery, *Neuro Oncol.* (Jan. 2000), 2(1):45-59.
Guo, et al., Role of C5A in Inflammatory Responses, *Annu Rev Immunol.* (2005), 23:821-852.
Hageman, et al., A common haplotype in the complement regulatory gene factor H (*HF1/CFH*) predisposes individuals to age-related macular degeneration, *Proc Natl Acad Sci USA* (May 17, 2005), 102(20):7227-7232.
Hageman, et al., An Integrated Hypothesis that Considers Drusen as Biomarkers of Immune-Mediated Processes at the RPE-Bruch's Membrane Interface in Aging and Age-Related Macular Degeneration, *Prog Retin Eye Res.* (Nov. 2001), 20(6):705-732.
Hageman, et al., Molecular composition of drusen as related to substructural phenotype, *Mol. Vis.* (Nov. 3, 1999), 5:28-37.
Haines, et al., Complement Factor H Variant Increases the Risk of Age-Related Macular Degeneration, *Science* (Apr. 15, 2005), 308(5720):419-421.
Halstead, et al., Complement Inhibition Abrogates Terminal Injury in Miller Fisher Syndrome, *Ann Neurol.* (Aug. 2005), 58(2):203-210.
Hamilton, et al., A species of small antisense RNA in post-transcriptional gene silencing in plants, *Science* (Oct. 29, 1999), 286(5441): 950-952.
Hammond, et al., Post-transcriptional Gene Silencing by Double-Stranded RNA, *Nat Rev Genet* (Feb. 2001), 2(2):110-119.
Harborth, et al., Self Assembly of NuMA multiarm oligomers as structural units of a nuclear lattice, *EMBO J.* (Mar. 15, 1999), 18(6):1689-1700.
Harborth, et al., Sequence, Chemical, and Structural Variation of Small Interfering RNAs and Short Hairpin RNAs and the Effect on Mammalian Gene Silencing, *Antisense Nucleic Acid Drug Dev.* (Apr. 2003), 13(2):83-105.
Hart, et al., Genotype-Phenotype Correlation of Mouse *Pde6b* Mutations, *Invest Ophthalmos Vis Sci.* (Sep. 2005), 46(9):3443-3450.
Hart, et al., Initiation of complement activation following oxidative stress. In vitro and in vivo observations, *Mol Immunol.* (Jun. 2004), 41(2-3):165-171.
He, et al., Complement Inhibitors Targeted to the Proximal Tubule Prevent Injury in Experimental Nephrotic Syndrome and Demonstrate a Key Role for C5b-9, *J Immunol.* (May 1, 2005), 174(9):5750-5757.
Hillebrandt, et al., Complement factor 5 is a quantitative trait gene that modifies liver fibrogenesis in mice and humans, *Nat. Genet* (Aug. 2005), 37(8):835-843.
Hodgetts, et al., Complement and myoblast transfer therapy: Donor myoblast survival is enhanced following depletion of host complement C3 using cobra venom factor, but not in the absence of C5, *Immunol Cell Biol.* (Jun. 2001), 79(3):231-239.
Hoeg, et al., In Vitro and In Vivo Efficacy of a HIF-1 Alpha-Antisense Oligonucleotide Containing Locked Nucleic Acids, *ECJ Supplements* (Sep. 24, 2003), pp. S212-S213 (Abstract).
Holash, et al., VEGF-Trap: A VEGF blocker with potent antitumor effects, *Proc Natl Acad Sci USA* (Aug. 20, 2002), 99(17):11393-11398.
Holers, et al., The alternative pathway of complement in disease: opportunities for therapeutic targeting, *Mol Immunol.* (Jun. 2004), 41(2-3):147-152.
Hunt, et al., Vitreous Treatment of Retinal Pigment Epithelial Cells Results in Decreased Expression of FGF-2, *Invest Ophthalmol Vis Sci.* (Oct. 1998), 39(11):2111-2120.

Jakobsdottir, et al., Susceptibility Genes for Age-Related Maculopathy on Chromosome 10q26, *Am J Hum Genet.* (Sep. 2005), 77(3):389-407.
Jen, et al., Suppression of Gene Expression by Targeted Disruption of Messenger RNA: Available Options and Current Strategies, *Stem Cells* (2000), 18(5):307-319.
Jha, et al., Vaccinia complement control protein: Multi-functional protein and a potential wonder drug, *J Biosci.* (Apr. 2003), 28(3):265-271.
Johnson, et al., A Potential Role for Immune Complex Pathogenesis in Drusen Formation, *Exp Eye Res.* (Apr. 2000), 70(4):441-449.
Johnson, et al., Complement Activation and Inflammatory Processes in Drusen Formation and Age Related Macular Degeneration, *Exp Eye Res.* (Dec. 2001), 73(6):887-896.
Johnson, et al., The Alzheimer's Aβ-peptide is deposited at sites of complement activation in pathologic deposits associated with aging and age-related macular degeneration, *Proc Natl Acad Sci USA* (Sep. 3, 2002), 99(18):11830-11835.
Kang, et al., An Antisense Oligonucleotide that Inhibits the Expression of Hypoxia-Inducible Factor-1 Alpha Alters Hypoxia-Induced Changes in Proliferation and Viability of Human Cardiac Fibroblasts, Abstracts from Scientific Sessions 2001 II-57:274 (Abstract).
Kasschau, et al., A Counterdefensive Strategy of Plant Viruses: Suppression of Posttranscriptional Gene Silencing, *Cell* (Nov. 13, 1998), 95(4):461-470.
Katz, et al., ICAM-1 Antisense Oligodeoxynucleotide Improves Islet Allograft Survival and Function, *Cell Transplant.* (Nov.-Dec. 2000), 9(6):817-828.
Kim, et al., Potent VEGF blockade causes regression of coopted vessels in a model of neuroblastoma, *Proc Natl Acad Sci USA.* (Aug. 20, 2002), 99(17):11399-11404.
Klein, et al., Complement Factor H Polymorphism in Age-Related Macular Degeneration, *Science* (Apr. 15, 2005), 308(5720):385-389.
Knight, et al., A Role for the RNase III Enzyme DCR-1 in RNA Interference and Germ Line Development in *Caenorhabditis elegans, Science* (Sep. 21, 2001), 293(5538):2269-2271.
Kociok, et al., Upregulation of RAS-GTPase Activating Protein (GAP)-Binding Protein (G3BP), in Proliferating RPE Cells, *J Cell Biochem.* (Aug. 1, 1999), 74(2):194-201.
Kociok, et al., Vitreous Treatment of Cultured Human RPE Cells Results in Differential Expression of 10 New Genes, *Invest Ophthalmol Vis Sci.* (Jul. 2002), 43(7):2474-2480.
Kock, et al., Structure and Function of Recombinant Cobra Venom Factor, *J Biol Chem.* (Jul. 16, 2004), 279(29):30836-30843.
Kostelny, et al., Formation of a Bispecific Antibody by the Use of Leucine Zippers, J Immunol. (Mar. 1, 1992), 148(5):1547-1553.
Krishnamachary, et al., Regulation of Colon Carcinoma Cell Invasion by Hypoxia-Inducible Factor 1, *Cancer Res.* (Mar. 1, 2003), 63(5):1138-1143.
Kuehn, Gene Discovery Provides Clues to Cause of Age-Related Macular Degeneration, *JAMA* (Apr. 20, 2005), 293(15):1841-1845.
Kurschat, et al., Optimizing splinted ligation of highly structured small RNAs, RNA. (Dec. 2005), 11(12):1909-1914.
Lai, et al., The Use of Adenovirus-Mediated Gene Transfer to Develop a Rat Model for Photoreceptor Degeneration, *Invest. Ophthalmol Vis Sci.* (Feb. 2000), 41(2):580-584.
Lawson, et al., Understanding the Glaucoma Gene, *Developmental Control of Gene Expression* (2000), 69-74:14a (Abstract).
Leconte, et al., Impairment of Rod cGMP-Gated Channel α-Subunit Expression Leads to Photoreceptor and Bipolar Cell Degeneration, *Invest. Ophthalmol. Vis Sci.* (Mar. 2000), 41(3):917-926.
Lee, et al., Expression of small interfering RNAs targeted against HIV-1 *rev* transcripts in human cells, *Nat Biotechnol.* (May 2002), 20(5):500-505.
Lee, et al., Imaging Gene Expression in the Brain In Vivo in a Transgenic Mouse Model of Huntington's Disease with an Antisense Radiopharmaceutical and Drug-Targeting Technology, *J Nucl Med.* (Jul. 2002), 43(7):948-956.
Lewin, et al., Ribozyme rescue of photoreceptor cells in a transgenic rat model of autosomal dominant retinitis pigmentosa, *Nat Med.* (Aug. 1, 1998), 4(8):967-971.

Lewis, et al., A serum-resistance cytofectin for cellular delivery of antisense oligodeoxynucleotides and plasmid DNA, *Proc Natl Acad Sci USA.* (Apr. 16, 1996), 93(8):3176-3181.

Linton, et al., Therapeutic efficacy of a novel membrane-targeted complement regulator in antigen-induced arthritis in the rat, *Arthritis Rheum.* (Nov. 2000), 43(11):2590-2597 (Abstract).

Liu, et al., Ribozyme Knockdown of the γ-Subunit of Rod cGMP Phosphodiesterase Alters the ERG and Retinal Morphology in Wild-Type Mice, *Invest Ophthalmol Vis Sci.* (Oct. 2005), 46(10):3836-3844.

Lucas, et al., Secreted Immunomodulatory Viral Proteins as Novel Biotherapeutics, *J Immunol.* (Oct. 15, 2004), 173(8):4765-4774.

Manoharan, RNA interference and chemically modified small interfering RNAs, *Curr Opin Chem Biol.* (Dec. 2004), 8(6):570-579.

Marchand, et al., Blockade of in vivo VEGF-mediated angiogenesis by antisense gene therapy: role of Flk-1 and Flt-1 receptors, *Am J Physiol Heart Circ Physiol.* (Jan. 2002), 282(1):H194-H204.

Martinez, et al., Single-Stranded Antisense siRNAs Guide Target RNA Cleavage in RNAi, *Cell* (Sep. 6, 2002), 110(5):563-574.

Mastellos, et al., From atoms to aystems: a cross-disciplinary approach to complement-mediated functions, *Mol Immunol.* (Jun. 2004), 41(2-3):153-164.

Mastellos, et al., Novel biological networks modulated by complement, *Clinical Immunol.* (Jun. 2005), 115(3):225-235.

Merriam-Webster's Online Dictionary, Definition of Ligand, http://www.merriam-webster.com/ dictionary/ligand (Jun. 2, 2008).

Miller, Retrovirus Packaging Cells, *Hum Gene Ther.* (Spring 1990), 1(1):5-14 (Abstract).

Miyagishi, et al., U6 promoter-driven siRNAs with four uridine 3' overhangs efficiently suppress targeted gene expression in mammalian cells, *Nat Biotechnol.* (May 2002), 20(5):497-500.

Miyamoto, et al., Prevention of leukostasis and vascular leakage in streptozotocin-induced diabetic retinopathy via intercellular adhesion molecule-1 inhibition, *Proc Natl Acad Sci USA.* (Sep. 14, 1999), 96(19):10836-10841.

Miyamoto, et al., Vascular Endothelial Growth Factor (VEGF)-Induced Retinal Vascular Permeability is Mediated by Intercellular Adhesion Molecule-1 (ICAM-1), *Am J Pathol.* (May 2000), 156(5):1733-1739.

Mollnes, et al., Complement in inflammatory tissue damage and disease, *Trends Immunol.* (Feb. 2002), 23(2):61-64.

Moromizato, et al., CD18 and ICAM-1 Dependent Corneal Neovascularization and Inflammation after Limbal Injury, *Am J Pathol.* (Oct. 2000), 157(4):1277-1281.

Mothe, et al., Analysis of Green Flourescent Protein Expression in Transgenic Rats for Tracking Transplanted Neural Stem/Progenitor Cells, *J Histochem Cytochem.* (Oct. 2005), 53(10):1215-1226.

Moulton, Metrics on RNA Secondary Structures, *J Comput Biol.* (Feb.-Apr. 2000), 7(1-2):277-292.

Mullins, et al., Drusen associated with aging and age-related macular degeneration contain proteins common to extracellular deposits associated with atherosclerosis, elastosis, amyloidosis, and dense deposit disease, *FASEB J.* (May 1, 2000), 14(7):835-846.

Nandakumar, et al., RNA Substrate Specificity and Structure-guided Mutational Analysis of Bacteriophage T4 RNA Ligase 2, *J Biol Chem.* (Jul. 23, 2004), 279(30):31337-31347.

Nguyen, et al., Minimising the secondary structure of DNA targets by incorporation of a modified deoxynucleoside: implications for nucleic acid analysis by hybridisation, *Nucleic Acids Res.* (Oct. 15, 2000), 28(20):3904-3909.

Nishiwaki, et al., Introduction of short interfering RNA to silence endogenous E-selection in vascular endothelium leads to successful inhibition of leukocyte adhesion, *Biochem Biophys Res Commun.* (Oct. 31, 2003), 310(4):1062-1066.

Novina, et al., siRNA-directed inhibition of HIV-1 infection, *Nat Med.* (Jul. 2002), 8(7):681-686.

Nuckel, et al., Alemtuzumab induces enhanced apoptosis in vitro in B-cells from patients with chronic lymphocytic leukemia by antibody-dependent cellular cytotoxicity, *Eur J Pharmacol.* (May 9, 2005), 514(2-3):217-224.

Ogata, et al., Transfection of basic fibroblast growth factor (bFGF) gene or bFGF antisense fene into human fetinal pigment epithelia cells, *Graefe's Arch Clin Exp Ophthalmol.* (Aug. 1999), 237(8):678-684.

Ohali, et al., Complement profile in childhood immune thrombocytopenic purpura: a prospective pilot study, *Ann Hematol.* (Nov. 2005), 84(12):812-815.

Opalinska, et al., Nucleic-Acid Therapeutics: Basic Principles and Recent Applications, *Nat Rev Drug Discov.* (Jul. 2002), 1(7):503-514.

Ostergaard, et al., Complement activation and diabetic vascular complications, *Clin Chim Acta.* (Nov. 2005), 361(1-2):10-19.

Paddison, et al., Short hairpin RNAs (shRNAs), induce sequence-specific silencing in mammalian cells, *Genes Dev.* (Apr. 15, 2002), 16(8):948-958.

Pardridge, Brain Drug Targeting and Gene Technologies, *Jpn J Pharmacol.* (Oct. 2001), 87(2):97-103.

Pardridge, CNS Drug Design Based on Principles of Blood-Brain Barrier Transport, *J Neurochem.* (May 1998), 70(5):1781-1792.

Pardridge, Drug and gene targeting to the brain with molecular Trojan horses, *Nat Rev Drug Discov.* (Feb. 2002), 1(2):131-139.

Pardridge, Drug Delivery to the Brain, *J Cereb. Blood Flow Metab.* (Jul. 1997), 17(7):713-731.

Pardridge, et al., Vector-mediated delivery of a polyamide ("peptide"), nucleic acid analogue through the blood-brain barrier in vivo, *Proc Natl Acad Sci USA.* (Jun. 6, 1995), 92(12):5592-5596.

Pardridge, Vector-mediated drug delivery to the brain, *Adv Drug Deliv Rev.* (Apr. 5, 1999), 36(2-3):299-321.

Paroo, et al., Challenges for RNAi in vivo, *Trends Biotechnol.* (Aug. 2004), 22(8):390-394.

Patterson, et al., Cloning and functional analysis of the promoter for KDR/flk-1, a receptor for vascular endothelial growth factor, *J Biol Chem.* (Sep. 29, 1995), 270(39):23111-23118 (Abstract).

Paul, et al., Effective expression of small interfering RNA in human cells, *Nat Biotechnol.* (May 2002), 20(5):505-508.

Peng, et al., Role of C5 in the development of airway inflammation, airway hyperresponsiveness, and ongoing airway response, *J Clin Invest.* (Jun. 2005), 115(6):1590-1600.

Penichet, et al., An Antibody-Avidin Fusion Protein Specific for the Transferrin Receptor Serves as a Delivery Vehicle for Effective Brain Targeting: Initial Applications in Anti-HIV Antisense Drug Delivery to the Brain, *J Immunol.* (Oct. 15, 1999), 163(8):4421-4426.

Philip, et al., Polarized Expression of Monocarboxylate Transporters in Human Retinal Pigment Epithelium and ARPE-19 Cells, *Invest Ophthalmol Vis Sci.* (Apr. 1, 2003), 44(4):1716-1721.

Pineda, et al., The genetic network of prototypic planarian eye regeneration is Pax6 independent, *Development.* (Mar. 2002), 129(6):1423-1434.

Pratt, et al., Nontransgenic Hyperexpression of a Complement Regulator in Donor Kidney Modulates Transplant Ischemia/Reperfusion Damage, Acute Rejection, and Chronic Nephropathy, *Am J Pathol.* (Oct. 2003), 163(4):1457-1465.

Qian, et al., Targeted Drug Delivery via the Transferrin Receptor-Mediated Endocytosis Pathway, *Pharmacol Rev.* (Dec. 2002), 54(4):561-587.

Ramon, et al., Molecular Biology of Retinitis Pigmentosa: Therapeutic Implications, *Current Pharma.* (Dec. 2004), 2(4):339-349.

Remington's *Pharmaceutical Sciences*, 17th ed., Mack Publishing Co., Easton, PA. (1985), TOC (See Gennaro).

Roberts, et al., Efficient expression of ribozyme and reduction of stromelysin mRNA in cultured cells and tissue from rabbit knee via Adeno-associated Virus (AAV), *Gene Therapy and Mol. Biol.* (Dec. 1999), 4:45-58.

Rosenfeld, et al., Maximum Tolerated Dose of a Humanized Anti-Vascular Endothelial Growth Factor Antibody Fragment for Treating Neovascular Age-Related Macular Degeneration, *Opthalmology.* (Jun. 2005), 112(6):1048-1053.

Rother, et al., Inhibition of terminal complement: a novel therapeutic approach for the treatment of systemic lupus erythematosus, *Lupus* (2004), 13(5):328-334.

Rubinson, et al., A lentivirus-based system to functionally silence genes in primary mammalian cells, stem cells and transgenic mice by RNA interference, *Nat Genet.* (Mar. 2003), 33(3):401-406 (Abstract).

Rummelt, et al., Triple retinal infection with human immunodeficiency virus type 1, cytomegalovirus, and herpes simplex virus type 1. Light and electron microscopy, immunohistochemistry, and in situ hybridization, *Ophalmology.* (Feb. 1994), 101(2):270-279 (Abstract Only).

Russell, et al., Location, Substructure, and Composition of Basal Laminar Drusen Compared with Drusen Associated with Aging and Age-Related Macular Degeneration, *Am J Ophthalmol.* (Feb. 2000), 129(2):205-214.

Sakurai, et al., Targeted Disruption of the CD18 or ICAM-1 Gene Inhibits Choroidal Neovascularization, *Invest Ophthalmol Vis Sci.* (Jun. 2003), 44(6):2743-2749.

Samulski, et al., A Recombinant Plasmid from Which an Infectious Adeno-Associated Virus Genome Can Be Excised in Vitro and its use to Study Viral Replication, *J Virol.* (Oct. 1987), 61(10):3096-3101.

Samulski, et al., Helper-Free Stocks of Recombinant Adeno-Associated Viruses: Normal Integration Does Not Require Viral Gene Expression, *J Virol.* (Sep. 1989), 63(9):3822-3828.

Scanlon, Anti-Genes: siRNA, Ribozymes and Antisense, *Curr Pharm Biotechnol.* (Oct. 2004), 5(5):415-420.

Schroder, et al., A single-stranded promoter for RNA polymerase III, *Proc Natl Acad Sci USA.* (Feb. 4, 2003), 100(3):934-939.

Sewell, et al., Complement C3 and C5 play critical roles in traumatic brain cryoinjury: blocking effects on neutrophil extravasation by C5a receptor antagonist, *J Neuroimmunol.* (Oct. 2004), 155(1-2):55-63.

Shen, et al., A Study of Cobra Venom Factor in Ex Vivo Pig Liver Perfusion Model, *Transplantation Proc.* (Nov.-Dec. 2001), 33(7-8):3860-3861.

Shen, et al., Suppression of ocular neovascularization with siRNA targeting VEGF receptor 1, *Gene Ther.* (Feb. 2006), 13(3):225-234.

Shi, et al., Antisense imaging of gene expression in the brain in vivo, *Proc Natl Acad Sci USA.* (Dec. 19, 2000), 97(26):14709-14714.

Shibuya, et al., Nucleotide sequence and expression of a novel human receptor-type tyrosine kinaase gene (flt), closely related to the fms family, *Oncogene.* (Apr. 1990), 5(4):519-524 (Abstract).

Shim, et al., Inhibition of Angiopoietin-1 Expression in Tumor Cells by an Antisense RNA Approach Inhibited Xenograft Tumor Growth in Immunodeficient Mice, *Int J Cancer.* (Oct. 1, 2001), 94(1):6-15.

Shoji, et al., Current Status of Delivery Systems to Improve Target Efficacy of Oligonucleotides, *Curr Pharm Des.* (2004), 10(7):785-796.

Simeoni, et al., Peptide-Based Strategy for siRNA Delivery into Mammalian Cells, *Methods Mol. Biol.* (2005), 309:251-260.

Sioud, siRNA Delivery In Vivo, *Methods Mol Biol.* (2005), 309:237-249.

Smith, et al., Membrane-targeted complement inhibitors, *Mol Immunol.* (Aug. 2001), 38(2-3):249-255.

Smith, et al., Rational selection of antisense oligonucleotide sequences, *Eur J Pharm Sci.* (Sep. 2000), 11(3):191-198.

Sohail, et al., Selecting optimal antisense reagenets, *Adv Drug Deliv Rev.* (Oct. 31, 2000), 44(1):23-34.

Sohn, et al., Chronic Low Level Complement Activation within the Eye is Controlled by Intraocular Complement Regulatory Proteins, *Invest Ophthalmol Vis Sci.* (Oct. 2000), 41(11):3492-3502.

Sohn, et al., Complement Regulatory Activity of Normal Human Intraocular Fluid is Mediated by MCP, DAF, and CD59, *Invest Ophthalmol Vis Sci.* (Dec. 2000), 41(13):4195-4202.

Sohn, et al., Tolerance is dependent on complement C3 fragment iC3b binding to antigen-presenting Cells, *Nat Med.* (Feb. 2003), 9(2):206-212.

Songsivilai, et al., Bispecific antibody: a tool for diagnosis and treatment of disease, *Clin Exp Immunol.* (Mar. 1990), 79(3):315-321.

Spaide, et al., Intravitreal Bevacizumab Treatment of Choroidal Neovascularization Secondary to Age-Related Macular Degeneration, *Retina* (2006), 26(4):383-390.

Speidl, et al., Complement component C5a predicts future cardiovascular events in patients with advanced atherosclerosis, *Eur Heart J.* (Nov. 2005), 26(21):2294-2299.

Speirs, et al., Production of VEGF and expression of the VEGF receptors Flt-1 and KDR in primary cultures of epithelial and stromal cells derived from breast tumours, *Br J Cancer* (May 1999), 80(5-6):898-903.

Stein, et al., Oligodeoxynucleotides as Inhibitors of Gene Expression: A Review, *Cancer Res.* (May 15, 1988), 48(10):2659-2668.

Strachan, et al., A New Small Molecule C5a Receptor Antagonist Inhibits the Reverse-Passive Arthus Reaction and Endotoxic Shock in Rats, *J Immunol.* (Jun. 15, 2000), 164(12):6560-6565.

Sun, et al., Gene transfer of antisense hypoxia inducible factor-1 α enhances the therapeutic efficacy of cancer immunotherapy, *Gene Ther.* (Apr. 2001), 8(8):638-645.

Sun, et al., Prolonged cardiac xenograft survival in guinea pig-to-rat model by a highly active cobra venom factor, *Toxicon.* (Sep. 1, 2003), 42(3):257-262.

Szoka, Jr., et al., Comparitive Properties and Methods of Preparation of Lipid Vesicles (Liposomes), Ann Rev Biophys Bioeng. (Jun. 1980), 9:467-508.

Thurman, et al., A novel inhibitor of the alternative complement pathway prevents antiphospholipid antibody-induced pregnancy loss in mice, *Mol Immunol.* (Jan. 2005), 42(1):87-97.

Tischer, et al., The Human Gene for Vascular Endothelial Growth Factor. Multiple Protein Forms Are Encoded Through Alternative Exon Splicing, J Biol Chem. (Jun. 25, 1991), 266(18):11947-11954 (Abstract).

Toschi, Influence of mRNA Self-Structure on Hybridization: Computational Tools for Antisense Sequence Selection, *Methods* (Nov. 2000), 22(3):261-269.

Trudeau, et al., An Intersubunit Interaction Regulates Trafficking of Rod Cyclic Nucleotide-Gated Channels and Is Disrupted in an Inherited Form of Blindness, *Neuron.* (Apr. 11, 2002), 34(2):197-207.

Tuschl, Expanding small RNA interference, *Nat Biotechnol.* (May 2002), 20(5):446-448.

Tuschl, The siRNA user guide, http://www.mpidpc.gwdg.de/abteilungen/100/105/sirna.html (May 6, 2004).

Tuschl, The siRNA user guide, http://www.mpidpc.gwdg.de/abteilungen/100/105/sirna.html (Oct. 11, 2002).

Tyler, et al., Peptide nucleic acids targeted to the neurotensin receptor and administered i.p. cross the blood-brain barrier and specifically reduce gene expression, *Proc Natl Acad Sci USA.* (Jun. 8, 1999), 96(12):7053-7058.

Van Brunt, Shoot the Messenger, Signals Magazine, http://www.signalsmag.com/signalsmag/3DF5AEF6049CC81C99256C1D0055BAA (Aug. 22, 2002).

Van Der Krol, et al., Modulation of Eukaryotic Gene Expression by Complementary RNA or DNA Sequences, *BioTechniques.* (Nov.-Dec. 1988), 6(10):958-976.

Verma, et al., Gene therapy—promises, problems and prospects, *Nature.* (Sep. 18, 1997), 389(6648):239-242.

Verma, et al., Gene Therapy: Twenty-First Century Medicine, *Annu Rev Biochem.* (2005), 74:711-738.

Vickers, et al., Efficient Reduction of Target RNAs by Small Interfering RNA and RNase H-dependent Antisense Agents, *J Biol Chem.* (Feb. 28, 2003), 278(9):7108-7118.

Vogel, et al., Recombinant cobra venom factor, *Mol. Immunol.* (Jun. 2004), 41(2-3):191-199.

Walport, Complement at the Interface Between Innate and Adaptive Immunity, Complement, First of Two Parts, *N Engl J Med.* (Apr. 12, 2001), 344(14):1058-1066.

Walport, Complement at the Interface Between Innate and Adaptive Immunity, Complement: Second of Two Parts, *N Engl J Med.* (Apr. 12, 2001), 344(15):1140-1144.

Ward, et al., Genomic structure of the human angiopoietins show polymorphism in angiopoietin-2, *Cytogenet Cell Genet.* (2001), 94(3-4):147-154.

Warren, et al., Successful ICAM-1 Gene Inactivation in Pluripotent Stem Cell using RNA Interference and in Situ Expressed Antisense/Ribozyme Transgenes, *J Am Soc Nephrology* (2002), p. 101A (Abstract).

Weber, et al., Genomic organization and complete sequence of the human gene encoding the β-subunit of the cGMP phosphodiesterase and its localisation to 4p16.3, *Nucleic Acids Res.*, (Nov. 25, 1991), 19(22):6263-6268.

Wu, et al., Pharmokinetics and Blood-Brain Barrier Transport of [$^3$H]-Biotinylated Phosphorothioate Oligodeaoxynucleotide Conjugated to a Vector-Mediated Drug Delivery System, *J Pharmacol Exp Ther.* (Jan. 1996), 276(1):206-211.

Xia, et al., siRNA-mediated gene silencing in vitro and in vivo, *Nat Biotechnol.* (Oct. 2002), 20(10):1006-1010.

Xu, et al., Protective effect of membrane cofactor protein against complement-dependent injury, *Acta Pharmacol. Sin.* (Aug. 2005), 26(8):987-991.

Zamore, et al., RNAi: double-stranded RNA directs the ATP-dependent cleavage of mRNA at 21 to 23 nucleotide intervals, *Cell* (Mar. 31, 2000), 101:25-33.

Zareparsi, et al., Strong Association of the Y402H Variant in Complement Factor H at 1q32 with Susceptibility to Age-Related Macular Degeneration, *Am J Hum Genet.* (Jul. 2005), 77(1):149-153.

Zheng, et al., Protection of Renal Ischemia Injury Using Combination Gene Silencing of Complement 3 and Caspase 3 Genes, *Transplantation* (Dec. 27, 2006), 82(12):1781-1786.

Harper et al., "VEGF-A Splicing: The Key to Anti-Angiogenic Therapeutics?", *Nat. Rev. Cancer* (Nov. 2008), 8(11):880-887.

\* cited by examiner

```
                              Exon 7/8 boundry
nt        518
VEGF 165  Aaggcgaggcagcttgagttaaacgaacgtacttgcagatgcagatgtgacaagccgaggcggtga
VEGF 165B Aaggcgaggcagcttgagttaaacgaacgtacttgcag--------------------------

VEGF 165  gccgggcaggaggaggagccteccteagggtttcgggaaccagatctctcaccaggaaa    SEQ ID NO: 3
VEGF 165B ---------------------------------------atctctcaccaggaaa          SEQ ID NO: 127

VEGF 165  gactgatacagaacgatcgatacagaaaccac
VEGF 165B gactgatacagaacgatcgatacagaaaccac
```

Fig. 11

Cytokine Profile of ARPE19 Cells Following Treatment with siRNAs

| Cytokine | Poly I:C | Bevasiranib | OPK-HVB-004 | OPK-HVB-010 | OPK-HVB-009 | OPK-HVB-012 |
|---|---|---|---|---|---|---|
| IFN-α | - | - | - | - | - | - |
| IFN-β | - | - | - | - | - | - |
| IFN-γ | - | - | - | - | - | - |
| IL-8 | + | - | + | - | - | + |
| IL-6 | + | + | + | - | - | + |
| TNFα | + | - | - | - | - | - |
| ICAM | + | - | - | - | - | - |
| IL-12 | - | - | - | - | - | - |
| MCP-1 | + | - | + | - | - | + |

Fig. 23

OPK-HVB-009 Dose Response (5 nM-50nM)-Knockdown of Total VEGF Protein Secreted by ARPE19 (% Knockdown Relative to Ribojuice Treated Control)

OPK-HVB (21-mer) Dose Response (250 pM–25nM)-Knockdown of Total VEGF Secreted by ARPE19 (% Knockdown Relative to Ribojuice Treated Control)

Percent Knockdown of hVEGF Secreted by ARPE19 Cells – Stability Study of Bevasiranib (25 nM) Under Different Temperature Conditions (Weeks 1-4)

Percent Knockdown of hVEGF Secreted by ARPE19 Cells – Stability Study of Bevasiranib (25 nM) Under Different Temperature Conditions (Weeks 5-8)

Percent Knockdown of hVEGF Secreted by ARPE19 Cells – Stability Study of OPK-HVB-004 (25 nM) Under Different Temperature Conditions (24 hours-4 weeks)

Percent Knockdown of hVEGF Secreted by ARPE19 Cells – Stability Study of OPK-HVB-009 (25 nM) Under Different Temperature Conditions (24 hours-4 weeks)

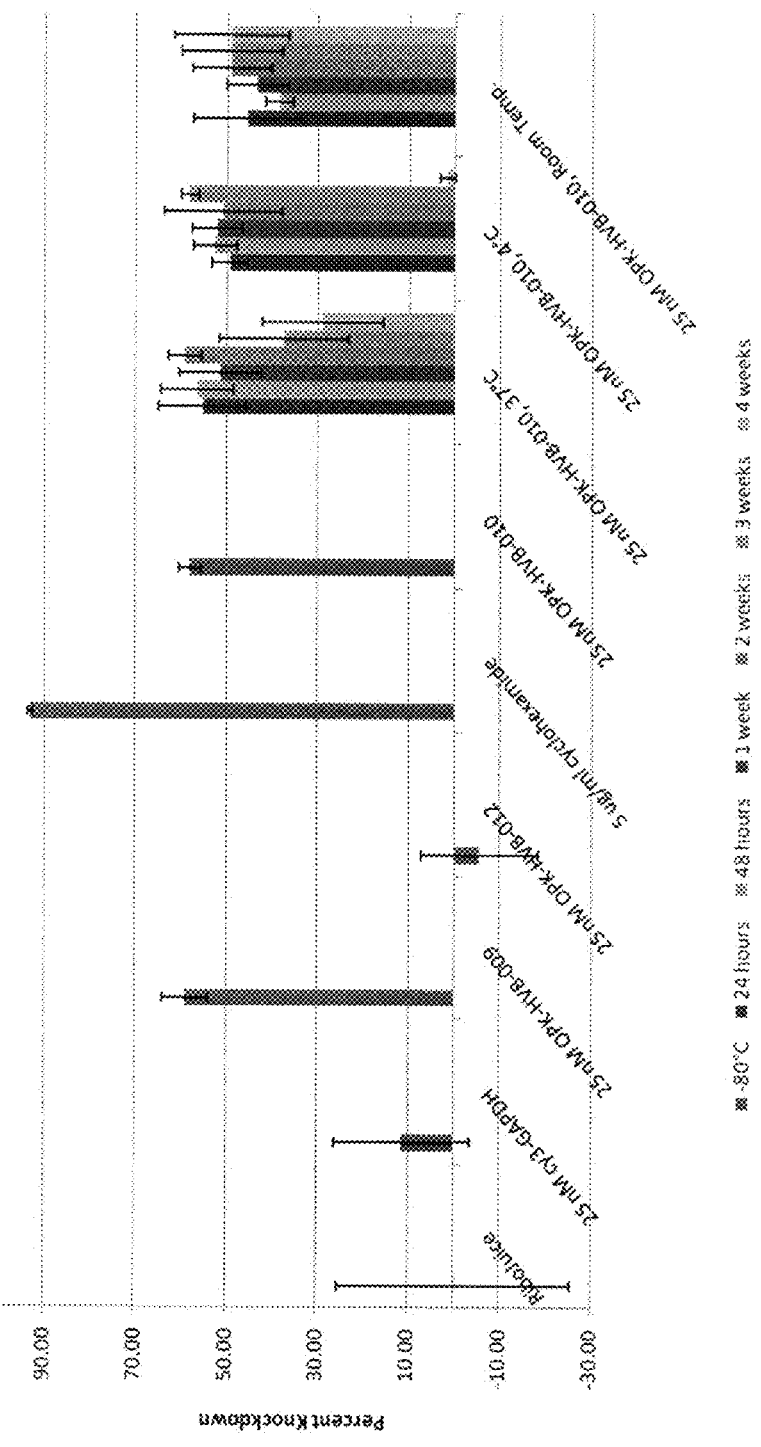

Figure 33

Homology between terminal codons encoding human, mouse and rat VEGF

```
Human  gaacgtactt gcaga tgt gac aag ccg agg cgg tga
                         C   D   K   P   R   R
                         Cys Asp Lys Pro Arg Arg          SEQ ID NO: 3
                  nt641

Rat    gaacgtactt gcaga tgt gac aag ccg agg cgg tga
                         C   D   K   P   R   R
                         Cys Asp Lys Pro Arg Arg          SEQ ID NO: 130
                                                          SEQ ID NO: 128

Mouse  gaacgtactt gcaga tgt gac aag ccg agg cgg tga
                         C   D   K   P   R   R
                         Cys Asp Lys Pro Arg Arg          SEQ ID NO: 129
                                                          SEQ ID NO: 130
```

| siRNA | Target Sequence | |
|---|---|---|
| OPK-HVB-004 | GTACTTGCAGATGTGACAA | SEQ ID NO: 88 |
| OPK-HVB-009 | TGCAGATGTGACAAGCC▓A | SEQ ID NO: 93 |
| OPK-HVB-010 | GCAGATGTGACAAGCC▓AG | SEQ ID NO: 94 |
| OPK-HVB-012 | AGATGTGACAAGC▓AGGC | SEQ ID NO: 96 |

% Knockdown of Rat VEGF Secreted by C6 Cells with OPK-HVB (21mer) siRNAs Relative to Ribojuice Control – Dose Response (250pm-25nM)

% Knockdown of Mouse VEGF Secreted by NIH3T3 Cells with OPK-HVB (21mer) siRNAs (25nM) Relative to Lipofectamine 2000 Control Effect of OPK-HVB siRNAs on % hVEGF Knockdown in ARPE19 Cells-21mer (19+dTdT) vs 19mer (blunt end counterpart)

Preliminary siRNA Screen: Effect of OPK-HVB (19mer; 17bp +dTdT) siRNAs (25nM) on Knockdown of Total VEGF Protein in ARPE19 (% Knockdown Relative to Ribojuice Treated Control)

Dose Response Expt.- Percent Knockdown of hVEGF Secreted by ARPE19 Cells Transfected with 19mer-be and 19mer (17bp+dTdT) siRNAs

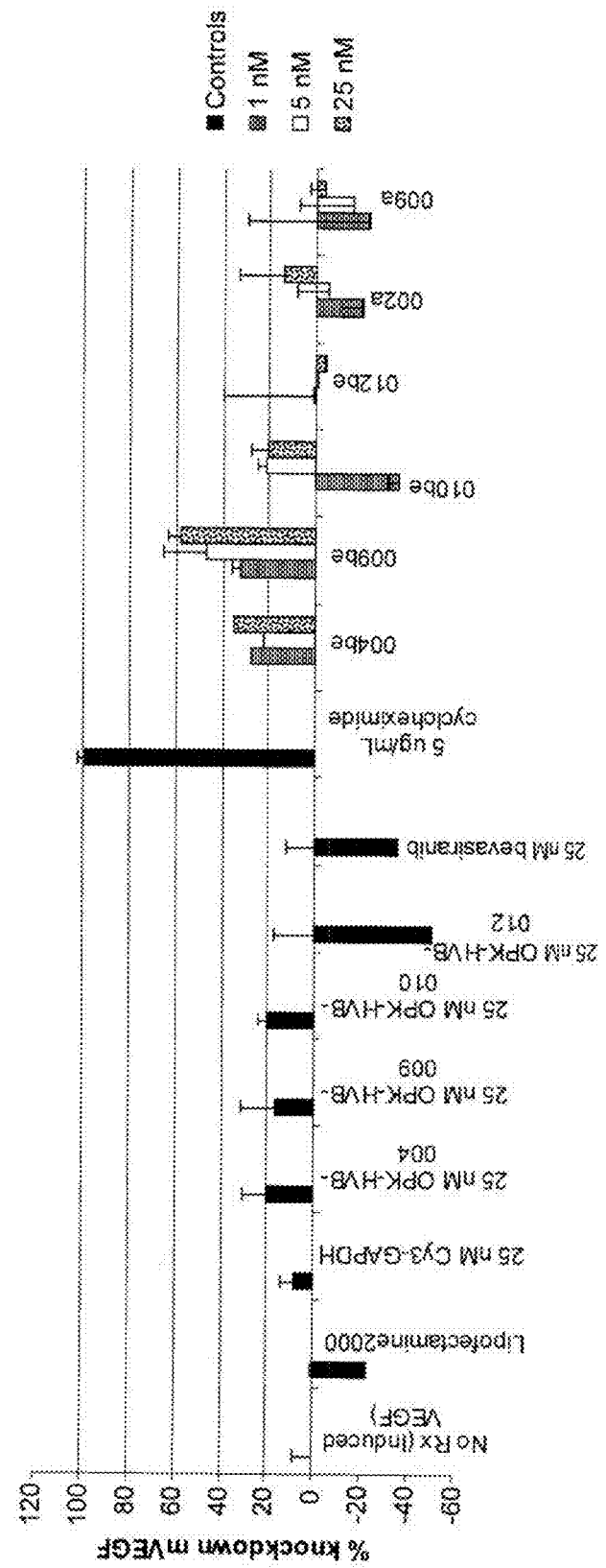

SEQUENCE LISTING

<160> NUMBER OF SEQ ID NOS: 138

<210> SEQ ID NO 1
<211> LENGTH: 2250
<212> TYPE: DNA
<213> ORGANISM: Mus musculus

<400> SEQUENCE: 1

```
tgagccaggc tggcaggaag gagcctccct cagggtttcg ggaaccagac ctctcaccgg      60
aaagaccgat taaccatgtc accaccacgc catcatcgtc accgttgaca gaacagtcct     120
taatccagaa agcctgacat gaaggaagag gagactcttc gaggagcact ttgggtccgg     180
agggcgagac tccggcagac gcattcccgg gcaggtgacc aagcacggtc cctcgtggga     240
ctggattcgc cattttctta tatctgctgc taaatcgcca agcccggaag attagggttg     300
tttctgggat tcctgtagac acacccaccc acatacacac atatatatat attatatata     360
taaataaata tatatgtttt atatataaaa tatatatata ttctttttt taaattaact      420 ctgctaatgt tattggtgtc ttcactggat atgtttgact gctgtggact tgtgttggga     480
ggaggatgtc ctcactcgga tgccgacatg ggagacaatg ggatgaaagg cttcagtgtg     540
gtctgagaga ggccgaagtc cttttgcctg ccggggagca agcaaggcca gggcacgggg     600
gcacattggc tcacttccag aaacacgaca aacccattcc tggccctgag tcaagaggac     660
agagagacag atgatgacac agaaagagat aaagatgccg gttccaacca gaagtttggg     720
gagcctcagg acatggcatg cttttgtggat ccccatgata gtctacaaaa gcaccccgcc     780
cctctgggca ctgcctggaa gaatcgggag cctggccagc cttcagctcg ctcctccact     840
tctgaggggc ctaggaggcc tcccacaggt gtcccggcaa gagaagacac ggtggtggaa     900
gaagaggcct ggtaatggcc cctcctcctg ggaccccttc gtcctctcct tacccccacct    960 cctgggtaca gcccaggagg accttgtgtg atcagaccat tgaaaccact aattctgtcc    1020
ccaggagact tggctctgtg tgtgagtggc ttacccttcc tcatcttccc ttcccaaggc    1080
acagagcaat ggggcaggac ccgcaagccc ctcacgagg cagagaaaag agaaagtgtt    1140
ttatatacgg tacttattta atagcccttt ttaattagaa attaaaacag ttaatttaat    1200
taaagagtag ggttttttc agtattcttg gttaatattt aatttcaact atttatgaga    1260
tgtatctctc gctctctctt atttgtactt atgtgtgtgt gtgtgtgtgt gtgtgtgtgt    1320
gtgtgtgtgt gtatgaaatc tgtgtttcca atctctctct cccagatcgg tgacagtcac    1380
tagcttgtcc tgagaagata tttaatttg ctaacactca gctctgccct cccttgtccc    1440
caccacacat tccttttgaaa taaggtttca atatacattt acatactata tatatattg     1500 gcaacttgtg tttgtatata aatatatata tatatatatg tttatgtata tatgtgattc    1560
tgataaaata gacattgcta ttctgtttt tatatgtaaa aacaaaacaa gaaaatataga     1620 gaattctaca tactaaatct ctctcctttt ttaatttaa tatttgttat catttattta     1680
ttggtgctac tgtttatccg taataattgt gggggaaaaa gatattaaca tcacgtcttt     1740
gtctctagag cagttttccg agatattccg tagtacatat ttatttttaa acagcaacaa    1800
agaaatacag atatatctta aaaaaaaagc attttgtatt aaagaattga attctgatct    1860
caaagctctc cctggtctct ccttctctcc tgggccctcc tgtctcgctt tccctcctcc    1920
```

```
tttggggtac atagttttg tcttaggttt gagaagcagt ccctggagta gaatatgggg      1980
tgacccatcc attcctgggc ggaggggaga tggctccttt gccaagggtc ctcacactac      2040
gtggtactct gttccttgtc agacaaggat gggggcatgt ctccaggtgc taactggaga      2100
tcggagagag ctgttggctg cagctggcca ggatttgggc atgccgggga catgggaggc      2160
tgtgagccca gcatgcagtt tacttctggg tgctaaatgg aagagtccag taaaaagagt      2220
cttgcccatg ggattccatt ccgctttgtg                                       2250

<210> SEQ ID NO 2
<211> LENGTH: 444
<212> TYPE: DNA
<213> ORGANISM: Homo sapiens

<400> SEQUENCE: 2
atgaactttc tgctgtcttg ggtgcattgg agccttgcct tgctgctcta cctccaccat       60
gccaagtggt cccaggctgc acccatggca gaaggaggag ggcagaatca tcacgaagtg      120
gtgaagttca tggatgtcta tcagcgcagc tactgccatc caatcgagac cctggtggac      180
atcttccagg agtaccctga tgagatcgag tacatcttca gccatcctg tgtgcccctg       240 atgcgatgcg ggggctgctg caatgacgag ggcctggagt gtgtgcccac tgaggagtcc      300
aacatcacca tgcagattat gcggatcaaa cctcaccaag gccagcacat aggagagatg      360
agcttcctac agcacaacaa atgtgaatgc agaccaaaga agatagagc aagacaagaa      420 aaatgtgaca agccgaggcg gtga                                              444

<210> SEQ ID NO 3
<211> LENGTH: 576
<212> TYPE: DNA
<213> ORGANISM: Homo sapiens

<400> SEQUENCE: 3
atgaactttc tgctgtcttg ggtgcattgg agccttgcct tgctgctcta cctccaccat       60
gccaagtggt cccaggctgc acccatggca gaaggaggag ggcagaatca tcacgaagtg      120
gtgaagttca tggatgtcta tcagcgcagc tactgccatc caatcgagac cctggtggac      180
atcttccagg agtaccctga tgagatcgag tacatcttca gccatcctg tgtgcccctg       240 atgcgatgcg ggggctgctg caatgacgag ggcctggagt gtgtgcccac tgaggagtcc      300
aacatcacca tgcagattat gcggatcaaa cctcaccaag gccagcacat aggagagatg      360
agcttcctac agcacaacaa atgtgaatgc agaccaaaga agatagagc aagacaagaa      420 aatccctgtg ggccttgctc agagcggaga agcatttgt ttgtacaaga tccgcagacg      480
tgtaaatgtt cctgcaaaaa cacagactcg cgttgcaagg cgaggcagct tgagttaaac      540
gaacgtactt gcagatgtga caagccgagg cggtga                                 576

<210> SEQ ID NO 4
<211> LENGTH: 648
<212> TYPE: DNA
<213> ORGANISM: Homo sapiens

<400> SEQUENCE: 4
atgaactttc tgctgtcttg ggtgcattgg agccttgcct tgctgctcta cctccaccat       60
gccaagtggt cccaggctgc acccatggca gaaggaggag ggcagaatca tcacgaagtg      120
gtgaagttca tggatgtcta tcagcgcagc tactgccatc caatcgagac cctggtggac      180
atcttccagg agtaccctga tgagatcgag tacatcttca gccatcctg tgtgcccctg       240
```

-continued

```
atgcgatgcg ggggctgctg caatgacgag ggcctggagt gtgtgcccac tgaggagtcc    300
aacatcacca tgcagattat gcggatcaaa cctcaccaag gccagcacat aggagagatg    360
agcttcctac agcacaacaa atgtgaatgc agaccaaaga aagatagagc aagacaagaa    420
aaaaaatcag ttcgaggaaa gggaaagggg caaaaacgaa agcgcaagaa atcccggtat    480
aagtcctgga gcgttccctg tgggccttgc tcagagcgga gaaagcattt gtttgtacaa    540
gatccgcaga cgtgtaaatg ttcctgcaaa aacacagact cgcgttgcaa ggcgaggcag    600
cttgagttaa acgaacgtac ttgcagatgt gacaagccga ggcggtga                 648
```

<210> SEQ ID NO 5
<211> LENGTH: 670
<212> TYPE: DNA
<213> ORGANISM: Homo sapiens

<400> SEQUENCE: 5

```
gccttgctgc tctacctcca ccatgccaag tggtcccagg ctgcacccat ggcagaagga     60
ggagggcaga atcatcacga agtggtgaag ttcatggatg tctatcagcg cagctactgc    120
catccaatcg agaccctggt ggacatcttc caggagtacc ctgatgagat cgagtacatc    180
ttcaagccat cctgtgtgcc cctgatgcga tgcgggggct gctgcaatga cgagggcctg    240
gagtgtgtgc ccactgagga gtccaacatc accatgcaga ttatgcggat caaacctcac    300
caaggccagc acataggaga gatgagcttc ctacagcaca caaatgtga atgcagacca    360 aagaaggata gagcaagaca agaaaaaaaa tcagttcgag gaaagggaaa ggggcaaaaa    420
cgaaagcgca agaaatcccg gtataagtcc tggagcgttt acgttggtgc cgctgctgt    480 ctaatgccct ggagcctccc tggcccccat ccctgtgggc cttgctcaga gcggagaaag    540
catttgtttg tacaagatcc gcagacgtgt aaatgttcct gcaaaaacac agactcgcgt    600
tgcaaggcga ggcagcttga gttaaacgaa cgtacttgca gatgtgacaa gccgaggcgg    660
tgatgaatga                                                          670
```

<210> SEQ ID NO 6
<211> LENGTH: 1137
<212> TYPE: DNA
<213> ORGANISM: Homo sapiens

<400> SEQUENCE: 6

```
atgctcattg tccagactgg ggtcagatca gcaaacaaag ggcctctgat ggtgattgtt     60
gaatattgca aatatggaaa tctatccaac tacctcaaga gcaaatatga cttattttt    120 ctcgacaagg atgtggcatc acacatggag cgtaagaaag aaaaaatgga gccaggcctg    180
gaacaaggca agaaaccaaa actagatagc atcaccagca gcgagagctt tgggagctcc    240
aagtttcagg aagataaaaa tctgagtgat gttgaggaag aggaggattc tgatggtttc    300
taccaggagc ccatcactat ggaagatctg atttcttaca gttttcaagt ggccagaggc    360
atgaagtttc tgtcttccag aaagtgcatt cattgggacc tggcagcaag aaacattctt    420
ttatctgaga caatgtggt gaagatttgt gattttggcc ttgcccagga tatttacaag    480
aacgccgatt atgtgagaaa aggaggtggg tctccatacc caggagtgca aatggatgag    540
cacttctgca gttgcctgag ggaaggcatg aggatgagag ctgctgagta ctccactcct    600
gaaatctatc agatcatgct ggactgcagg cacaaagacc caaagaaag gccaagattt    660 gcagaacttg tggaaaaact agaaaatagt gggtttacat actcaactcc tgccttctct    720
gaggacttct tcaaggaagg tatttcagct cccaagttta gttcaggaag ctctgatgat    780
```

```
gtcagatacg taaatgcttt caagttcatg agcctggaaa gaatcaaaac ctttgaagaa    840
cttttgccaa atgccacctc catgtttgat gactaccagg gggacagcag cgctctgctg    900
gcctctccca tgctgaagcg cttcaccagg actgacagca aacccaaggc ctcgctcaag    960
attgacttga gactaactag caaaagtaag aagtcggggc tttctgatgt cagcaggccc   1020
agtttctgcc attccaacag tgggcacatc agcaaaggca agggcaggtt cacctacgac   1080
aacgccgagc tggaaaggaa gacggcgtgc tgctccccgc ccctctggga gttgtag      1137

<210> SEQ ID NO 7
<211> LENGTH: 5830
<212> TYPE: DNA
<213> ORGANISM: Homo sapiens

<400> SEQUENCE: 7
actgagtccc gggaccccgg gagagcggtc agtgtgtggt cgctgcgttt cctctgcctg     60
cgccgggcat cacttgcgcg ccgcagaaag tccgtctggc agcctggata tcctctccta    120
ccggcacccg cagacgcccc tgcagccgcc ggtcggcgcc cgggctccct agccctgtgc    180
gctcaactgt cctgcgctgc ggggtgccgc gagttccacc tccgcgcctc cttctctaga    240
caggcgctgg gagaaagaac cggctcccga gttctgggca tttcgcccgg ctcgaggtgc    300
aggatgcaga gcaaggtgct gctggccgtc gccctgtggc tctgcgtgga gacccgggcc    360
gcctctgtgg gtttgcctag tgtttctctt gatctgccca ggctcagcat acaaaaagac    420
atacttacaa ttaaggctaa tacaactctt caaattactt gcaggggaca gagggacttg    480
gactggcttt ggcccaataa tcagagtggc agtgagcaaa gggtggaggt gactgagtgc    540
agcgatggcc tcttctgtaa gacactcaca attccaaaag tgatcggaaa tgacactgga    600
gcctacaagt gcttctaccg ggaaactgac ttggcctcgg tcatttatgt ctatgttcaa    660
gattacagat ctccatttat tgcttctgtt agtgaccaac atggagtcgt gtacattact    720
gagaacaaaa acaaaactgt ggtgattcca tgtctcgggt ccatttcaaa tctcaacgtg    780
tcactttgtg caagataccc agaaaagaga tttgttcctg atggtaacag aatttcctgg    840
gacagcaaga agggctttac tattcccagc tacatgatca gctatgctgg catggtcttc    900
tgtgaagcaa aaattaatga tgaaagttac cagtctatta tgtacatagt tgtcgttgta    960
gggtatagga tttatgatgt ggttctgagt ccgtctcatg gaattgaact atctgttgga   1020
gaaaagcttg tcttaaattg tacagcaaga actgaactaa atgtggggat tgacttcaac   1080
tgggaatacc cttcttcgaa gcatcagcat aagaaacttg taaaccgaga cctaaaaacc   1140
cagtctggga gtgagatgaa gaaattttg agcaccttaa ctatagatgg tgtaaccccgg   1200 agtgaccaag gattgtacac ctgtgcagca tccagtgggc tgatgaccaa gaagaacagc   1260
acatttgtca gggtccatga aaaccttttt gttgcttttg gaagtggcat ggaatctctg   1320
gtggaagcca cggtggggga gcgtgtcaga atccctgcga agtaccttgg ttacccaccc   1380
ccagaaataa aatggtataa aaatggaata ccccttgagt ccaatcacac aattaaagcg   1440
gggcatgtac tgacgattat ggaagtgagt gaaagagaca caggaaatta cactgtcatc   1500
cttaccaatc ccatttcaaa ggagaagcag agccatgtgg tctctctggt tgtgtatgtc   1560
ccaccccaga ttggtgagaa atctctaatc tctcctgtgg attcctacca gtacggcacc   1620
actcaaacgc tgcatatgta cggtctatgc cattcctccc cgcatcacat ccactggtat   1680
tggcagttgg aggaagagtg cgccaacgag cccagccaag ctgtctcagt gacaaaccca   1740
tacccttgtg aagaatggag aagtgtggag gacttccagg gaggaaataa aattgaagtt   1800
```

```
aataaaaatc aatttgctct aattgaagga aaaaacaaaa ctgtaagtac ccttgttatc    1860
caagcggcaa atgtgtcagc tttgtacaaa tgtgaagcgg tcaacaaagt cgggagagga    1920
gagagggtga tctccttcca cgtgaccagg ggtcctgaaa ttactttgca acctgacatg    1980
cagcccactg agcaggagag cgtgtctttg tggtgcactg cagacagatc tacgtttgag    2040
aacctcacat ggtacaagct tggcccacag cctctgccaa tccatgtggg agagttgccc    2100
acacctgttt gcaagaactt ggatactctt tggaaattga atgccaccat gttctctaat    2160
agcacaaatg acattttgat catggagctt aagaatgcat ccttgcagga ccaaggagac    2220
tatgtctgcc ttgctcaaga caggaagacc aagaaaagac attgcgtggt caggcagctc    2280
acagtcctag agcgtgtggc acccacgatc acaggaaacc tggagaatca gacgacaagt    2340 attgggaaa gcatcgaagt ctcatgcacg gcatctggga atcccctcc acagatcatg     2400 tggtttaaag ataatgagac ccttgtagaa gactcaggca ttgtattgaa ggatgggaac    2460
cggaacctca ctatccgcag agtgaggaag gaggacgaag gcctctacac ctgccaggca    2520
tgcagtgttc ttggctgtgc aaaagtggag gcattttca taatagaagg tgcccaggaa    2580
aagacgaact tggaaatcat tattctagta ggcacggcgg tgattgccat gttcttctgg    2640
ctacttcttg tcatcatcct acggaccgtt aagcgggcca atggagggga actgaagaca    2700
ggctacttgt ccatcgtcat ggatccagat gaactcccat ggatgaaaca ttgtgaacga    2760
ctgccttatg atgccagcaa atgggaattc cccagagacc ggctgaagct aggtaagcct    2820
cttggccgtg gtgcctttgg ccaagtgatt gaagcagatg cctttggaat tgacaagaca    2880
gcaacttgca ggacagtagc agtcaaaatg ttgaaagaag gagcaacaca cagtgagcat    2940
cgagctctca tgtctgaact caagatcctc attcatattg gtcaccatct caatgtggtc    3000
aaccttctag gtgcctgtac aagccagga gggccactca tggtgattgt ggaattctgc    3060
aaatttggaa acctgtccac ttacctgagg agcaagagaa atgaatttgt ccctacaag    3120 accaaagggg cacgattccg tcaagggaaa gactacgttg gagcaatccc tgtggatctg    3180
aaacggcgct tggacagcat caccagtagc cagagctcag ccagtctggg atttgtggag    3240
gagaagtccc tcagtgatgt agaagaagag gaagctcctg aagatctgta taaggacttc    3300
ctgaccttgg agcatctcat ctgttacagc ttccaagtgg ctaagggcat ggagttcttg    3360
gcatcgcgaa agtgtatcca cagggacctg gcggcacgaa atatcctctt atcggagaag    3420
aacgtggtta aaatctgtga ctttggcttg gcccgggata tttataaaga tccagattat    3480
gtcagaaaag gagatgctcg cctcccttg aaatggatgg ccccagaaac aattttgac     3540 agagtgtaca caatccagag tgacgtctgg tcttttggtg ttttgctgtg ggaaatattt    3600
tccttaggtg cttctccata tcctggggta aagattgatg aagaattttg taggcgattg    3660
aaagaaggaa ctagaatgag ggcccctgat tatactacac cagaaatgta ccagaccatg    3720
ctggactgct ggcacgggga gcccagtcag agacccacgt tttcagagtt ggtggaacat    3780
ttgggaaatc tcttgcaagc taatgctcag caggatggca agactacat tgttcttccg     3840 atatcagaga ctttgagcat ggaagaggat tctggactct ctctgcctac ctcacctgtt    3900
tcctgtatgg aggaggaga agtatgtgac cccaaattcc attatgacaa cacagcagga    3960
atcagtcagt atctgcagaa cagtaagcga aagagccggc ctgtgagtgt aaaaacattt    4020
gaagatatcc cgttagaaga accagaagta aaagtaatcc cagatgacaa ccagacggac    4080
agtggtatgg ttcttgcctc agaagagctg aaaactttgg aagacagaac caaattatct    4140
ccatcttttg gtggaatggt gcccagcaaa agcagggagt ctgtggcatc tgaaggctca    4200
```

```
aaccagacaa gcggctacca gtccggatat cactccgatg acacagacac caccgtgtac    4260
tccagtgagg aagcagaact tttaaagctg atagagattg gagtgcaaac cggtagcaca    4320
gcccagattc tccagcctga ctcggggacc acactgagct ctcctcctgt ttaaaaggaa    4380
gcatccacac cccaactccc ggacatcaca tgagaggtct gctcagattt tgaagtgttg    4440
ttctttccac cagcaggaag tagccgcatt tgattttcat ttcgacaaca gaaaaaggac    4500
ctcggactgc agggagccag tcttctaggc atatcctgga agaggcttgt gacccaagaa    4560
tgtgtctgtg tcttctccca gtgttgacct gatcctcttt tttcattcat ttaaaaagca    4620
ttatcatgcc cctgctgcgg gtctcaccat gggtttagaa caaagagctt caagcaatgg    4680
ccccatcctc aaagaagtag cagtacctgg ggagctgaca cttctgtaaa actagaagat    4740
aaaccaggca acgtaagtgt tcgaggtgtt gaagatggga aggatttgca gggctgagtc    4800
tatccaagag gctttgttta ggacgtgggt cccaagccaa gccttaagtg tggaattcgg    4860
attgatagaa aggaagacta acgttacctt gctttggaga gtactggagc ctgcaaatgc    4920
attgtgtttg ctctggtgga ggtgggcatg gggtctgttc tgaaatgtaa agggttcaga    4980
cggggtttct ggttttagaa ggttgcgtgt tcttcgagtt gggctaaagt agagttcgtt    5040
gtgctgtttc tgactcctaa tgagagttcc ttccagaccg ttagctgtct ccttgccaag    5100
ccccaggaag aaaatgatgc agctctggct ccttgtctcc caggctgatc ctttattcag    5160
aataccacaa agaaaggaca ttcagctcaa ggctccctgc cgtgttgaag agttctgact    5220
gcacaaacca gcttctggtt tcttctggaa tgaatacccct catatctgtc ctgatgtgat    5280
atgtctgaga ctgaatgcgg gaggttcaat gtgaagctgt gtgtggtgtc aaagtttcag    5340
gaaggatttt acccttttgt tcttccccct gtccccaacc cactctcacc ccgcaaccca    5400
tcagtatttt agttatttgg cctctactcc agtaaacctg attgggtttg ttcactctct    5460
gaatgattat tagccagact tcaaaattat tttatagccc aaattataac atctattgta    5520
ttatttagac ttttaacata tagagctatt tctactgatt tttgcccttg ttctgtcctt    5580
tttttcaaaa aagaaaatgt gttttttgtt tggtaccata gtgtgaaatg ctgggaacaa    5640
tgactataag acatgctatg gcacatatat ttatagtctg tttatgtaga aacaaatgta    5700
atatattaaa gccttatata taatgaactt tgtactattc acattttgta tcagtattat    5760
gtagcataac aaaggtcata atgctttcag caattgatgt catttttatta aagaacattg    5820 aaaaacttga                                                          5830
```

<210> SEQ ID NO 8
<211> LENGTH: 19
<212> TYPE: DNA
<213> ORGANISM: Homo sapiens

<400> SEQUENCE: 8
tcatcacgaa gtggtgaag                                                 19

<210> SEQ ID NO 9
<211> LENGTH: 21
<212> TYPE: RNA
<213> ORGANISM: Homo sapiens

<400> SEQUENCE: 9
ucaucacgaa guggugaagu u                                              21

<210> SEQ ID NO 10
<211> LENGTH: 21

```
<212> TYPE: RNA
<213> ORGANISM: Homo sapiens

<400> SEQUENCE: 10
uuaguagugc uucaccacuu c                                              21

<210> SEQ ID NO 11
<211> LENGTH: 21
<212> TYPE: DNA
<213> ORGANISM: Artificial Sequence
<220> FEATURE:
<223> OTHER INFORMATION: synthesized

<400> SEQUENCE: 11
ucaucacgaa guggugaagt t                                              21

<210> SEQ ID NO 12
<211> LENGTH: 21
<212> TYPE: DNA
<213> ORGANISM: Artificial Sequence
<220> FEATURE:
<223> OTHER INFORMATION: synthesized

<400> SEQUENCE: 12
ttaguagugc uucaccacuu c                                              21

<210> SEQ ID NO 13
<211> LENGTH: 21
<212> TYPE: DNA
<213> ORGANISM: Homo sapiens

<400> SEQUENCE: 13
aacgtacttg cagatgtgac a                                              21

<210> SEQ ID NO 14
<211> LENGTH: 19
<212> TYPE: DNA
<213> ORGANISM: Homo sapiens

<400> SEQUENCE: 14
gttcatggat gtctatcag                                                 19

<210> SEQ ID NO 15
<211> LENGTH: 19
<212> TYPE: DNA
<213> ORGANISM: Homo sapiens

<400> SEQUENCE: 15
tcgagaccct ggtggacat                                                 19

<210> SEQ ID NO 16
<211> LENGTH: 19
<212> TYPE: DNA
<213> ORGANISM: Homo sapiens

<400> SEQUENCE: 16
tgacgagggc ctggagtgt                                                 19

<210> SEQ ID NO 17
<211> LENGTH: 19
<212> TYPE: DNA
<213> ORGANISM: Homo sapiens

<400> SEQUENCE: 17
tgacgagggc ctggagtgt                                                 19
```

```
<210> SEQ ID NO 18
<211> LENGTH: 19
<212> TYPE: DNA
<213> ORGANISM: Homo sapiens

<400> SEQUENCE: 18
catcaccatg cagattatg                                                  19

<210> SEQ ID NO 19
<211> LENGTH: 19
<212> TYPE: DNA
<213> ORGANISM: Homo sapiens

<400> SEQUENCE: 19
acctcaccaa ggccagcac                                                  19

<210> SEQ ID NO 20
<211> LENGTH: 19
<212> TYPE: DNA
<213> ORGANISM: Homo sapiens

<400> SEQUENCE: 20
ggccagcaca taggagaga                                                  19

<210> SEQ ID NO 21
<211> LENGTH: 19
<212> TYPE: DNA
<213> ORGANISM: Homo sapiens

<400> SEQUENCE: 21
caaatgtgaa tgcagacca                                                  19

<210> SEQ ID NO 22
<211> LENGTH: 19
<212> TYPE: DNA
<213> ORGANISM: Homo sapiens

<400> SEQUENCE: 22
atgtgaatgc agaccaaag                                                  19

<210> SEQ ID NO 23
<211> LENGTH: 19
<212> TYPE: DNA
<213> ORGANISM: Homo sapiens

<400> SEQUENCE: 23
tgcagaccaa agaaagata                                                  19

<210> SEQ ID NO 24
<211> LENGTH: 19
<212> TYPE: DNA
<213> ORGANISM: Homo sapiens

<400> SEQUENCE: 24
agaaagatag agcaagaca                                                  19

<210> SEQ ID NO 25
<211> LENGTH: 19
<212> TYPE: DNA
<213> ORGANISM: Homo sapiens

<400> SEQUENCE: 25
gaaagataga gcaagacaa                                                  19
```

```
<210> SEQ ID NO 26
<211> LENGTH: 19
<212> TYPE: DNA
<213> ORGANISM: Homo sapiens

<400> SEQUENCE: 26
gatagagcaa gacaagaaa                                               19

<210> SEQ ID NO 27
<211> LENGTH: 19
<212> TYPE: DNA
<213> ORGANISM: Homo sapiens

<400> SEQUENCE: 27
gacaagaaaa tccctgtgg                                               19

<210> SEQ ID NO 28
<211> LENGTH: 19
<212> TYPE: DNA
<213> ORGANISM: Homo sapiens

<400> SEQUENCE: 28
gaaaatccct gtgggcctt                                               19

<210> SEQ ID NO 29
<211> LENGTH: 19
<212> TYPE: DNA
<213> ORGANISM: Homo sapiens

<400> SEQUENCE: 29
aatccctgtg ggccttgct                                               19

<210> SEQ ID NO 30
<211> LENGTH: 19
<212> TYPE: DNA
<213> ORGANISM: Homo sapiens

<400> SEQUENCE: 30
tccctgtggg ccttgctca                                               19

<210> SEQ ID NO 31
<211> LENGTH: 19
<212> TYPE: DNA
<213> ORGANISM: Homo sapiens

<400> SEQUENCE: 31
gcatttgttt gtacaagat                                               19

<210> SEQ ID NO 32
<211> LENGTH: 19
<212> TYPE: DNA
<213> ORGANISM: Homo sapiens

<400> SEQUENCE: 32
gatccgcaga cgtgtaaat                                               19

<210> SEQ ID NO 33
<211> LENGTH: 19
<212> TYPE: DNA
<213> ORGANISM: Homo sapiens

<400> SEQUENCE: 33
atgttcctgc aaaaacaca                                               19
```

-continued

```
<210> SEQ ID NO 34
<211> LENGTH: 19
<212> TYPE: DNA
<213> ORGANISM: Homo sapiens

<400> SEQUENCE: 34
tgttcctgca aaacacag                                                   19

<210> SEQ ID NO 35
<211> LENGTH: 19
<212> TYPE: DNA
<213> ORGANISM: Homo sapiens

<400> SEQUENCE: 35
aaacacagac tcgcgttgc                                                  19

<210> SEQ ID NO 36
<211> LENGTH: 19
<212> TYPE: DNA
<213> ORGANISM: Homo sapiens

<400> SEQUENCE: 36
aacacagact cgcgttgca                                                  19

<210> SEQ ID NO 37
<211> LENGTH: 19
<212> TYPE: DNA
<213> ORGANISM: Homo sapiens

<400> SEQUENCE: 37
acacagactc gcgttgcaa                                                  19

<210> SEQ ID NO 38
<211> LENGTH: 19
<212> TYPE: DNA
<213> ORGANISM: Homo sapiens

<400> SEQUENCE: 38
cacagactcg cgttgcaag                                                  19

<210> SEQ ID NO 39
<211> LENGTH: 19
<212> TYPE: DNA
<213> ORGANISM: Homo sapiens

<400> SEQUENCE: 39
ggcgaggcag cttgagtta                                                  19

<210> SEQ ID NO 40
<211> LENGTH: 19
<212> TYPE: DNA
<213> ORGANISM: Homo sapiens

<400> SEQUENCE: 40
acgaacgtac ttgcagatg                                                  19

<210> SEQ ID NO 41
<211> LENGTH: 19
<212> TYPE: DNA
<213> ORGANISM: Homo sapiens

<400> SEQUENCE: 41
cgaacgtact tgcagatgt                                                  19
```

```
<210> SEQ ID NO 42
<211> LENGTH: 19
<212> TYPE: DNA
<213> ORGANISM: Homo sapiens

<400> SEQUENCE: 42
cgtacttgca gatgtgaca                                            19

<210> SEQ ID NO 43
<211> LENGTH: 19
<212> TYPE: DNA
<213> ORGANISM: Homo sapiens

<400> SEQUENCE: 43
gtggtcccag gctgcaccc                                            19

<210> SEQ ID NO 44
<211> LENGTH: 19
<212> TYPE: DNA
<213> ORGANISM: Homo sapiens

<400> SEQUENCE: 44
ggaggagggc agaatcatc                                            19

<210> SEQ ID NO 45
<211> LENGTH: 19
<212> TYPE: DNA
<213> ORGANISM: Homo sapiens

<400> SEQUENCE: 45
gtggtgaagt tcatggatg                                            19

<210> SEQ ID NO 46
<211> LENGTH: 21
<212> TYPE: DNA
<213> ORGANISM: Homo sapiens

<400> SEQUENCE: 46
aatcatcacg aagtggtgaa g                                         21

<210> SEQ ID NO 47
<211> LENGTH: 21
<212> TYPE: DNA
<213> ORGANISM: Homo sapiens

<400> SEQUENCE: 47
aagttcatgg atgtctatca g                                         21

<210> SEQ ID NO 48
<211> LENGTH: 21
<212> TYPE: DNA
<213> ORGANISM: Homo sapiens

<400> SEQUENCE: 48
aatcgagacc ctggtggaca t                                         21

<210> SEQ ID NO 49
<211> LENGTH: 21
<212> TYPE: DNA
<213> ORGANISM: Homo sapiens

<400> SEQUENCE: 49
aatgacgagg gcctggagtg t                                         21
```

```
<210> SEQ ID NO 50
<211> LENGTH: 21
<212> TYPE: DNA
<213> ORGANISM: Homo sapiens

<400> SEQUENCE: 50
aacatcacca tgcagattat g                                              21

<210> SEQ ID NO 51
<211> LENGTH: 21
<212> TYPE: DNA
<213> ORGANISM: Homo sapiens

<400> SEQUENCE: 51
aaacctcacc aaggccagca c                                              21

<210> SEQ ID NO 52
<211> LENGTH: 21
<212> TYPE: DNA
<213> ORGANISM: Homo sapiens

<400> SEQUENCE: 52
aaggccagca cataggagag a                                              21

<210> SEQ ID NO 53
<211> LENGTH: 21
<212> TYPE: DNA
<213> ORGANISM: Homo sapiens

<400> SEQUENCE: 53
aacaaatgtg aatgcagacc a                                              21

<210> SEQ ID NO 54
<211> LENGTH: 21
<212> TYPE: DNA
<213> ORGANISM: Homo sapiens

<400> SEQUENCE: 54
aaatgtgaat gcagaccaaa g                                              21

<210> SEQ ID NO 55
<211> LENGTH: 21
<212> TYPE: DNA
<213> ORGANISM: Homo sapiens

<400> SEQUENCE: 55
aatgcagacc aaagaaagat a                                              21

<210> SEQ ID NO 56
<211> LENGTH: 21
<212> TYPE: DNA
<213> ORGANISM: Homo sapiens

<400> SEQUENCE: 56
aaagaaagat agagcaagac a                                              21

<210> SEQ ID NO 57
<211> LENGTH: 21
<212> TYPE: DNA
<213> ORGANISM: Homo sapiens

<400> SEQUENCE: 57
aagaaagata gagcaagaca a                                              21
```

```
<210> SEQ ID NO 58
<211> LENGTH: 23
<212> TYPE: DNA
<213> ORGANISM: Homo sapiens

<400> SEQUENCE: 58
aagatagagc aagacaagaa aat                                              23

<210> SEQ ID NO 59
<211> LENGTH: 23
<212> TYPE: DNA
<213> ORGANISM: Homo sapiens

<400> SEQUENCE: 59
aagacaagaa aatccctgtg ggc                                              23

<210> SEQ ID NO 60
<211> LENGTH: 23
<212> TYPE: DNA
<213> ORGANISM: Homo sapiens

<400> SEQUENCE: 60
aagaaaatcc ctgtgggcct tgc                                              23

<210> SEQ ID NO 61
<211> LENGTH: 23
<212> TYPE: DNA
<213> ORGANISM: Homo sapiens

<400> SEQUENCE: 61
aatccctgtg ggccttgctc aga                                              23

<210> SEQ ID NO 62
<211> LENGTH: 23
<212> TYPE: DNA
<213> ORGANISM: Homo sapiens

<400> SEQUENCE: 62
aagcatttgt ttgtacaaga tcc                                              23

<210> SEQ ID NO 63
<211> LENGTH: 23
<212> TYPE: DNA
<213> ORGANISM: Homo sapiens

<400> SEQUENCE: 63
aagatccgca gacgtgtaaa tgt                                              23

<210> SEQ ID NO 64
<211> LENGTH: 23
<212> TYPE: DNA
<213> ORGANISM: Homo sapiens

<400> SEQUENCE: 64
aaatgttcct gcaaaaacac aga                                              23

<210> SEQ ID NO 65
<211> LENGTH: 23
<212> TYPE: DNA
<213> ORGANISM: Homo sapiens

<400> SEQUENCE: 65
aatgttcctg caaaaacaca gac                                              23
```

<210> SEQ ID NO 66
<211> LENGTH: 23
<212> TYPE: DNA
<213> ORGANISM: Homo sapiens

<400> SEQUENCE: 66
aaaaacacag actcgcgttg caa                                             23

<210> SEQ ID NO 67
<211> LENGTH: 23
<212> TYPE: DNA
<213> ORGANISM: Homo sapiens

<400> SEQUENCE: 67
aaaacacaga ctcgcgttgc aag                                             23

<210> SEQ ID NO 68
<211> LENGTH: 23
<212> TYPE: DNA
<213> ORGANISM: Homo sapiens

<400> SEQUENCE: 68
aaacacagac tcgcgttgca agg                                             23

<210> SEQ ID NO 69
<211> LENGTH: 23
<212> TYPE: DNA
<213> ORGANISM: Homo sapiens

<400> SEQUENCE: 69
aacacagact cgcgttgcaa ggc                                             23

<210> SEQ ID NO 70
<211> LENGTH: 23
<212> TYPE: DNA
<213> ORGANISM: Homo sapiens

<400> SEQUENCE: 70
aaggcgaggc agcttgagtt aaa                                             23

<210> SEQ ID NO 71
<211> LENGTH: 23
<212> TYPE: DNA
<213> ORGANISM: Homo sapiens

<400> SEQUENCE: 71
aaacgaacgt acttgcagat gtg                                             23

<210> SEQ ID NO 72
<211> LENGTH: 23
<212> TYPE: DNA
<213> ORGANISM: Homo sapiens

<400> SEQUENCE: 72
aacgaacgta cttgcagatg tga                                             23

<210> SEQ ID NO 73
<211> LENGTH: 23
<212> TYPE: DNA
<213> ORGANISM: Homo sapiens

<400> SEQUENCE: 73
aagtggtccc aggctgcacc cat                                             23

```
<210> SEQ ID NO 74
<211> LENGTH: 23
<212> TYPE: DNA
<213> ORGANISM: Homo sapiens

<400> SEQUENCE: 74
aaggaggagg gcagaatcat cac                                              23

<210> SEQ ID NO 75
<211> LENGTH: 23
<212> TYPE: DNA
<213> ORGANISM: Homo sapiens

<400> SEQUENCE: 75
aagtggtgaa gttcatggat gtc                                              23

<210> SEQ ID NO 76
<211> LENGTH: 23
<212> TYPE: DNA
<213> ORGANISM: Homo sapiens

<400> SEQUENCE: 76
aaaatccctg tgggccttgc tca                                              23

<210> SEQ ID NO 77
<211> LENGTH: 21
<212> TYPE: DNA
<213> ORGANISM: Artificial Sequence
<220> FEATURE:
<223> OTHER INFORMATION: synthesized

<400> SEQUENCE: 77
accucaccaa ggccagcact t                                                21

<210> SEQ ID NO 78
<211> LENGTH: 21
<212> TYPE: DNA
<213> ORGANISM: Artificial Sequence
<220> FEATURE:
<223> OTHER INFORMATION: synthesized

<400> SEQUENCE: 78
gugcuggccu uggugaggut t                                                21

<210> SEQ ID NO 79
<211> LENGTH: 18
<212> TYPE: DNA
<213> ORGANISM: Homo sapiens

<400> SEQUENCE: 79
ggctacgtcc agcgcacc                                                    18

<210> SEQ ID NO 80
<211> LENGTH: 21
<212> TYPE: RNA
<213> ORGANISM: Homo sapiens

<400> SEQUENCE: 80
aaaccucacc aaagccagca c                                                21

<210> SEQ ID NO 81
<211> LENGTH: 21
<212> TYPE: DNA
<213> ORGANISM: Homo sapiens
```

```
<400> SEQUENCE: 81
aaggaggagg gcagaatcat c                                              21

<210> SEQ ID NO 82
<211> LENGTH: 21
<212> TYPE: DNA
<213> ORGANISM: Homo sapiens

<400> SEQUENCE: 82
aatgtgaatg cagaccaaag a                                              21

<210> SEQ ID NO 83
<211> LENGTH: 21
<212> TYPE: DNA
<213> ORGANISM: Homo sapiens

<400> SEQUENCE: 83
aaagcatttg tttgtacaag a                                              21

<210> SEQ ID NO 84
<211> LENGTH: 21
<212> TYPE: DNA
<213> ORGANISM: Homo sapiens

<400> SEQUENCE: 84
aagatccgca gacgtgtaaa t                                              21

<210> SEQ ID NO 85
<211> LENGTH: 21
<212> TYPE: DNA
<213> ORGANISM: Homo sapiens

<400> SEQUENCE: 85
aaacacacac tcgcgttgca a                                              21

<210> SEQ ID NO 86
<211> LENGTH: 19
<212> TYPE: DNA
<213> ORGANISM: Homo sapiens

<400> SEQUENCE: 86
aacgtacttg cagatgtga                                                 19

<210> SEQ ID NO 87
<211> LENGTH: 19
<212> TYPE: DNA
<213> ORGANISM: Homo sapiens

<400> SEQUENCE: 87
acgtacttgc agatgtgac                                                 19

<210> SEQ ID NO 88
<211> LENGTH: 19
<212> TYPE: DNA
<213> ORGANISM: Homo sapiens

<400> SEQUENCE: 88
gtacttgcag atgtgacaa                                                 19

<210> SEQ ID NO 89
<211> LENGTH: 19
<212> TYPE: DNA
```

<400> SEQUENCE: 89
tacttgcaga tgtgacaag                                          19

<210> SEQ ID NO 90
<211> LENGTH: 19
<212> TYPE: DNA
<213> ORGANISM: Homo sapiens

<400> SEQUENCE: 90
acttgcagat gtgacaagc                                          19

<210> SEQ ID NO 91
<211> LENGTH: 19
<212> TYPE: DNA
<213> ORGANISM: Homo sapiens

<400> SEQUENCE: 91
cttgcagatg tgacaagcc                                          19

<210> SEQ ID NO 92
<211> LENGTH: 19
<212> TYPE: DNA
<213> ORGANISM: Homo sapiens

<400> SEQUENCE: 92
ttgcagatgt gacaagccg                                          19

<210> SEQ ID NO 93
<211> LENGTH: 19
<212> TYPE: DNA
<213> ORGANISM: Homo sapiens

<400> SEQUENCE: 93
tgcagatgtg acaagccga                                          19

<210> SEQ ID NO 94
<211> LENGTH: 19
<212> TYPE: DNA
<213> ORGANISM: Homo sapiens

<400> SEQUENCE: 94
gcagatgtga caagccgag                                          19

<210> SEQ ID NO 95
<211> LENGTH: 19
<212> TYPE: DNA
<213> ORGANISM: Homo sapiens

<400> SEQUENCE: 95
cagatgtgac aagccgagg                                          19

<210> SEQ ID NO 96
<211> LENGTH: 19
<212> TYPE: DNA
<213> ORGANISM: Homo sapiens

<400> SEQUENCE: 96
agatgtgaca agccgaggc                                          19

<210> SEQ ID NO 97
<211> LENGTH: 19
<212> TYPE: DNA

```
<400> SEQUENCE: 97
gatgtgacaa gccgaggcg                                               19

<210> SEQ ID NO 98
<211> LENGTH: 19
<212> TYPE: DNA
<213> ORGANISM: Homo sapiens

<400> SEQUENCE: 98
atgtgacaag ccgaggcgg                                               19

<210> SEQ ID NO 99
<211> LENGTH: 19
<212> TYPE: DNA
<213> ORGANISM: Homo sapiens

<400> SEQUENCE: 99
gtacttgcag atgtgacaa                                               19

<210> SEQ ID NO 100
<211> LENGTH: 19
<212> TYPE: DNA
<213> ORGANISM: Homo sapiens

<400> SEQUENCE: 100
tgcagatgtg acaagccga                                               19

<210> SEQ ID NO 101
<211> LENGTH: 19
<212> TYPE: DNA
<213> ORGANISM: Homo sapiens

<400> SEQUENCE: 101
gcagatgtga caagccgag                                               19

<210> SEQ ID NO 102
<211> LENGTH: 19
<212> TYPE: DNA
<213> ORGANISM: Homo sapiens

<400> SEQUENCE: 102
agatgtgaca agccgaggc                                               19

<210> SEQ ID NO 103
<211> LENGTH: 17
<212> TYPE: DNA
<213> ORGANISM: Homo sapiens

<400> SEQUENCE: 103
aacgtacttg cagatgt                                                 17

<210> SEQ ID NO 104
<211> LENGTH: 17
<212> TYPE: DNA
<213> ORGANISM: Homo sapiens

<400> SEQUENCE: 104
acgtacttgc agatgtg                                                 17

<210> SEQ ID NO 105
<211> LENGTH: 17
<212> TYPE: DNA
<213> ORGANISM: Homo sapiens
```

<400> SEQUENCE: 105
cgtacttgca gatgtga                                                  17

<210> SEQ ID NO 106
<211> LENGTH: 17
<212> TYPE: DNA
<213> ORGANISM: Homo sapiens

<400> SEQUENCE: 106
gtacttgcag atgtgac                                                  17

<210> SEQ ID NO 107
<211> LENGTH: 17
<212> TYPE: DNA
<213> ORGANISM: Homo sapiens

<400> SEQUENCE: 107
tacttgcaga tgtgaca                                                  17

<210> SEQ ID NO 108
<211> LENGTH: 17
<212> TYPE: DNA
<213> ORGANISM: Homo sapiens

<400> SEQUENCE: 108
acttgcagat gtgacaa                                                  17

<210> SEQ ID NO 109
<211> LENGTH: 17
<212> TYPE: DNA
<213> ORGANISM: Homo sapiens

<400> SEQUENCE: 109
cttgcagatg tgacaag                                                  17

<210> SEQ ID NO 110
<211> LENGTH: 17
<212> TYPE: DNA
<213> ORGANISM: Homo sapiens

<400> SEQUENCE: 110
ttgcagatgt gacaagc                                                  17

<210> SEQ ID NO 111
<211> LENGTH: 17
<212> TYPE: DNA
<213> ORGANISM: Homo sapiens

<400> SEQUENCE: 111
tgcagatgtg acaagcc                                                  17

<210> SEQ ID NO 112
<211> LENGTH: 17
<212> TYPE: DNA
<213> ORGANISM: Homo sapiens

<400> SEQUENCE: 112
gcagatgtga caagccg                                                  17

<210> SEQ ID NO 113
<211> LENGTH: 17
<212> TYPE: DNA
<213> ORGANISM: Homo sapiens

<400> SEQUENCE: 113
cagatgtgac aagccga                                                17

<210> SEQ ID NO 114
<211> LENGTH: 17
<212> TYPE: DNA
<213> ORGANISM: Homo sapiens

<400> SEQUENCE: 114
agatgtgaca agccgag                                                17

<210> SEQ ID NO 115
<211> LENGTH: 17
<212> TYPE: DNA
<213> ORGANISM: Homo sapiens

<400> SEQUENCE: 115
gatgtgacaa gccgagg                                                17

<210> SEQ ID NO 116
<211> LENGTH: 17
<212> TYPE: DNA
<213> ORGANISM: Homo sapiens

<400> SEQUENCE: 116
atgtgacaag ccgaggc                                                17

<210> SEQ ID NO 117
<211> LENGTH: 17
<212> TYPE: DNA
<213> ORGANISM: Homo sapiens

<400> SEQUENCE: 117
tgtgacaagc cgaggcg                                                17

<210> SEQ ID NO 118
<211> LENGTH: 17
<212> TYPE: DNA
<213> ORGANISM: Homo sapiens

<400> SEQUENCE: 118
gtgacaagcc gaggcgg                                                17

<210> SEQ ID NO 119
<211> LENGTH: 20
<212> TYPE: DNA
<213> ORGANISM: Homo sapiens

<400> SEQUENCE: 119
ggcttgtcac atttttcttg                                             20

<210> SEQ ID NO 120
<211> LENGTH: 20
<212> TYPE: DNA
<213> ORGANISM: Homo sapiens

<400> SEQUENCE: 120
cccacaggga ttttcttgtc                                             20

<210> SEQ ID NO 121
<211> LENGTH: 20
<212> TYPE: DNA

```
<400> SEQUENCE: 121
ctttcccttt cctcgaactg                                                20

<210> SEQ ID NO 122
<211> LENGTH: 20
<212> TYPE: DNA
<213> ORGANISM: Homo sapiens

<400> SEQUENCE: 122
gctactgcca tccaatcgag                                                20

<210> SEQ ID NO 123
<211> LENGTH: 20
<212> TYPE: DNA
<213> ORGANISM: Homo sapiens

<400> SEQUENCE: 123
gtctttcctg gtgagagatc                                                20

<210> SEQ ID NO 124
<211> LENGTH: 20
<212> TYPE: DNA
<213> ORGANISM: Homo sapiens

<400> SEQUENCE: 124
ctgtcttggg tgcattggag                                                20

<210> SEQ ID NO 125
<211> LENGTH: 20
<212> TYPE: DNA
<213> ORGANISM: Homo sapiens

<400> SEQUENCE: 125
gaggcaggga tgatgttctg                                                20

<210> SEQ ID NO 126
<211> LENGTH: 20
<212> TYPE: DNA
<213> ORGANISM: Homo sapiens

<400> SEQUENCE: 126
catggcaaat tccatggcac                                                20

<210> SEQ ID NO 127
<211> LENGTH: 83
<212> TYPE: DNA
<213> ORGANISM: Homo sapiens

<400> SEQUENCE: 127
aaggcgaggc agcttgagtt aaacgaacgt acttgatctc tcaccaggaa agactgatac    60
agaacgatcg atacagaaac cac                                            83

<210> SEQ ID NO 128
<211> LENGTH: 36
<212> TYPE: DNA
<213> ORGANISM: artificial sequence
<220> FEATURE:
<223> OTHER INFORMATION: synthesized

<400> SEQUENCE: 128
gaacgtactt gcagatgtga caagccaagg cggtga                              36
```

<210> SEQ ID NO 129
<211> LENGTH: 36
<212> TYPE: DNA
<213> ORGANISM: artificial sequence
<220> FEATURE:
<223> OTHER INFORMATION: synthesized

<400> SEQUENCE: 129
gaacgtactt gcagatgtga caagccaagg cggtga                          36

<210> SEQ ID NO 130
<211> LENGTH: 6
<212> TYPE: PRT
<213> ORGANISM: Artificial sequence
<220> FEATURE:
<223> OTHER INFORMATION: synthesized

<400> SEQUENCE: 130

Cys Asp Lys Pro Arg Arg
1               5

<210> SEQ ID NO 131
<211> LENGTH: 20
<212> TYPE: DNA
<213> ORGANISM: Artificial sequence
<220> FEATURE:
<223> OTHER INFORMATION: synthesized

<400> SEQUENCE: 131
ggcttgtcac attttcttg                                             20

<210> SEQ ID NO 132
<211> LENGTH: 20
<212> TYPE: DNA
<213> ORGANISM: Artificial sequence
<220> FEATURE:
<223> OTHER INFORMATION: synthesized

<400> SEQUENCE: 132
cccacaggga ttttcttgtc                                            20

<210> SEQ ID NO 133
<211> LENGTH: 20
<212> TYPE: DNA
<213> ORGANISM: Artificial sequence
<220> FEATURE:
<223> OTHER INFORMATION: synthesized

<400> SEQUENCE: 133
ctttcccttt cctcgaactg                                            20

<210> SEQ ID NO 134
<211> LENGTH: 20
<212> TYPE: DNA
<213> ORGANISM: Artificial sequence
<220> FEATURE:
<223> OTHER INFORMATION: synthesized

<400> SEQUENCE: 134
gctactgcca tccaatcgag                                            20

<210> SEQ ID NO 135
<211> LENGTH: 20
<212> TYPE: DNA
<213> ORGANISM: Artificial sequence
<220> FEATURE:
<223> OTHER INFORMATION: synthesized

```
<400> SEQUENCE: 135
gtctttcctg gtgagagatc                                              20

<210> SEQ ID NO 136
<211> LENGTH: 20
<212> TYPE: DNA
<213> ORGANISM: Artificial sequence
<220> FEATURE:
<223> OTHER INFORMATION: synthesized

<400> SEQUENCE: 136
ctgtcttggg tgcattggag                                              20

<210> SEQ ID NO 137
<211> LENGTH: 20
<212> TYPE: DNA
<213> ORGANISM: Artificial sequence
<220> FEATURE:
<223> OTHER INFORMATION: synthesized

<400> SEQUENCE: 137
gaggcaggga tgatgttctg                                              20

<210> SEQ ID NO 138
<211> LENGTH: 20
<212> TYPE: DNA
<213> ORGANISM: Artificial sequence
<220> FEATURE:
<223> OTHER INFORMATION: synthesized

<400> SEQUENCE: 138
catggcaaat tccatggcac                                              20
```

COMPOSITIONS AND METHODS FOR SELECTIVE INHIBITION OF VEGF

CROSS-REFERENCE TO RELATED APPLICATIONS

This application claims priority to U.S. Provisional Application No. 61/119,779 entitled "Compositions and Methods for Selective Inhibition of VEGF" filed Dec. 4, 2008, U.S. Provisional No. 61/171,571 entitled "Compositions and Methods for Selective Inhibition of VEGF" filed Apr. 22, 2009, and U.S. Provisional Application No. 61/219,808 entitled "Compositions and Methods for Selective Inhibition of VEGF" filed Jun. 24, 2009, each of which is incorporated by reference in its entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

1. Field of Invention
Not applicable
2. Description of Related Art
Not applicable

BRIEF SUMMARY OF THE INVENTION

Angiogenesis, defined as the growth of new capillary blood vessels or "neovascularization," plays a fundamental role in growth and development. In mature humans, the ability to initiate angiogenesis is present in all tissues, but is held under strict control. A key regulator of angiogenesis is vascular endothelial growth factor ("VEGF"), also called vascular permeability factor ("VPF"). Angiogenesis is initiated when secreted VEGF binds to the Flt-1 and Flk-1/KDR receptors (also called VEGF receptor 1 and VEGF receptor 2), which are expressed on the surface of endothelial cells. Flt-1 and Flk-1/KDR are transmembrane protein tyrosine kinases, and binding of VEGF initiates a cell signal cascade resulting in the ultimate neovascularization in the surrounding tissue.

There are three main different VEGF alternative splice forms (i.e., isoforms) in humans (VEGF$_{121}$, VEGF$_{165}$, and VEGF$_{189}$), while a number of other variants also exist (VEGF$_{206}$, VEGF$_{183}$, VEGF$_{148}$, VEGF$_{165b}$ and VEGF$_{145}$). Remarkably, not all of the isoforms are pro-angiogenic. It has been demonstrated that at least VEGF$_{165b}$ is capable of counteracting the effects of VEGF$_{165}$ induced angiogenesis. Without being bound by theory, it appears that VEGF$_{165b}$ is capable of preventing VEGF Receptor 2 signaling. As such, secretion of VEGF$_{165b}$ may be able to prevent or retard angiogenesis in pathological states.

Aberrant angiogenesis, or the pathogenic growth of new blood vessels, is implicated in a number of conditions. Among these conditions are diabetic retinopathy, psoriasis, exudative or "wet" age-related macular degeneration ("ARMD"), rheumatoid arthritis and other inflammatory diseases, and most cancers. The diseased tissues or tumors associated with these conditions express abnormally high levels of VEGF, and show a high degree of vascularization or vascular permeability.

ARMD in particular is a clinically important angiogenic disease. This condition is characterized by choroidal neovascularization in one or both eyes in aging individuals, and is the major cause of blindness in industrialized countries.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA to within one nucleotide resolution. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene. However, such methods are not directly able to be translated into therapeutic agents for treatment of disease.

What is needed, therefore, are agents which selectively inhibit expression of pro-angiogenic VEGF in catalytic or sub-stoichiometric amounts in mammals, while inducing or maintaining the secretion of anti-angiogenic VEGF isoforms.

The present disclosure is directed to siRNAs which specifically target and cause RNAi-induced degradation of mRNA from VEGF and its isoforms. The siRNA compounds and compositions of the disclosure are used to inhibit angiogenesis, in particular for the treatment of cancerous tumors, age-related macular degeneration, and other angiogenic diseases.

Thus, the disclosure provides an isolated siRNA which targets human VEGF mRNA, or an alternative splice form, mutant or cognate thereof. For example, in one embodiment, the siRNA targets pro-angiogenic VEGF mRNA isoforms such as VEGF$_{121}$, VEGF$_{165}$, VEGF$_{189}$, VEGF$_{206}$, VEGF$_{183}$, VEGF$_{148}$, and/or VEGF$_{145}$, while selectively sparing anti-angiogenic VEGF$_{165b}$ mRNA. In certain embodiments, the siRNA comprises a sense RNA strand and an antisense RNA strand which form an RNA duplex. The sense RNA strand comprises a nucleotide sequence identical to a target sequence of about 19 to about 25 contiguous nucleotides in the target mRNA.

The disclosure also provides recombinant plasmids and viral vectors which express the siRNA disclosed herein, as well as pharmaceutical compositions comprising such an siRNA and a pharmaceutically acceptable carrier.

The disclosure further provides a method of inhibiting expression of human pro-angiogenic VEGF mRNA, or an alternative splice form, mutant or cognate thereof, while sparing anti-angiogenic VEGF mRNA, comprising administering to a subject an effective amount of siRNA such that the target mRNA is degraded.

The disclosure further provides a method of inhibiting angiogenesis in a subject, comprising administering to a subject an effective amount of an siRNA targeted to pro-angiogenic human VEGF mRNA or an alternative splice form, mutant or cognate thereof, while sparing anti-angiogenic mRNA.

The disclosure further provides a method of treating an angiogenic disease, comprising administering to a subject in need of such treatment an effective amount of an siRNA targeted to human proangiogenic VEGF mRNA or an alternative splice form, mutant or cognate thereof, such that angiogenesis associated with the angiogenic disease is inhibited, while the effects of anti-angiogenic VEGF mRNA are not affected.

DESCRIPTION OF DRAWINGS

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be had to the following detailed description taken in connection with the accompanying drawings, in which:

FIG. 11 is a diagram comparing the homology of $VEGF_{165}$ and $VEGF_{165b}$ at the exon 7/8 junction.

FIG. 23 depicts the cytokine profile of ARPE19 cells following treatment with selected siRNAs.

FIG. 32 depicts the stability of OPK-HVB-010 under different temperature conditions over time FIG. 33 depicts the homology between human, rat and mouse VEGF sequences at the 3' terminal end.

FIG. 39 depicts the effect of siRNAs on mouse VEGF secretion by NIH3T3 cells

DETAILED DESCRIPTION

Figure 1A:
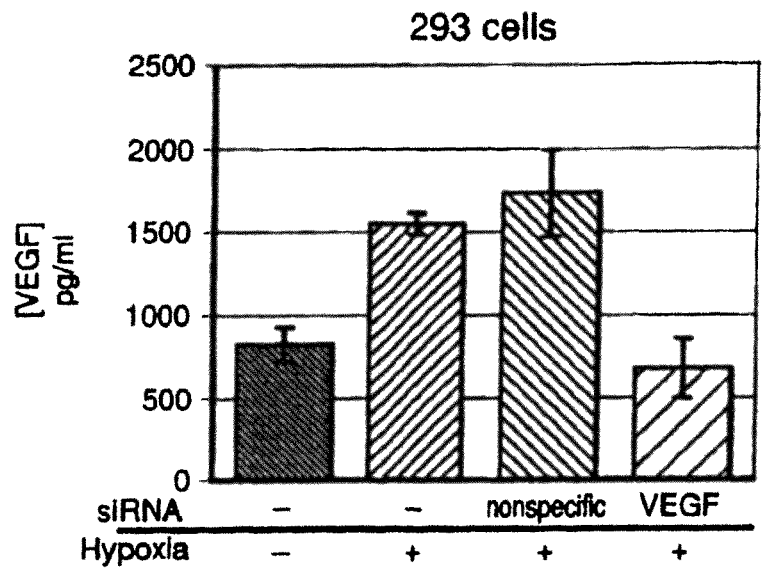
FIGS. 1A and 1B are a histograms of VEGF concentration (in pg/ml) in hypoxic 293 and HeLa cells treated with no siRNA ("–"); nonspecific siRNA ("nonspecific"); or siRNA targeting human VEGF mRNA ("VEGF"). VEGF concentration (in pg/ml) in non-hypoxic 293 and HeLa cells is also shown. Each bar represents the average of four experiments, and the error is the standard deviation of the mean.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "molecule" is a reference to one or more molecules and equivalents thereof known to those skilled in the art, and so forth. As used herein, the term "about" means plus or minus 10% of the numerical value of the number with which it is being used. Therefore, about 50% means in the range of 45%-55%.

As used herein, a "subject" includes a human being or non-human animal. In certain embodiments, the subject is a human being.

As used herein, an "effective amount" of the siRNA is an amount sufficient to cause RNAi-mediated degradation of the target mRNA in cell. The term clinically effective amount is an amount that when administered to a subject, will inhibit the progression of angiogenesis in a subject by RNA silencing.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

As used herein, "target mRNA" means an mRNA comprising a complementary sense sequence to an siRNA antisense strand. Such a target mRNA need not be 100% homologous to the siRNA antisense strand, as long as the siRNA functions to silence or otherwise form a RISC complex with the target mRNA. Target mRNAs of particular use in the methods of the disclosure include, for example, pro-angiogenic VEGF mRNA isoforms such as $VEGF_{121}$, $VEGF_{165}$, and $VEGF_{189}$, $VEGF_{206}$, $VEGF_{183}$, $VEGF_{148}$, and $VEGF_{145}$ and combinations thereof. In certain other embodiments, the target mRNA does not comprise anti-angiogenic $VEGF_{165b}$ mRNA, but targets at least one other VEGF isoforms.

As used herein the term "partially non-complementary" is intended to mean an siRNA sequence which although, perhaps sharing some sequence homology to a non-target sequence still differs sufficiently such that RNA silencing does not occur for the non-target sequence. Partially non-complementary include sequences that are 90% homologous, 85%, homologous, 80% homologous, 75% homologous, 70% homologous, 65% homologous, 60%, homologous, 55% homologous, 50% homologous, 45% homologous, 40% homologous, 35%, homologous, 30% homologous, 25% homologous, 20% homologous, 15% homologous, 10%, homologous, 5% homologous, 2% homologous, and 1% homologous to a non-target sequence. A sequence that is entirely non-homologous to a non-target sequence is considered non-complementary to the sequence.

As used herein, a gene or mRNA which is "cognate" to human VEGF or mRNA from another mammalian species which is homologous to human VEGF. For example, the cognate VEGF mRNA from the mouse is given in SEQ ID NO: 1.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Compositions and methods comprising siRNA targeted to VEGF and its various isoforms can be used to inhibit angiogenesis, in particular for the treatment of angiogenic disease. The siRNA are believed to cause the RNAi-mediated degradation of these mRNAs, so that the protein product of the VEGF and its isoforms are not produced or is produced in reduced amounts. Because VEGF binding to the Flt-1 or Flk-1/KDR receptors is required for initiating and maintaining angiogenesis, the siRNA-mediated degradation of VEGF and its isoforms as well as Flt-1 or Flk-1/KDR mRNA may also be used to inhibit the angiogenic process.

One aspect of the present disclosure therefore provides isolated siRNA comprising short double-stranded RNA from about 17 nucleotides to about 29 nucleotides in length, and in certain embodiments from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is identical or closely homologous to a target sequence contained within the target mRNA.

The sense and antisense strands of the siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules.

Splice variants of human VEGF are known, including pro-angiogenic VEGF mRNA isoforms such as $VEGF_{121}$ (SEQ ID NO: 2), VEGF$_{165}$ (SEQ ID NO: 3), and VEGF$_{189}$ (SEQ ID NO: 4), VEGF$_{206}$ (SEQ ID NO: 5; GenBank Accession No. CS245579), VEGF$_{183}$ (GenBank Accession No. A1010438), VEGF$_{148}$ (GenBank Accession No. AF091352), and VEGF$_{145}$ (GenBank Accession No. CS245578), as well as anti-angiogenic VEGF$_{165b}$ mRNA (GenBank Accession No. AF430806). The mRNA transcribed from the human VEGF and its isoforms, as well as Flt-1 (SEQ ID NO: 6) or Flk-1/KDR (SEQ ID NO: 7) genes can be analyzed for further alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), J. Mol. Endocrinol. 25 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the VEGF and its isoforms as well as Flt-1 or Flk-1/KDR genes can be used to query such a database to determine whether ESTs representing alternatively spliced mRNAs have been found for a these genes.

A technique called "RNAse protection" can also be used to identify alternatively spliced VEGF and its isoforms as well as Flt-1 or Flk-1/KDR mRNAs. RNAse protection involves translation of a gene sequence into synthetic RNA, which is hybridized to RNA derived from other cells; for example, cells from tissue at or near the site of neovascularization. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced VEGF and its isoforms as well as Flt-1 or Flk-1/KDR mRNAs. In RT-PCR, mRNA from tissue or cells is converted into cDNA by the enzyme reverse transcriptase, using methods well-known to those of ordinary skill in the art. The coding sequence of the cDNA is then amplified via PCR using a forward primer located in the 5' translated region, and a reverse primer located in the 3' translated region. In some embodiments, all the bases encoding the cDNA are amplified. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

mRNA produced from mutant VEGF and its isoforms as well as Flt-1 or Flk-1/KDR genes can also be readily identified through the techniques described above for identifying alternative splice forms. As used herein, "mutant" VEGF and its isoforms as well as Flt-1 or Flk-1/KDR genes or mRNA include human VEGF and its isoforms as well as Flt-1 or Flk-1/KDR genes or mRNA which differ in sequence from the VEGF and its isoforms as well as Flt-1 or Flk-1/KDR sequences set forth herein. Thus, allelic forms of these genes, and the mRNA produced from them, are considered "mutants" for purposes of this invention.

Figure 10:
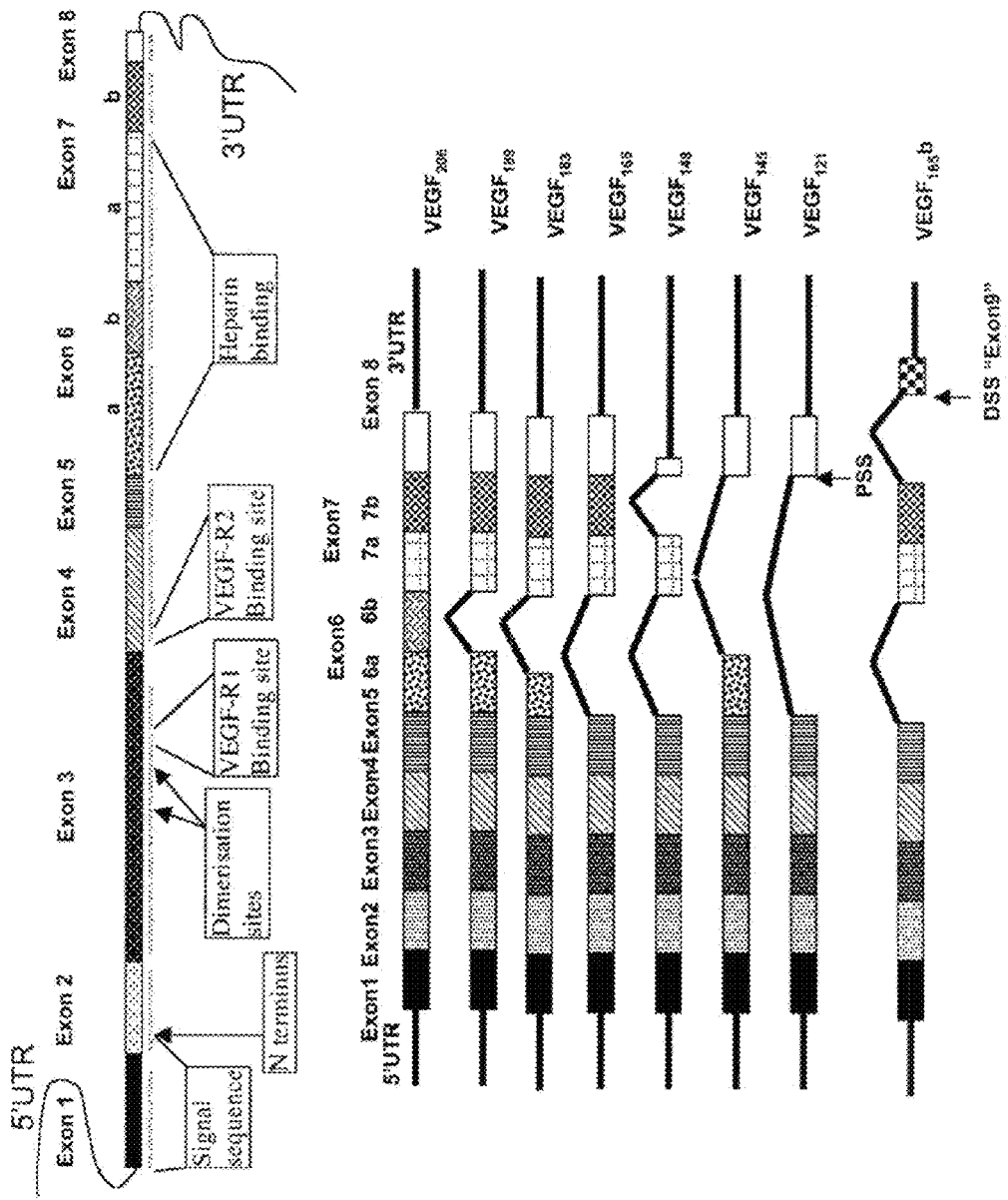
FIG. 10 is a schematic of the various isoforms of VEGF and their exon usage.

It is understood that human VEGF and its isoforms, as well as Flt-1 or Flk-1/KDR mRNA may contain target sequences in common with their respective alternative splice forms, cognates or mutants. A single siRNA comprising such a common targeting sequence can therefore induce RNAi-mediated degradation of different RNA types which contain the common targeting sequence. For example, as shown in FIG. 10, all VEGF isoforms share exons 1-5. However, in VEGF$_{121}$ (SEQ ID NO: 2) exons 6 and 7 (7a and 7b) are deleted. In VEGF$_{165}$ (SEQ ID NO: 3) exon 6 (6a and 6b) is deleted. In VEGF$_{189}$ (SEQ ID NO: 4) exon 6b is deleted. In VEGF$_{183}$ a portion of exon 6a is deleted as well as the complete exon 6b sequence. VEGF$_{148}$ has a deletion of exon 6 (6a and 6b) as well as exon 7b and a portion of exon 8. In VEGF$_{145}$ exon 6b and exon 7 (7a and 7b) are deleted. The only known anti-angiogenic isoform of VEGF, VEGF$_{165}{}^b$, lacks exon 6 (6a and 6b), but additionally comprises a pseudo-exon 9. The pseudo-exon 9 is a result of a reading frame shift caused by the deletion of a stop codon, thus allowing a portion of the 3'UTR to be translated as protein. See for example, Bates et al., Can. Res. 62:4123 (2002), herein incorporated by reference in its entirety. VEGF$_{206}$ (SEQ ID NO: 5) is the full length sequence VEGF with no deletions. Thus, in certain embodiments, the siRNA targets one or more isoforms, such as VEGF$_{121}$ (SEQ ID NO: 2), VEGF$_{165}$ (SEQ ID NO: 3), and VEGF$_{189}$ (SEQ ID NO: 4), VEGF$_{206}$ (SEQ ID NO: 5; GenBank Accession No. CS245579), VEGF$_{183}$ (GenBank Accession No. AJ010438), VEGF$_{148}$ (GenBank Accession No. AF091352), and/or VEGF$_{145}$ (GenBank Accession No. CS245578), but spares others, such as VEGF$_{165b}$, because the siRNA targets a shared exon among certain isoforms but not others.

In one embodiment, provided is an isolated siRNA comprising of a duplex of a first RNA strand and a second RNA strand, said first RNA strand comprising a nucleotide sequence identical to a target sequence of about 19 to about 25 contiguous nucleotides to a vascular endothelial growth factor (VEGF) isoform selected from the group consisting of human VEGF$_{121}$, VEGF$_{165}$ VEGF$_{189}$, VEGF$_{206}$, VEGF$_{183}$, VEGF$_{148}$, VEGF$_{145}$ and combinations thereof; further wherein said siRNA is at least partially non-complementary to VEGF$_{165b}$, with the proviso that the human VEGF mRNA is not SEQ ID NO. 42. Further embodiments include methods of using such siRNA to inhibit angiogenesis and pharmaceutical compositions comprising a therapeutically effective amount of such siRNA to inhibit angiogenesis.

The siRNA can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA can also comprise a 3' overhang. As used herein, a "3' overhang" refers to at least one unpaired nucleotide extending from the 3'-end of a duplexed RNA strand. In some embodiments, the siRNA does not comprise a overhang and has a blunt end. In some embodiments, both ends of the siRNA comprise a blunt end. In some embodiments, the siRNA comprises a 17 mer that contiguous with a target mRNA and dTdT overhang. In some embodiments, the siRNA is a siRNA that can inhibit the secretion or production of VEGF from cells from different species. For example, in some embodiments, the siRNA can inhibit VEGF secretion or inhibition from a human cell, a rat cell, and/or a mouse cell. In some embodiments, the siRNA can inhibit the secretion or production of VEGF from a mouse cell and a human cell, but not from a rat cell. In some embodiments, the siRNA can inhibit the secretion or production of VEGF from a rat cell and a human cell, but not from a mouse cell. In some embodiments, the siRNA can inhibit the secretion or production of VEGF from a human cell, a mouse cell, and a rat cell. The selectivity of the siRNA can be based upon the homology between the different sequences. For example, FIG. 33 shows the homology between the terminal codons encoding human, mouse and rat VEGF. These differences can be exploited to produce siRNAs that can selectively inhibit the production of VEGF from one or more species.

In some embodiments, siRNAs comprising less than 21 nucleotides, e.g. 17, 18, 19, or 20, can be used to avoid any potential non-specific in vivo responses. (See, Ambati, Nature, 452, 591-597 (3 Apr. 2008)). For example, siRNAs comprising less than 21 nucleotides can be used to avoid potentially activating a TLR3 response in vivo.

Thus in one embodiment, the siRNA comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In a further embodiment, the siRNA comprises a sequence having no more than five (5) consecutive purines or pyrimidines. In a further embodiment, the siRNA comprises a sequence having no more than five (5) consecutive nucleotides having the same nucleobase (i.e., A, C, G, or U/T).

The siRNA can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

In some embodiments, the siRNA is 19 nucleotides and comprises 17 nucleotides that are identical to a target mRNA. In some embodiments, the siRNA is 19 nucleotides in length comprising at least one blunt end. In some embodiments, each end of the 19 mer has a blunt end. In some embodiments, the 19 mer comprises at least one dT overhang. In some embodiments, the 19 mer comprises two dT overhangs.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon (see, e.g., the target sequences of SEQ ID NOS: 73 and 74 in Table 1 below, which are within 100 nt of the 5'-end of the $VEGF_{121}$ cDNA.

In a further embodiment of the present invention, the target mRNA sequence comprises no more than five (5) consecutive purines or pyrimidines. For example, a suitable target sequence in the $VEGF_{121}$ cDNA sequence is:

```
TCATCACGAAGTGGTGAAG        (SEQ ID NO: 8)
```

Thus, an siRNA targeting this sequence, and which has 3' uu overhangs on each strand (overhangs shown in bold), is:

```
5'-ucaucacgaaguggugaaguu-3'   (SEQ ID NO: 9)

3'-uuaguagugcuucaccacuuc-5'   (SEQ ID NO: 10)
```

An siRNA targeting this same sequence, but having 3' TT overhangs on each strand (overhangs shown in bold) is:

```
5'-ucaucacgaaguggugaagTT-3'   (SEQ ID NO: 11)

3'-TTaguagugcuucaccacuuc-5'   (SEQ ID NO: 12)
```

Other $VEGF_{121}$ target sequences from which siRNA can be derived are given in Table 1. It is understood that all $VEGF_{121}$ target sequences listed in Table 1 are within that portion of the $VEGF_{121}$ alternative splice form which is common to all human VEGF alternative splice forms. Thus, the $VEGF_{121}$ target sequences in Table 1 can also target $VEGF_{165}$, $VEGF_{189}$, and $VEGF_{206}$ mRNA. Target sequences which target a specific VEGF isoform can also be readily identified. For example, a target sequence which targets VEGF$_{165}$ mRNA but not VEGF$_{121}$ mRNA is AACGTACTTGCAGATGTGACA (SEQ ID NO: 13). Conversely, target sequences which target pro-angiogenic VEGF mRNA isoforms such as VEGF$_{121}$, VEGF$_{165}$, and VEGF$_{189}$, VEGF$_{206}$, VEGF$_{183}$, VEGF$_{148}$, and VEGF$_{145}$ and combinations thereof, but does not target anti-angiogenic VEGF$_{165b}$ mRNA include the sequences found in Table 2, with the proviso that the VEGF mRNA is not SEQ ID No. 42. In certain embodiments, said human VEGF mRNA is selected from the group consisting of SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98, SEQ ID NO 99, SEQ ID NO 100, SEQ ID NO 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, and SEQ ID NO: 118. In certain embodiments, said human VEGF mRNA is selected from SEQ ID NO. 88 and SEQ ID NO. 94.

By selectively targeting the angiogenic isoforms of VEGF, while sparing the anti-angiogenic isoform, it is possible to enhance the anti-angiogenic effects of siRNA treatment. As shown in FIG. 11, the region between exon 7 and 9 differ between the angiogenic and antiangiogenic sequences. According to the various embodiments, it is possible to selectively target this region where the siRNA is at least partially complementary to the angiogenic isoforms, but at least partially or fully non-complementary to the anti-angiogenic isoform. Consequently, in certain embodiments, the siRNA would not inhibit the expression of the anti-angiogenic isoform, VEGF$_{165b}$ with the proviso that the VEGF mRNA is not SEQ ID No. 42. In certain embodiments, said human VEGF mRNA is selected from the group consisting of SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98, SEQ ID NO 99, SEQ ID NO 100, SEQ ID NO 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ. ID NO: 116, SEQ ID NO: 117, and SEQ ID NO: 118. In certain embodiments, said human VEGF mRNA is selected from SEQ ID NO. 88 and SEQ ID NO. 94.

Exemplary target sequences for human Flt-1 for human Flk-1/KDR are given in PCT/US2003/0022444 filed Jul. 18, 2003, herein incorporated by reference in its entirety.

TABLE 1

VEGF Target Sequences

| target sequence | SEQ ID NO: | target sequence | SEQ ID NO: |
|---|---|---|---|
| cognate VEGF mRNA sequence | 1 | GATAGAGCAAGACAAGAAA | 26 |
| Splice variant VEGF$_{121}$ sequence | 2 | GACAAGAAAATCCCTGTGG | 27 |
| Splice variant VEGF$_{165}$ sequence | 3 | GAAAATCCCTGTGGGCCTT | 28 |
| Splice variant VEGF$_{189}$ sequence | 4 | AATCCCTGTGGGCCTTGCT | 29 |
| Splice variant VEGF$_{206}$ sequence | 5 | TCCCTGTGGGCCTTGCTCA | 30 |
| TCATCACGAAGTGGTGAAG | 8 | GCATTTGTTTGTACAAGAT | 31 |
| ucaucacgaaguggugaaguu | 9 | GATCCGGAGACGTGTAAAT | 32 |
| uuaguagugcuucaccacuuc | 10 | ATGTTCGTGCAAAAACACA | 33 |
| ucaucacgaaguggugaagTT | 11 | TGTTCCTGCAAAAACACAG | 34 |
| TTaguagugcuucaccacuuc | 12 | AAACACAGACTCGCGTTGC | 35 |
| AACGTACTTGCAGATGTGACA | 13 | AACACAGACTCGCGTTGCA | 36 |
| GTTCATGGATGTCTATCAG | 14 | ACACAGACTCGCGTTGCAA | 37 |
| TCGAGACCCTGGTGGACAT | 15 | CACAGACTCGCGTTGCAAG | 38 |
| TGACGAGGGCCTGGAGTGT | 16 | GGCGAGGCAGCTTGAGTTA | 39 |
| TGACGAGGGCCTGGAGTGT | 17 | ACGAACGTACTTGCAGATG | 40 |
| CATCACCATGCAGATTATG | 18 | CGAACGTACTTGCAGATGT | 41 |
| ACCTCACCAAGGCCAGCAC | 19 | CGTACTTGCAGATGTGACA | 42 |
| GGCCAGCACATAGGAGAGA | 20 | GTGGTCCAGGCTGCACCC | 43 |
| CAAATGTGAATGCAGACCA | 21 | GGAGGAGGGCAGAATCATC | 44 |
| ATGTGAATGCAGACCAAAG | 22 | GTGGTGAAGTTCATGGATG | 45 |
| TGCAGACCAAAGAAAGATA | 23 | AATCATCACGAAGTGGTGAAG | 46 |

TABLE 1-continued

VEGF Target Sequences

| target sequence | SEQ ID NO: | target sequence | SEQ ID NO: |
|---|---|---|---|
| AGAAAGATAGAGCAAGACA | 24 | AAGTTCATGGATGTCTATCAG | 47 |
| GAAAGATAGAGCAAGACAA | 25 | AATCGAGACCCTGGTGGACAT | 48 |
| AATGACGAGGGCCTGGAGTGT | 49 | AATGTTCCTGCAAAAACACAGAC | 65 |
| AACATGACCATGCAGATTATG | 50 | AAAAACACAGACTCGCGTTGCAA | 66 |
| AAACCTCACCAAGGCCAGCAC | 51 | AAAACACAGACTCGCGTTGCAAG | 67 |
| AAGGCCAGCACATAGGAGAGA | 52 | AAACACAGACTCGCGTTGCAAGG | 68 |
| AACAAATGTGAATGCAGACCA | 53 | AACACAGACTCGCGTTGCAAGGC | 69 |
| AAATGTGAATGCAGACCAAAG | 54 | AAGGCGAGGCAGCTTGAGTTAAA | 70 |
| AATGCAGACCAAAGAAAGATA | 55 | AAACGAACGTACTTGCAGATGTG | 71 |
| AAAGAAAGATAGAGCAAGACA | 56 | AACGAACGTACTTGCAGATGTGA | 72 |
| AAGAAAGATAGAGCAAGACAA | 57 | AAGTGGTCCCAGGCTGCACCCAT | 73 |
| AAGATAGAGCAAGACAAGAAAAT | 58 | AAGGAGGAGGGCAGAATCATCAC | 74 |
| AAGACAAGAAAATCCCTGTGGGC | 59 | AAGTGGTGAAGTTCATGGATGTC | 75 |
| AAGAAAATCCCTGTGGGCCTTGC | 60 | AAAATCCCTGTGGGCCTTGCTCA | 76 |
| AATCCGTGTGGGCCTTGCTCAGA | 61 | accucaccaaggccagcacTT | 77 |
| AAGCATTTGTTTGTACAAGATCC | 62 | gugcuggccuuggugagguTT | 78 |
| AAGATCCGCAGACGTGTAAATGT | 63 | GGCTACGTCCAGCGCACC | 79 |
| AAATGTTCCTGCAAAAACACAGA | 64 | AAACCUCACCAAAGCCAGCAC | 80 |

TABLE 2

VEGF Target Sequences selectively excluding VEGF$_{165b}$

| siRNA Name | Target sequence (5'-3') |
|---|---|
| OPK-HVB-001 | AACGTACTTGCAGATGTGA (SEQ ID NO: 86) |
| OPK-HVB-002 | ACGTACTTGCAGATGTGAC (SEQ ID NO: 87) |
| OPK-HVB-003 | CGTACTTGCAGATGTGACA (SEQ ID NO: 42) |
| OPK-HVB-004 | GTACTTGCAGATGTGACAA (SEQ ID NO: 88) |
| OPK-HVB-005 | TACTTGCAGATGTGACAAG (SEQ ID NO: 89) |
| OPK-HVB-006 | ACTTGCAGATGTGACAAGC (SEQ ID NO: 90) |
| OPK-HVB-007 | CTTGCAGATGTGACAAGCC (SEQ ID NO: 91) |
| OPK-HVB-008 | TTGCAGATGTGACAAGCCG (SEQ ID NO: 92) |
| OPK-HVB-009 | TGCAGATGTGACAAGCCGA (SEQ ID NO: 93) |
| OPK-HVB-010 | GCAGATGTGACAAGCCGAG (SEQ ID NO: 94) |
| OPK-HVB-011 | CAGATGTGACAAGCCGAGG (SEQ ID NO: 95) |
| OPK-HVB-012 | AGATGTGACAAGCCGAGGC (SEQ ID NO: 96) |
| OPK-HVB-013 | GATGTGACAAGCCGAGGCG (SEQ ID NO: 97) |
| OPK-HVB-014 | ATGTGACAAGCCGAGGCGG (SEQ ID NO: 98) |
| OPK-HVB-004be | GTACTTGCAGATGTGACAA (SEQ ID NO: 99) |
| OPK-HVB-009be | TGCAGATGTGACAAGCCGA (SEQ ID NO: 100) |
| OPK-HVB-010be | GCAGATGTGACAAGCCGAG (SEQ ID NO: 101) |
| OPK-HVB-012be | AGATGTGACAAGCCGAGGC (SEQ ID NO: 102) |
| OPK-HVB-001a | AACGTACTTGCAGATGT (SEQ ID NO: 103) |
| OPK-HVB-002a | ACGTACTTGCAGATGTG (SEQ ID NO: 104) |
| OPK-HVB-003a | CGTACTTGCAGATGTGA (SEQ ID NO: 105) |
| OPK-HVB-004a | GTACTTGCAGATGTGAC (SEQ ID NO: 106) |
| OPK-HVB-005a | TACTTGCAGATGTGACA (SEQ ID NO: 107) |
| OPK-HVB-006a | ACTTGCAGATGTGACAA (SEQ ID NO: 108) |
| OPK-HVB-007a | CTTGCAGATGTGACAAG (SEQ ID NO: 109) |
| OPK-HVB-008a | TTGCAGATGTGACAAGC (SEQ ID NO: 110) |
| OPK-HVB-009a | TGCAGATGTGACAAGCC (SEQ ID NO: 111) |

TABLE 2-continued

VEGF Target Sequences selectively excluding VEGF$_{165b}$

| siRNA Name | Target sequence (5'-3') | |
|---|---|---|
| OPK-HVB-010a | GCAGATGTGACAAGCCG | (SEQ ID NO: 112) |
| OPK-HVB-011a | CAGATGTGACAAGCCGA | (SEQ ID NO: 113) |
| OPK-HVB-012a | AGATGTGACAAGCCGAG | (SEQ ID NO: 114) |
| OPK-HVB-013a | GATGTGACAAGCCGAGG | (SEQ ID NO: 115) |
| OPK-HVB-014a | ATGTGACAAGCCGAGGC | (SEQ ID NO: 116) |
| OPK-HVB-015a | TGTGACAAGCCGAGGCG | (SEQ ID NO: 117) |
| OPK-HVB-016a | GTGACAAGCCGAGGCGG | (SEQ ID NO: 118) |

The sequences with the names "OPK-HVB-XXXbe" refer to sequences that are 19 mer blunt end counterparts of the similar 21 mers. The sequences with the names "OPVHVB-XXXa" refer to 19 mers where there is a 17 bp nucleotide sequence with a dTdT overhang. Other sequences not specifically exemplified herein but targeting VEGF while sparing VEGF165b can also be made with similar properties.

The siRNA can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

In certain embodiments, the siRNA are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol,* 20: 446-448; Brummelkamp T R et al. (2002), *Science* 296: 550-553; Miyagishi M et al. (2002), *Nat. Biotechnol.* 20: 497-500; Paddison P J et al. (2002), *Genes Dev.* 16: 948-958; Lee N S et al. (2002), *Nat. Biotechnol.* 20: 500-505; and Paul C P et al. (2002), *Nat. Biotechnol.* 20: 505-508, the entire disclosures of which are herein incorporated by reference.

A plasmid comprising nucleic acid sequences for expressing an siRNA is described in Example 7 below. That plasmid, called pAAVsiRNA, comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid pAAVsiRNA is ultimately intended for use in producing an recombinant adeno-associated viral vector comprising the same nucleic acid sequences for expressing an siRNA.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA can also be expressed from recombinant viral vectors intracellularly at or near the area of neovascularization in vivo. The recombinant viral vectors of the invention comprise sequences encoding the siRNA and any suitable promoter for expressing the siRNA sequences. Suitable promoters include, for example, the U6 or H 1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA to cells in vivo is discussed in more detail below.

siRNA can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Preferred viral vectors are those derived from AV and AAV. In a particularly preferred embodiment, the siRNA is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA, a method for constructing the recombinant AV vector, and a method for delivering the vector into target cells, are described in Xia H et al. (2002), *Nat. Biotech.* 20: 1006-1010.

Suitable AAV vectors for expressing the siRNA, methods for constructing the recombinant AAV vector, and methods for delivering the vectors into target cells are described in Samulski R et al. (1987), *J. Virol.* 61: 3096-3101; Fisher K J et al. (1996), *J. Virol.*, 70: 520-532; Samulski R et al. (1989). *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. An exemplary method for generating a recombinant AAV vector of the invention is described in Example 7 below.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques, or by quantitative RT-PCR. Alternatively, the levels of VEGF and its isoforms as well as Flt-1 or Flk-1/KDR receptor protein in the cultured cells can be measured by ELISA or Western blot. A suitable cell culture system for measuring the effect of the present siRNA on target mRNA or protein levels is described in Example 1 below.

RNAi-mediated degradation of target mRNA by an siRNA containing a given target sequence can also be evaluated with animal models of neovascularization, such as the ROP or CNV mouse models. For example, areas of neovascularization in an ROP or CNV mouse can be measured before and after administration of an siRNA and, in some embodiments, compared to an untreated animal. A reduction in the areas of neovascularization in these models upon administration of the siRNA indicates, in some embodiments, the down-regulation of the target mRNA (see Example 6 below).

As discussed above, the siRNA is capable of targeting and causing the RNAi-mediated degradation of VEGF and its isoforms as well as Flt-1 or Flk-1/KDR mRNA, or alternative splice forms, mutants or cognates thereof, preferably VEGF, and more preferably human VEGF. Degradation of the target mRNA by the present siRNA reduces the production of a functional gene product from the VEGF and its isoforms as well as Flt-1 or Flk-1/KDR genes. Thus, another embodiment of the present invention provides a method of inhibiting expression of VEGF and its isoforms, such as $VEGF_{121}$ (SEQ ID NO: 2), $VEGF_{165}$ (SEQ ID NO: 3), and $VEGF_{189}$ (SEQ ID NO: 4), $VEGF_{206}$ (SEQ ID NO: 5; GenBank Accession No. CS245579), $VEGF_{183}$ (GenBank Accession No. AJ010438), $VEGF_{148}$ (GenBank Accession No. AF091352), and/or $VEGF_{145}$ (GenBank Accession No. CS245578), as well as Flt-1 or Flk-1/KDR in a subject, comprising administering an effective amount of an siRNA to the subject, such that the target mRNA is degraded. As the products of the VEGF and its isoforms as well as Flt-1 and Flk-1/KDR genes are required for initiating and maintaining angiogenesis, another embodiment of the present invention provides a method of inhibiting angiogenesis in a subject by the RNAi-mediated degradation of the target mRNA by the present siRNA.

RNAi-mediated degradation of the target mRNA can be detected by measuring levels of the target mRNA or protein in the cells of a subject, using standard techniques for isolating and quantifying mRNA or protein as described above.

Inhibition of angiogenesis can be evaluated by directly measuring the progress of pathogenic or nonpathogenic angiogenesis in a subject; for example, by observing the size of a neovascularized area before and after treatment with the siRNA. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed, for example, by fluorescein angiography.

Inhibition of angiogenesis can also be inferred through observing a change or reversal in a pathogenic condition associated with the angiogenesis. For example, in ARMD, a slowing, halting or reversal of vision loss indicates an inhibition of angiogenesis in the choroid. For tumors, a slowing, halting or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA.

It is understood that the siRNA can degrade the target mRNA (and thus inhibit angiogenesis) in substoichiometric amounts. Without wishing to be bound by any theory, it is believed that the siRNA causes degradation of the target mRNA in a catalytic manner. Thus, compared to standard anti-angiogenic therapies, significantly less siRNA needs to be delivered at or near the site of neovascularization to have a therapeutic effect.

One skilled in the art can readily determine an effective amount of the siRNA to be administered to a given subject, by taking into account factors such as the size and weight of the subject; the extent of the neovascularization or disease penetration; the age, health and sex of the subject; the route of administration; and whether the administration is regional or systemic. Generally, an effective amount of the siRNA comprises an intercellular concentration at or near the neovascularization site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness.

Preferably, an siRNA is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA is used to inhibit choroidal neovascularization in age-related macular degeneration.

For treating angiogenic diseases, the siRNA can administered to a subject in combination with a pharmaceutical agent which is different from the present siRNA. Alternatively, the siRNA can be administered to a subject in combination with another therapeutic method designed to treat the angiogenic disease. For example, the siRNA can be administered in combination with therapeutic methods currently employed for treating cancer or preventing tumor metastasis (e.g., radiation therapy, chemotherapy, and surgery). For treating tumors, the siRNA is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include, but not limited to, the Mirus Transit TKO lipophilic reagent; lipofectin; lipofectamine; cellfectin; or polycations (e.g., polylysine), or liposomes. In some embodiments the delivery reagent is Ribojuice (Novagen), a siRNA transfection reagent, which comprises amine and lipid based reagents. A preferred delivery reagent is a liposome. In some embodiments, the siRNA is delivered free of a liposomal delivery agent.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019, 369, the entire disclosures of which are herein incorporated by reference.

Preferably, the liposomes encapsulating the present siRNA comprises a ligand molecule that can target the liposome to a particular cell or tissue at or near the site of angiogenesis. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), *P.N.A.S., USA,* 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA are discussed above. Such recombinant plasmids can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA are also discussed above, and methods for delivering such vectors to an area of neovascularization in a patient are within the skill in the art.

The siRNA can be administered to the subject by any means suitable for delivering the siRNA to the cells of the tissue at or near the area of neovascularization. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No. 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. More preferably, the siRNA is administered topically to the eye, e.g. in liquid or gel form to the lower eye lid or conjunctival cul-de-sac, as is within the skill in the art (see, e.g., Acheampong A A et al, 2002, *Drug Metabol. and Disposition* 30: 421-429, the entire disclosure of which is herein incorporated by reference).

Typically, the siRNA is administered topically to the eye in amounts of from about 5 microliters to about 75 microliters, for example from about 7 microliters to about 50 microliters, preferably from about 10 microliters to about 30 microliters. It is understood that topical instillation in the eye of siRNA in volumes greater than 75 microliters can result in loss of siRNA from the eye through spillage and drainage. Thus, it is preferable to administer a high concentration of siRNA (e.g., 100-0.1000 nM) in as small a volume as possible.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A i et al, 2002, supra; and Bennett et al. (1996), *Hum. Gene Ther.* 7: 1763-1769 and Ambati J et al., 2002, *Progress in Retinal and Eye Res.* 21: 145-151, the entire disclosures of which are herein incorporated by reference. In another preferred embodiment, the siRNA is administered by intravitreal injection.

The siRNA can be administered in a single dose or in multiple doses. Where the administration of the siRNA is by infusion, the infusion can be a single sustained dose or can be delivered by multiple infusions. Injection of the agent directly into the tissue is at or near the site of neovascularization preferred. Multiple injections of the agent into the tissue at or near the site of neovascularization are particularly preferred.

One skilled in the art can also readily determine an appropriate dosage regimen for administering the siRNA to a given subject. For example, the siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, and alternatively from about seven to about ten weeks. In a certain dosage regimen, the siRNA is injected at or near the site of neovascularization (e.g., intravitreally) once a week for seven weeks. It is understood that periodic administrations of the siRNA for an indefinite length of time may be necessary for subjects suffering from a chronic neovascularization disease, such as wet ARMD or diabetic retinopathy.

Where a dosage regimen comprises multiple administrations, it is understood that the effective amount of siRNA administered to the subject can comprise the total amount of siRNA administered over the entire dosage regimen.

The siRNA are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science,* 17th ed., Mack Publishing Company, Easton, Pa. (1985), the entire disclosure of which is herein incorporated by reference.

In one embodiment, the pharmaceutical formulations comprise an siRNA (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like.

Pharmaceutical compositions can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-i) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups; for example, hydroxypropylcellulose, polyacrylic acid, high-molecular weight polyethylene glycols (e.g., >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA. A pharmaceutical composition for aerosol (inhalational) administration can comprise 0.01-20% by weight, preferably 1%-10% by weight, of one or more siRNA encapsulated in a liposome as described above, and propellant. A carrier can also be included as desired; e.g., lecithin for intranasal delivery.

The invention will now be illustrated with the following non-limiting examples.

Example 1 siRNA Transfection and Hypoxia Induction In Vitro siRNA Design—A 19 nt sequence located 329 nt from the 5' end of human VEGF mRNA was chosen as a target sequence: AAACCTCACCAAGGCCAGCAC (SEQ ID NO: 51). To ensure that it was not contained in the mRNA from any other genes, this target sequence was entered into the BLAST search engine provided by NCBI. The use of the BLAST algorithm is described in Altschul et al. (1990), *J. Mol. Biol.* 215: 403-410 and Altschul et al. (1997), *Nucleic Acids Res.* 25: 3389-3402, the disclosures of which are herein incorporated by reference in their entirety. As no other mRNA was found which contained the target sequence, an siRNA duplex was synthesized to target this sequence (Dharmacon Research, Inc., Lafayette, Colo.).

The siRNA duplex had the following sense and antisense strands.

```
sense:
5'-accucaccaaggccagcacTT-3'.       (SEQ ID NO: 77)

antisense:
5'-gugcuggccuuggugagguTT-3'.       (SEQ ID NO: 78)
```

Together, the siRNA sense and antisense strands formed a 19 nt double-stranded siRNA with TT 3' overhangs (shown in bold) on each strand. This siRNA was termed "Candidate 5" or "Cand5." Other siRNA which target human VEGF mRNA were designed and tested as described for Cand5 (bevasiranib).

An siRNA targeting the following sequence in green fluorescent protein (GFP) mRNA was used as a nonspecific control: GGCTACGTCCAGCGCACC (SEQ ID NO: 79). The siRNA was purchased from Dharmacon (Lafayette, Colo.).

siRNA Transfection and Hypoxia Induction In Vitro—Human cell lines (293; Hela and ARPE19) were separately seeded into 24-well plates in 250 microliters of complete DMEM medium one day prior to transfection, so that the cells were ~50% confluent at the time of transfection. Cells were transfected with 2.5 nM Cand5 siRNA, and with either no siRNA or 2.5 nM non-specific siRNA (targeting GFP) as controls. Transfections were performed in all cell lines with the "Transit TKO Transfection" reagent, as recommended by the manufacturer (Mirus).

Twenty four hours after transfection, hypoxia was induced in the cells by the addition of deferoxamine mesylate to a final concentration of 130 micromolar in each well. Twenty four hours post-transfection, the cell culture medium was removed from all wells, and a human VEGF ELISA (R&D systems, Minneapolis, Minn.) was performed on the culture medium as described in the Quantikine human VEGF ELISA protocol available from the manufacturer, the entire disclosure of which is herein incorporated by reference.

Figure 1B:
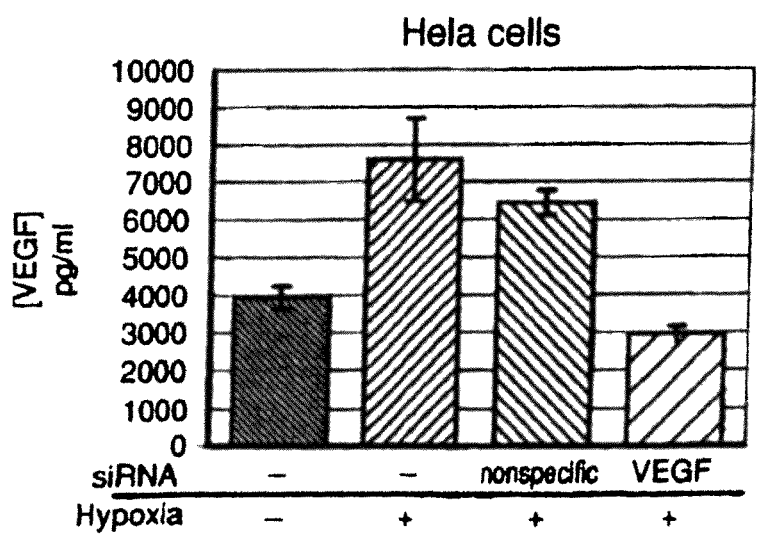

As can be seen in FIG. 1, RNAi degradation induced by Cand5 siRNA significantly reduces the concentration of VEGF produced by the hypoxic 293 and HeLa cells. There was essentially no difference in the amount of VEGF produced by hypoxic cells treated with either no siRNA or the non-specific siRNA control. Similar results were also seen with human ARPE19 cells treated under the same conditions. Thus, RNA interference with VEGF-targeted siRNA disrupts the pathogenic up-regulation of VEGF in human cultured cells in vitro.

The experiment outlined above was repeated on mouse NIH 3T3 cells using a mouse-specific VEGF siRNA (see Example 6 below), and VEGF production was quantified with a mouse VEGF ELISA (R&D systems, Minneapolis, Minn.) as described in the Quantikine mouse VEGF ELISA protocol available from the manufacturer, the entire disclosure of which is herein incorporated by reference. Results similar to those reported in FIG. 1 for the human cell lines were obtained.

Example 2

Effect of Increasing siRNA Concentration on VEGF Production in Human Cultured Cells The experiment outlined in Example 1 was repeated with human 293, HeLa and ARPE19 cells using a range of siRNA concentrations from 10 nM to 50 nM. The ability of the Cand5 siRNA to down-regulate VEGF production increased moderately up to approximately 13 nM siRNA, but a plateau effect was seen above this concentration. These results highlight the catalytic nature of siRNA-mediated RNAi degradation of mRNA, as the plateau effect appears to reflect VEGF production from the few cells not transfected with the siRNA. For the majority of cells which had been transfected with the siRNA, the increased VEGF mRNA production induced by the hypoxia is outstripped by the siRNA-induced degradation of the target mRNA at siRNA concentrations greater than about 13 nM.

Example 3

Specificity of siRNA Targeting

NIH 3T3 mouse fibroblasts were grown in 24-well plates under standard conditions, so that the cells were ~50% confluent one day prior to transfection. The human VEGF siRNA Cand5 was transfected into a NIH 3T3 mouse fibroblasts as in Example 1. Hypoxia was then induced in the transfected cells, and murine VEGF concentrations were measured by ELISA as in Example 1.

Figure 2:
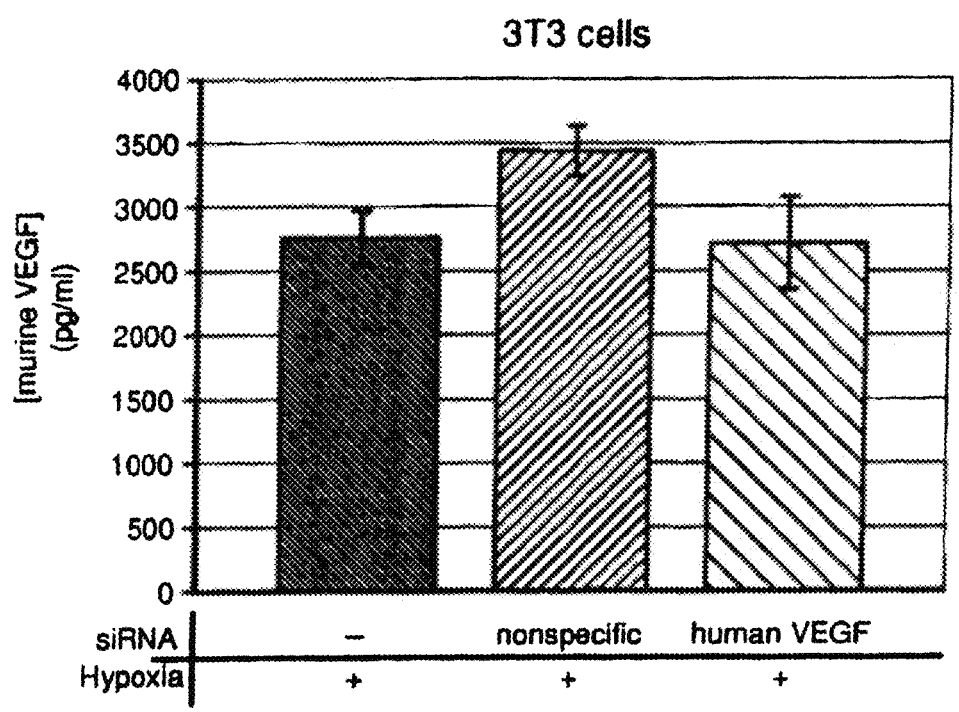
FIG. 2 is a histogram of murine VEGF concentration (in pg/ml) in hypoxic NIH 3T3 cells treated with no siRNA ("–"); nonspecific siRNA ("nonspecific"); or siRNA targeting human VEGF mRNA ("VEGF"). Each bar represents the average of six experiments and the error is the standard deviation of the mean.
Figure 3:
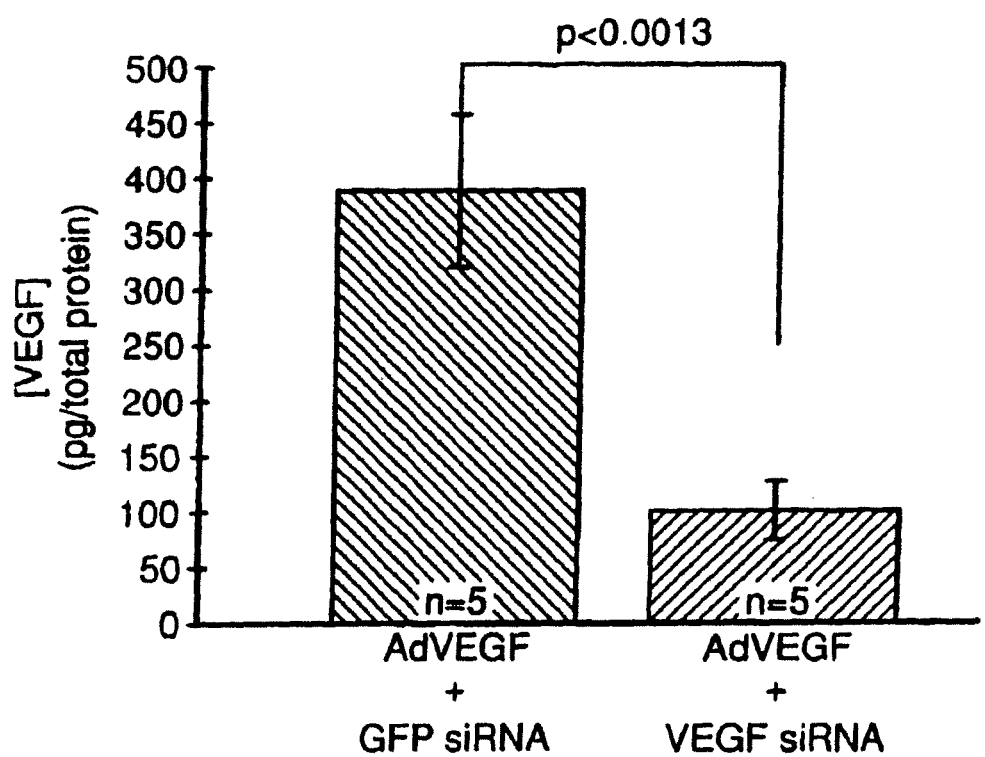
FIG. 3 is a histogram of human VEGF concentration (pg/total protein) in retinas from mice injected with adenovirus expressing human VEGF ("AdVEGF") in the presence of either GFP siRNA (dark gray bar) or human VEGF siRNA (light grey bar). Each bar represents the average of 5 eyes and the error bars represent the standard error of the mean.

The sequence targeted by the human VEGF siRNA Cand5 differs from the murine VEGF mRNA by one nucleotide. As can be seen in FIG. 2, the human VEGF siRNA has no affect on the ability of the mouse cells to up-regulate mouse VEGF after hypoxia. These results show that siRNA induced RNAi degradation is sequence-specific to within a one nucleotide resolution.

Example 4

In Vivo delivery of siRNA to Murine Retinal Pigment Epithelial Cells

VEGF is upregulated in the retinal pigment epithelial (RPE) cells of human patients with age-related macular degeneration (ARMD). To show that functional siRNA can be delivered to RPE cells in vivo, GFP was expressed in mouse retinas with a recombinant adenovirus, and GFP expression was silenced with siRNA. The experiment was conducted as follows.

One eye from each of five adult C57/Black6 mice (Jackson Labs, Bar Harbor, Me.) was injected subretinally as described in Bennett et al. (1996), supra., with a mixture containing ~1×10$^8$ particles of adenovirus containing eGFP driven by the CMV promoter and 20 picomoles of siRNA targeting eGFP conjugated with transit TKO reagent (Mirus).

As positive control, the contralateral eyes were injected with a mixture containing ~1×10$^8$ particles of adenovirus containing eGFP driven by the CMV promoter and 20 picomoles of siRNA targeting human VEGF conjugated with transit TKO reagent (Mirus). Expression of GFP was detected by fundus opthalmoscopy 48 hours and 60 hours after injection. Animals were sacrificed at either 48 hours or 60 hours post-injection. The eyes were enucleated and fixed in 4% paraformaldehyde, and were prepared either as flat mounts or were processed into 10 micron cryosections for fluorescent microscopy.

No GFP fluorescence was detectable by opthalmoscopy in the eyes which received the siRNA targeted to GFP mRNA in 4 out of 5 mice, whereas GFP fluorescence was detectable in the contralateral eye which received the non-specific control siRNA. A representative flat mount analyzed by fluorescence microscopy showed a lack of GFP fluorescence in the eye which received GFP siRNA, as compared to an eye that received the non-specific control siRNA. Cryosections of another retina showed that the recombinant adenovirus efficiently targets the RPE cells, and when the adenovirus is accompanied by siRNA targeted to GFP mRNA, expression of the GFP transgene is halted.

While there is some GFP fluorescence detectable by fluorescence microscopy in eyes that received siRNA targeted to GFP mRNA, the fluorescence is greatly suppressed as compared to controls that received non-specific siRNA. These data demonstrate that functional siRNA can be delivered in vivo to RPE cells.

Example 5

In Vivo Expression and siRNA-Induced RNAi Degradation of Human VEGF in Murine Retinas In order to demonstrate that siRNA targeted to VEGF functioned in vivo, an exogenous human VEGF expression cassette was delivered to mouse RPE cells via an adenovirus by subretinal injection, as in Example 4. One eye received Cand5 siRNA, and the contralateral eye received siRNA targeted to GFP mRNA. The animals were sacrificed 60 hours post-injection, and the injected eyes were removed and snap frozen in liquid N2 following enucleation. The eyes were then homogenized in lysis buffer, and total protein was measured using a standard Bradford protein assay (Roche, Germany). The samples were normalized for total protein prior to assaying for human VEGF by ELISA as described in Example 1.

Figure 4:
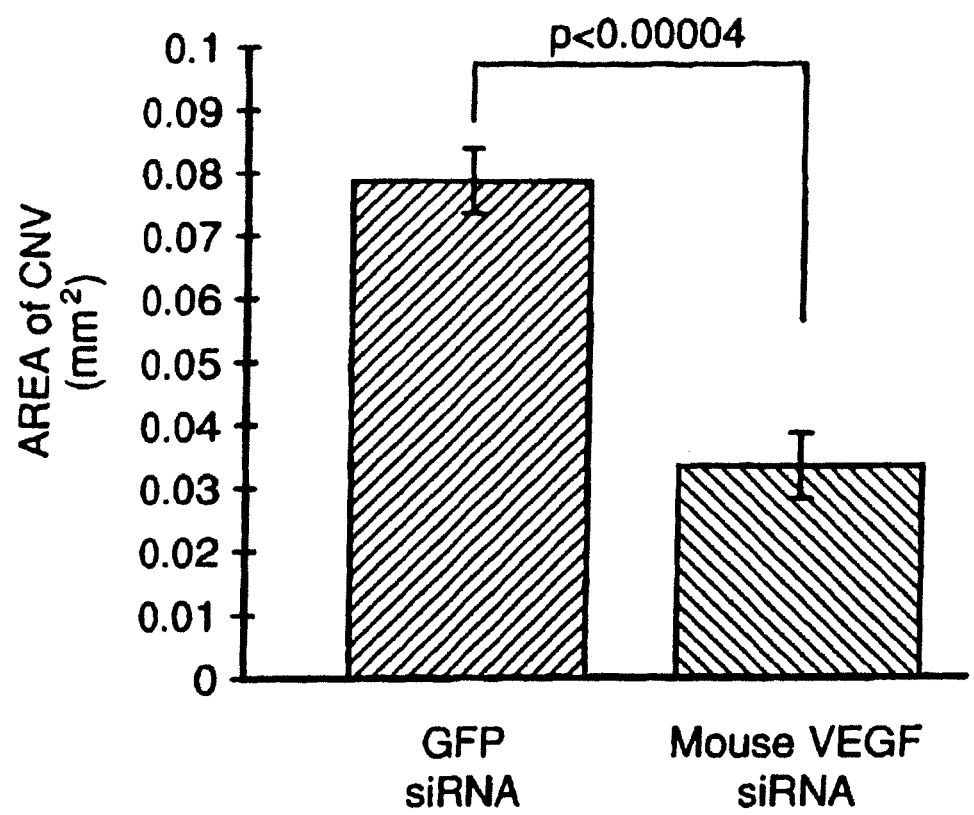
FIG. 4 is a histogram showing the mean area (in $mm^2$) of laser-induced CNV in control eyes given subretinal injections of GFP siRNA (N=9; "GFP siRNA"), and in eyes given subretinal injections of mouse VEGF siRNA (N=7; "Mouse VEGF siRNA"). The error bars represent the standard error of the mean.

The expression of VEGF was somewhat variable from animal to animal. The variability of VEGF levels correlated well to those observed in the GFP experiments of Example 4, and can be attributed to some error from injection to injection, and the differential ability of adenovirus to delivery the target gene in each animal. However, there was a significant attenuation of VEGF expression in each eye that received VEGF siRNA, as compared to the eyes receiving the non-specific control siRNA (FIG. 4). These data indicate that the Cand5 siRNA was potent and effective in silencing human VEGF expression in murine RPE cells in vivo.

Example 6

Inhibition of Choroidal Neovascularization in the Mouse CNV Model

There is evidence that choroidal neovascularization in ARMD is due to the upregulation of VEGF in the RPE cells. This human pathologic condition can be modeled in the mouse by using a laser to burn a spot on the retina ("laser photo-coagulation" or "laser induction"). During the healing process, VEGF is believed to be up-regulated in the RPE cells of the burned region, leading to re-vascularization of the choroid. This model is called the mouse choroidal neovascularization ("CNV") model.

For rescue of the mouse CNV model, a mouse siRNA was designed that incorporated a one nucleotide change from the human "Cand5" siRNA from Example 1. The mouse siRNA specifically targeted mouse VEGF mRNA at the sequence AAACCUCACCAAAGCCAGCAC (SEQ ID NO: 80). Other siRNA that target mouse VEGF were also designed and tested. The GFP siRNA used as a nonspecific control in Example 1 was also used as a non-specific control here.

Twenty four hours after laser induction, one eye from each of eleven adult C57/Black6 mice (Jackson Labs, Bar Harbor, Me.) was injected subretinally with a mixture containing ~1×10$^8$ particles of adenovirus containing LacZ driven by the CMV promoter and 20 picomoles of siRNA targeting mouse VEGF conjugated with transit TKO reagent (Mirus), as in Example 4. As a control, contralateral eyes received a mixture containing ~1×10⁸ particles of adenovirus containing LacZ driven by the CMV promoter and 20 picomoles of siRNA targeting GFP conjugated with transit TKO reagent (Mirus).

Fourteen days after the laser treatment, the mice were perfused with fluorescein and the area of neovascularization was measured around the burn spots. Areas of the burn spots in the contra-lateral eye were used as a control. The site of neovascularization around the burn spots in animals that received siRNA targeting mouse VEGF was, on average, ¼ the area of the control areas. These data support the use of VEGF-directed siRNA (also called "anti-VEGF siRNA") for therapy of ARMD.

Example 7

Generation of an Adeno-Associated Viral Vector for Expression of siRNA

A "cis-acting" plasmid for generating a recombinant AAV vector for delivering an siRNA was generated by PCR based subcloning, essentially as described in Samulski R et al. (1987), supra. The cis-acting plasmid was called "pAAV-siRNA."

Figure 5:
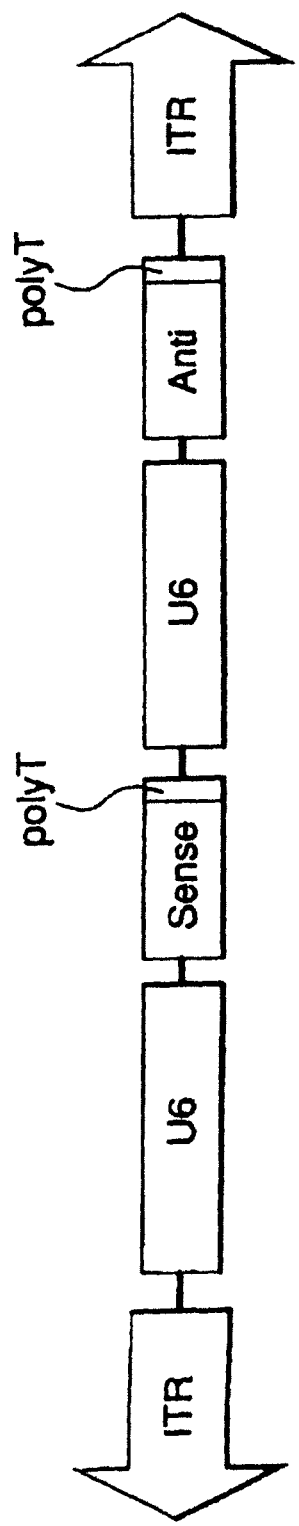
FIG. 5 is a schematic representation of pAAVsiRNA, a cis-acting plasmid used to generate a recombinant AAV viral vector of the invention. "ITR": AAV inverted terminal repeats; "U6": U6 RNA promoters; "Sense": siRNA sense coding sequence; "Anti": siRNA antisense coding sequence; "PolyT": polythymidine termination signals.

The rep and cap genes of psub201 were replaced with the following sequences in this order: a 19 nt sense RNA strand coding sequence in operable connection with a polyT termination sequence under the control of a human U6 RNA promoter, and a 19 nt antisense RNA strand coding sequence in operable connection with a polyT termination sequence under the control of a human U6 RNA promoter. A schematic representation of pAAVsiRNA is given if FIG. 5.

A recombinant AAV siRNA vector was obtained by transfecting pAAVsiRNA into human 293 cells previously infected with E1-deleted adenovirus, as described in Fisher K J et al. (1996), supra. The AAV rep and cap functions were provided by a trans-acting plasmid pAAV/Ad as described in Samulski R et al. (1989), supra. Production lots of the recombinant AAV siRNA vector were titered according to the number of genome copies/ml, as described in Fisher K J et al. (1996), supra.

Example 8

VEGF-Directed siRNA Inhibits Experimental Choroidal Neovascularization

The ability of murine VEGF-directed siRNA to inhibit experimental laser-induced choroidal neovascularization (CNV) in mice was tested as follows.

The retinas of adult female C57BL/6 mice were laser photocoagulated using an 810 nm diode laser (75 um, 140 mw, 0.10 seconds) (OcuLight Six; IRIS Medical, Mountain View, Calif.). Three laser spots were applied to both eyes of each mouse. Thirty-six hours following laser photocoagulation, an siRNA targeted to mouse VEGF ("mVEGF1.siRNA") was delivered subretinally or intravitreally to one eye of each mouse. For subretinal injection, the siRNA was conjugated with Transit TKO transfection reagent (Mirus) and mixed with recombinant adenovirus (rAdenovirus). For intravitreal injection, the siRNA was delivered in the absence of transfection reagent and rAdenovirus. As a control, the contralateral eyes of each mouse received subretinal or intravitreal injections of identical formulations with an siRNA targeted to GFP ("GFP1.siRNA"), which has no homology to mouse VEGF.

Figure 6A:
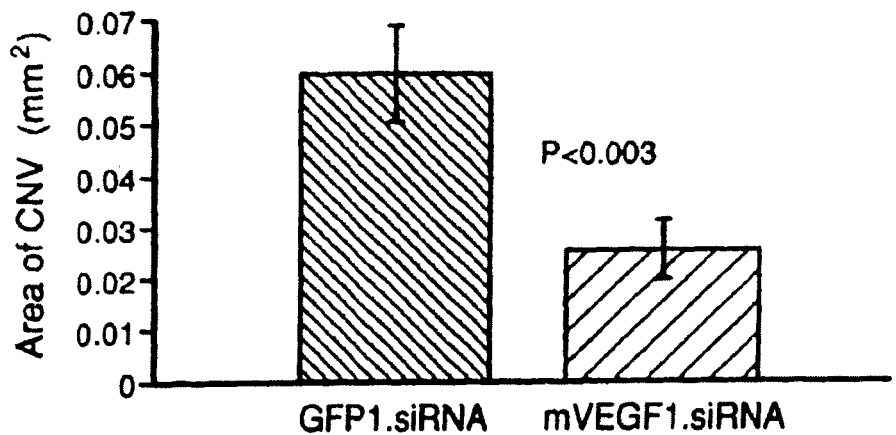
FIG. 6 shows histograms of the mean area (in $mm^2$) of laser-induced CNV in treatment in mouse eyes injected (A) subretinally or (B) intravitreally with a mouse anti-VEGF siRNA ("mVEGF1.siRNA") or control siRNA ("GFP1.siRNA"). The error bars represent the standard error of the mean. (C) is a histogram of the mean area (in $mm^2$) of laser-induced CNV in mouse eyes injected intravitreally with: phosphate-buffered saline with no siRNA at 1 day post-laser induction ("PBS"; CNV area measured at 14 days post-laser induction); control siRNA at 14 days post-laser induction ("GFP1.siRNA"; CNV area measured at 21 days post-laser induction); or a mouse anti-VEGF siRNA at 14 days post-laser induction ("mVEGF1.siRNA"; CNV area measured at 21 days post-laser induction). The error bars represent the standard error of the mean.
Figure 6B:
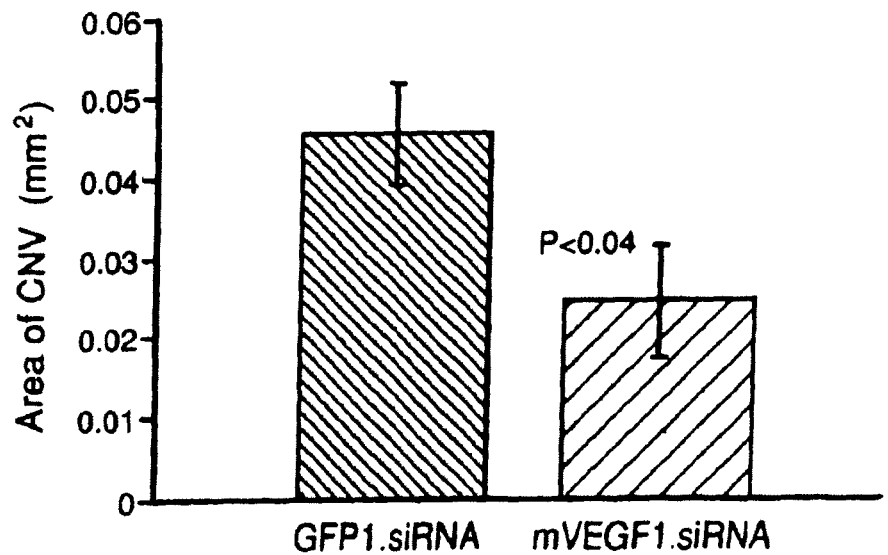

Fourteen days following laser treatment, all animals were perfused with high molecular weight FITC-dextran, choroidal flat mounts were prepared as described above, and the flat mounts were photographed and analyzed microscopically in a masked fashion. The area of CNV in each flat mount was measured with Openlab software (Improvision, Boston, Mass.). The mean areas of CNV in eyes treated with mVEGF1.siRNA were significantly smaller than those areas from GFP1.siRNA-treated eyes for both subretinal (FIG. 6A; $P<0.003$) and intravitreal (FIG. 6B; $P<0.04$) delivery.

In a second experiment, the retinas of adult female C57BL/6 mice were laser photocoagulated as described above, and the animals were divided into control and test groups. One day following laser photocoagulation, phosphate buffered saline was delivered intravitreally to the animals of the control group, which were perfused with dextran-fluorescein 14 days after laser treatment. Choroidal flat mounts were then prepared and the areas of CNV in each flat mount were measured as above.

Fourteen days following laser photocoagulation, mVEGF1.siRNA was delivered by intravitreal injection into one eye of each mouse in the test group. Contralateral eyes were injected with GFP1.siRNA as a control. The test group animals were perfused with high molecular weight dextran-fluorescein 21 days after laser treatment. Choroidal flat mounts were then prepared and the areas of CNV in each flat mount were measured, as above.

Figure 6C:
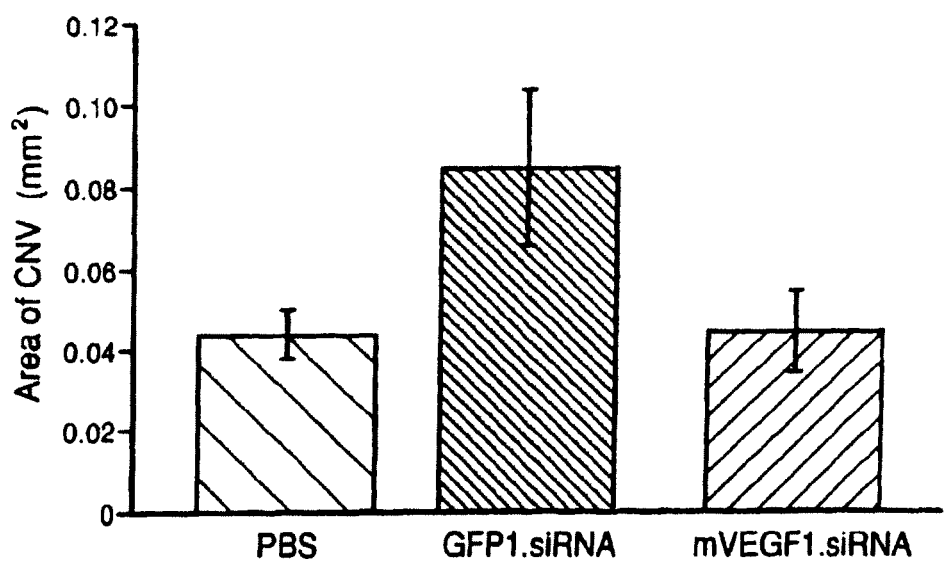

In this latter experiment, the anti-VEGF siRNA was administered during CNV growth, as opposed to before CNV growth, and thus is more representative of the condition of human patients presenting with wet AMD. As can be seen from FIG. 6, the mean areas of CNV in mVEGF1.siRNA-treated eyes were significantly smaller than those areas measured in GFP1.siRNA-treated eyes (FIG. 6C; $P<0.05$). The mean areas of CNV in mVEGF1.siRNA-treated eyes at day 21 and control ("PBS") eyes at day 14 were not significantly different (FIG. 6C; $P=0.469$).

The results of these experiments indicate that age-related macular degeneration can be treated with anti-VEGF siRNA.

Example 9

In Vivo RNA Interference of Human VEGF Induced by Anti-VEGF siRNA in Murine RPE Cells The ability of Cand5 siRNA to induce RNAi of VEGF in vivo over time was evaluated as follows.

AAV.CMV.VEGF, which expresses human VEGF from an adeno-associated viral vector, was generously provided by Dr. A. Auricchio. AAV.CMV.VEGF was injected subretinally and bilaterally in eyes of five C57B1/6 mice. Twenty-eight days after injection of AAV.CMV.VEGF, Cand5 siRNA was delivered by intravitreal injection into one eye and control GFP1.siRNA was delivered by intravitreal injection in the contralateral eye of each animal.

At day 0 (pre-siRNA injection), and at 6, 10 and 14 days after siRNA injection, the mice were sacrificed and the eyes were snap frozen in liquid nitrogen following enucleation. The eyes were then homogenized in lysis buffer (Roche, Basel, Switzerland), and total protein was measured using a Bradford assay, as in Example 5 above. Two mice were used for the 0 day time point (n=2), and three mice each were used for the 6, 10 and 14 day time points (n=3). The samples were normalized for total protein prior to assaying for human VEGF by ELISA, according to the manufacturer's recommendations (R&D systems, Minneapolis, Minn.). Percent of VEGF (% VEGF) for each mouse was calculated as the concentration of VEGF ("[VEGF]") in the eye injected with Cand5 divided by the [VEGF] in the eye injected with GFP1.siRNA, multiplied by 100.

Figure 7:
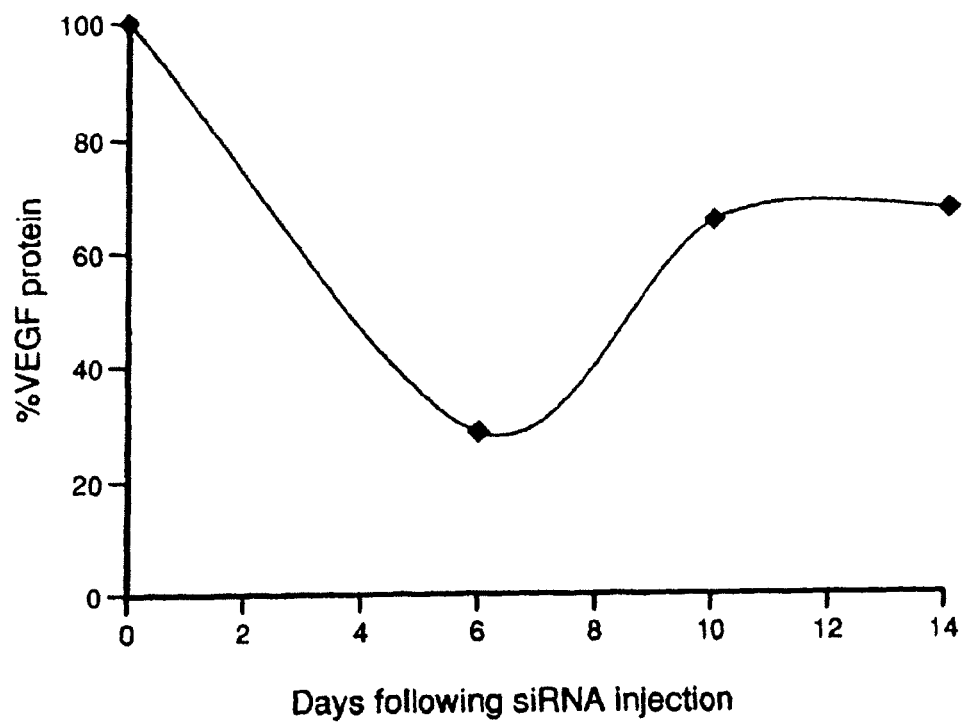
FIG. 7 is a graph of the percent of VEGF ("% VEGF") protein in mouse eyes injected sub-retinally with human anti-VEGF siRNA ("Cand5") and control siRNA ("GFP1.siRNA") at 0 (n=2; pre-siRNA injection), 6 (n=3), 10 (n=3) and 14 (n=3) days post-injection. % VEGF=([VEGF] in the Cand5 eye/[VEGF] in the GFP1.siRNA eye)*100.

As can be seen from FIG. 7, a single injection of Cand5 induced an RNAi-mediated decrease in VEGF levels of approximately 70% by day 6 post-siRNA injection, with a reduction in VEGF production of approximately 35% continuing through at least day 14 post-siRNA injection. These results indicate that siRNA directed against human VEGF is capable of inducing RNAi of human VEGF in vivo for a sustained period of time.

Example 10

In Vivo RNA Interference of VEGF in Monkeys with Anti-VEGF siRNA

The objectives of this study were to determine the safety and efficacy of Cand5 when administered by single intravitreal injection to male cynomolgus monkeys following induction of CNV. Cand5 was administered in the vehicle control article to naive male cynomolgus monkeys in the following dose levels: 0 mg/eye (control), 0.07 mg/eye, 0.18 mg/eye, 0.35 mg/eye and, and 0.70 mg/eye.

CNV was induced by laser treatment to the maculae of both eyes of each animal, and the doses of Cand5 were given shortly following laser treatment. The animals were evaluated for changes in clinical signs, body weight and ocular condition (extensive ophthalmic examinations, electroretinography and tonometry). Fluorescein angiography was performed and blood samples were collected. At the end of the study (Day 44), all animals were euthanized and a complete gross necropsy was performed. Selected tissues were collected and preserved for histopathologic evaluation.

No adverse systemic or local (ocular) effects of Cand5 were detected when monkeys were administered a single intravitreal injection into both eyes at doses up to 0.70 mg/eye following laser lesioning of the macula and during subsequent development of CNV.

Example 11

In Vitro RNA interference of VEGF with Anti-VEGF siRNA in Human Embryonic Kidney 293 Cells Human embryonic kidney 293 cells (obtained from ATCC, Manassas, Va.) were cultured in Dulbecco's Modified Eagle Medium (DMEM; obtained from Cellgro, Herndon, Va.) with 10% fetal bovine serum (FBS; from JRH Biosciences, Lenexa, Kans.) and an antibiotic-antimycotic reagent, used for the prevention of cell culture growth contaminants (from Gibco, Carlsbad, Calif.).

siRNAs were synthesized by Integrated DNA Technologies (Coralville, Iowa). The siRNA target sequences are shown in Table 2. An additional siRNA was used in this study that targets the gene of enhanced green fluorescent protein (EGFP) as a negative control.

TABLE 2

| Name | GC Content | Nucleotide Start Site | Target Sequence 5'-3' |
|---|---|---|---|
| hVEGF#1 | 58% | 92 | aaggaggagggcagaatcatc (SEQ ID NO: 81) |
| hVEGF#2 | 42% | 124 | aagttcatggatgtctatcag (SEQ ID NO: 47) |

TABLE 2-continued

| Name | GC Content | Nucleotide Start Site | Target Sequence 5'-3' |
|---|---|---|---|
| hVEGF#3 | 58% | 162 | aatcgagaccctggtggacat (SEQ ID NO: 48) |
| hVEGF#4 | 42% | 301 | aacatcaccatgcagattatg (SEQ ID NO: 50) |
| hVEGF#5 | 58% | 338 | aaggccagcacataggagaga (SEQ ID NO: 52) |
| hVEGF#6 | 42% | 380 | aatgtgaatgcagaccaaaga (SEQ ID NO: 82) |
| hVEGF#7 | 37% | 396 | aaagaaagatagagcaagaca (SEQ ID NO: 56) |
| hVEGF#8 | 32% | 450 | aaagcatttgtttgtacaaga (SEQ ID NO: 83) |
| hVEGF#9 | 42% | 467 | aagatccgcagacgtgtaaat (SEQ ID NO: 84) |
| hVEGF#10 | 53% | 498 | aaacacacactcgcgttgcaa (SEQ ID NO: 85) |
| Cand5 | 63% | 328 | aaacctcaccaaggccagcac (SEQ ID NO: 51) | siRNA Transfection and Hypoxia Induction In Vitro. Human 293 cells were cultured in 24 well plates at 37° C. with 5% $CO_2$ overnight. The next day, transfections were performed when cells were about 50%-70% confluent. Cells were transfected with siRNAs directed against human VEGF. siRNAs were mixed in a CaPi reagent and added to 20 µl of 250 mM $CaCl_2$ solution. The siRNA/$CaCl_2$ mixture was added drop-wise to 20 µl of 2× Hanks Balanced Salt Solution (HBS), while mixing by vortex. The siRNA/$CaCl_2$/HBS complex was added directly to the medium in each well (300 µL/well). After a 4-hour incubation at 37° C., the medium was removed, and the cells were further incubated with 10% DMSO-containing serum-free medium (300 µL/well at room temperature for 1-2 minutes). This medium was then removed, and the cells were fed again with growth medium (500 µL/well). Negative controls included transfection reagent lacking siRNA and nonspecific siRNA (EGFP1 siRNA). For screening experiments siRNAs were used at a concentration of 25 nM. For dose response experiments, siRNAs were used at concentrations of 1 nM, 5 nM and 25 nM. Hypoxia was induced with desferrioxamine at a final concentration of 130 uM 4 hours after transfection was performed. Desferrioxamine mimics a hypoxic state, as it is proposed to disrupt normal oxygen-sensing pathways in mammalian cells by inhibiting heme-Fe2+ interactions.

VEGF Protein Quantification. Approximately 48 hours post transfection, the supernatant was removed from all wells and a human VEGF ELISA (R & D systems, Minneapolis, Minn.) was performed on the 293 cells as described in the Quantikine human VEGF ELISA protocol. VEGF-specific antibody was added to each well causing color development in proportion to the amount of VEGF bound to the plate. ELISA results were read on an AD340 plate reader at 450 nm (Beckman Coulter).

Figure 8:
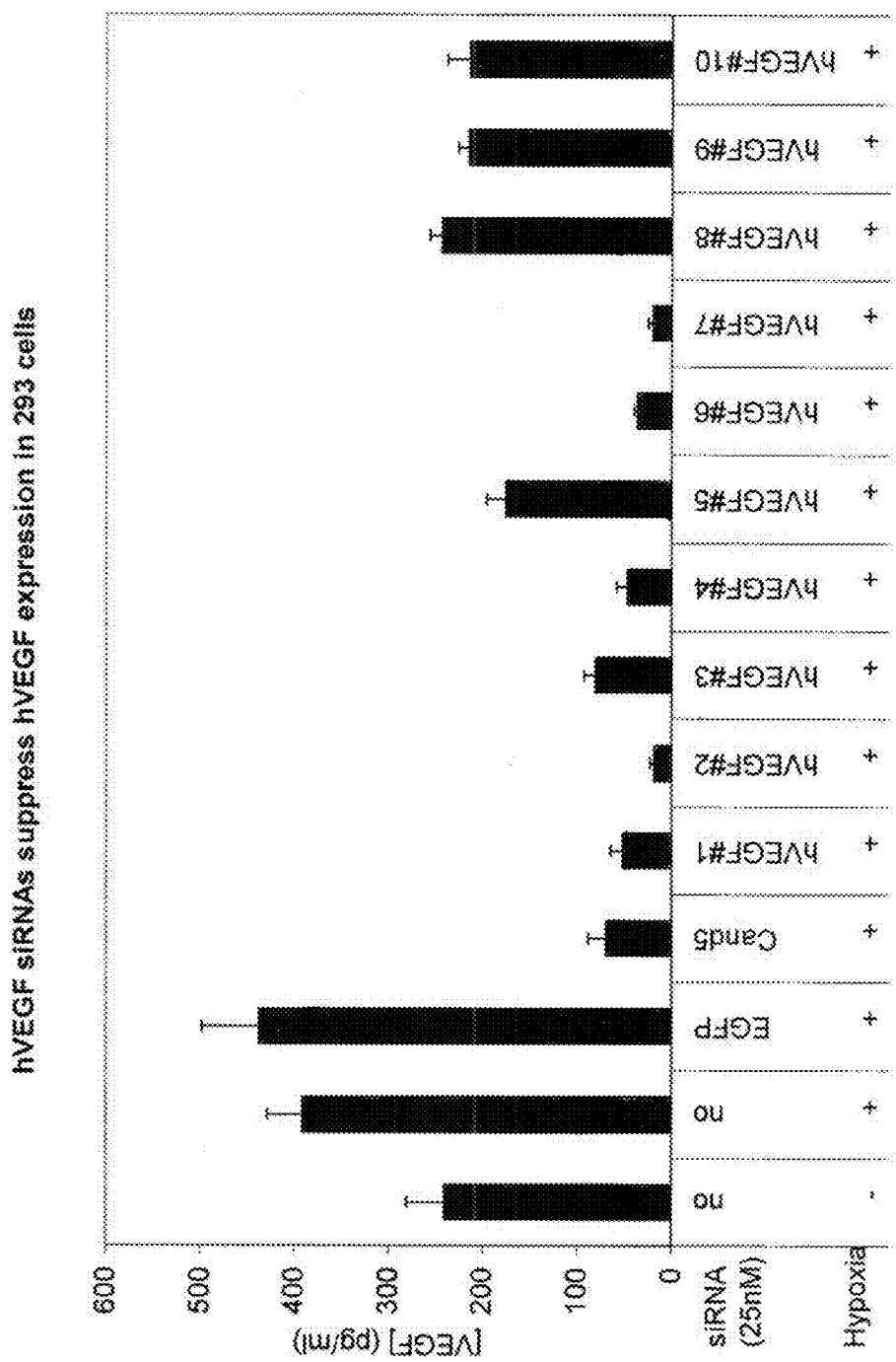
FIG. 8 is a graph of hVEGF protein levels in 293 cells transfected with transfected with human VEGF siRNAs, non-specific siRNA (EGFP siRNA) or mock transfections without siRNA.
Figure 9:
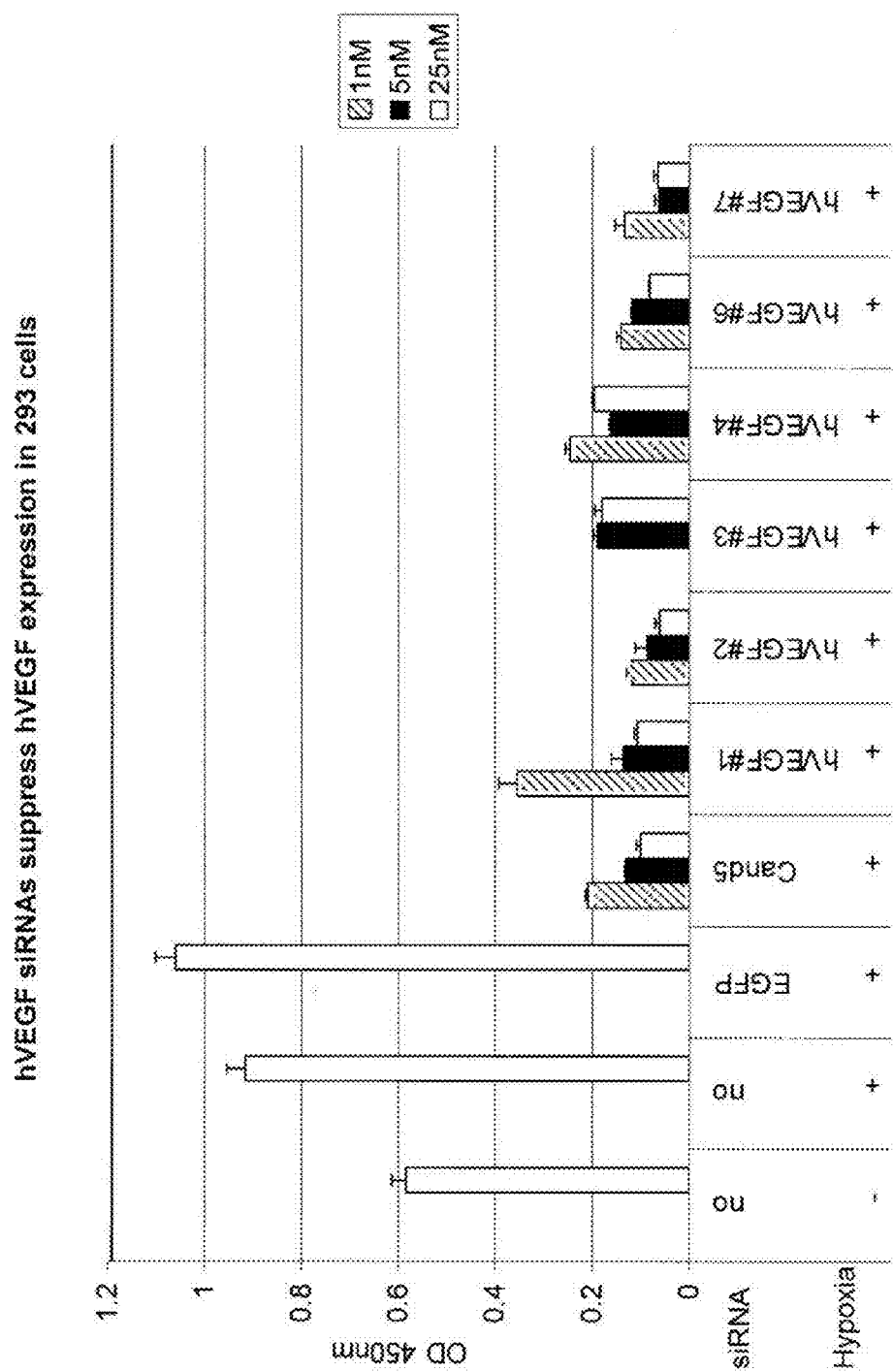
FIG. 9 is a graph of the dose response studies with Cand5 (bevasrianib), hVEGF#1, hVEGF#2, hVEGF#3, hVEGF#4, hVEGF#6 and hVEGF#7.

Results. Human VEGF siRNAs Suppresses Hypoxia-Induced Up-regulation of Human VEGF Protein in 293 Cells. Human VEGF was upregulated by the desferrioxamine-mediated induction of hypoxia. Readings of OD 450 nm reflected the human VEGF protein levels in cell samples. The hypoxia-induced increase of hVEGF protein levels were significantly reduced in cells transfected with all of the human VEGF siRNAs (FIG. 8). No effect on hVEGF levels were observed with transfections with nonspecific siRNA (EGFP siRNA) or mock transfections without siRNA. Dose response studies were performed on Candy, hVEGF#1, hVEGF#2, hVEGF#3, hVEGF#4, hVEGF#6 and hVEGF#7 (FIG. 9).

Example 12

In Vitro RNA Interference of VEGF isoforms $VEGF_{165b}$ has been identified as an endogenous anti-angiogenic VEGF isoform. siRNA were designed to selectively inhibit certain VEGF isoforms, such as $VEGF_{165}$, but spare $VEGF_{165b}$.

Methods: ARPE19 cells were seeded in 24 well plates (50,000 cells per well). Eighteen to twenty-four hours post-seeding, cells were 50-75% confluent and used for transfection. Fourteen human VEGF-A specific siRNAs were designed and tested. Cells were transfected with the siRNAs (25 nM) using Ribojuice™ siRNA Transfection Reagent (Novagen) following the manufacturer's protocol. Specifically, for a single well of cells, 40.5 µL serum free OPTI-MEM was pipetted into an eppendorf tube then 2 µt of Ribojuice was added to the OPTI-MEM. The solution was mixed by gentle vortexing and centrifuged briefly to collect contents at bottom of the tube and incubated at room temperature for 5 min. siRNA (7.5 µL of a 1 µM stock) was added to the Ribojuice/medium mix and gently mixed and briefly centrifuged to collect contents at the bottom of the tube. The mixture was incubated at room temperature for 15 minutes. During the incubation, media was removed from cells and replaced with 250 µL of fresh complete ARPE19 growth media (DMEM/F12; 10% FBS, 1% penicillin/streptomycin). After the 15 minute incubation the siRNA/Ribojuice/medium mixture (50 µL) was added dropwise to the cells. The final concentration of siRNA in the 300 µL volume was 25 nM. Cells were maintained at 37° C., 5% $CO_2$ for 24 hours. In additional experiments, reactions were scaled up to transfect cells in triplicate wells with each siRNA. 24 hours post-transfection, the transfection mixture was removed and the cells were treated with 500 µLs of serum free DMEM/F12, DMEM/F12 containing 10 ng/mL human recombinant TGF-βII or DMEM/F12 containing 10 ng/mL TGFβII and 5 µg/mL cycloheximide. The cells were returned to 37° C. and 5% $CO_2$ for an additional 24 hours. Afterwards, the media was removed from the cells and analyzed for protein expression by ELISA (Quantikine human VEGF ELISA kit (R&D Systems)). Media was removed from cells and collected in eppendorf tubes and placed on ice and immediately analyzed for VEGF protein via ELISA, or stored at −80° C. and analyzed for VEGF protein at a later time point.

Based on these results, a select number of siRNA candidates were put through an additional transfection screen. Cells were collected, RNA extracted, and semi-quantitative RT-PCR was performed to determine the siRNAs' inhibitory effect on $VEGF_{165}$, $VEGF_{165b}$, $VEGF_{121}$ and $VEGF_{189}$. GAPDH housekeeping gene expression was used as a control. Specifically, after removing the media from the wells, 200 µLs of lysis/binding solution from the RNAqueous Kit (Ambion) was added to each well. RNA was quantified via spectrophotometry (OD 260 nM). The lysed cells were collected and RNA was extracted following the manufacturer's protocol. RNA was reverse transcribed using SuperScript™ III Reverse Transcriptase (Invitrogen) according to the manufacturer's protocol. cDNA was analyzed for GAPDH, $VEGF_{165}$, $VEGF_{165b}$, $VEGF_{121}$ and $VEGF_{189}$ using PCR. Primers used for PCR are shown in Table 3.

TABLE 3

| Primer Name | Description | Sequence 5'-3' | |
|---|---|---|---|
| P121 | Reverse primer VEGF121 | GGCTTGTCACATTTTTCTTG | (SEQ ID NO: 131) |
| P165 | Reverse primer VEGF165 | CCCACAGGGATTTTCTTGTC | (SEQ ID NO: 132) |
| P189 | Reverse primer VEGF189 | CTTTCCCTTTCCTCGAACTG | (SEQ ID NO: 133) |
| hVEGF-E | Forward primer used for VEGF121, VEGF165 & VEGF 189 | GCTACTGCCATCCAATCGAG | (SEQ ID NO: 134) |
| P165bR | Reverse primer for VEGF165b | GTCTTTCCTGGTGAGAGATC | (SEQ ID NO: 135) |
| hVEGF-A | Forward primer for VEGF165b | CTGTCTTGGGTGCATTGGAG | (SEQ ID NO: 136) |
| GAPDH-B | Reverse primer GAPDH | GAGGCAGGGATGATGTTCTG | (SEQ ID NO: 137) |
| GAPDH-A | Forward primer GAPDH | CATGGCAAATTCCATGGCAC | (SEQ ID NO: 138) |

For PCR analysis, 3 µL cDNA was combined with 1 µL of each appropriate forward (10 µM) and reverse primer (10 µM) primer and 45 µL of Platinum PCR Supermix (Invitrogen) such that the final concentration of each primer was 200 nM. The cDNA was amplified in a thermocycler with the following PCR conditions:

Step 1: 94° C. for 2 minutes
Step 2: 94° C. for 15 seconds
Step 3: 55° C. for 30 seconds
Step 4: 72° C. for 30 seconds
Step 5: Repeat steps 2-4 30 times for GAPDH, $VEGF_{165}$, $VEGF_{121}$ and $VEGF_{189}$ or 35 times for $VEGF_{165b}$
Step 6: 72° C. for 10 minutes
Step 7: 4° C.

PCR product was then visualized on a 2% agarose gel prepared in 1×TAE buffer.

Figure 12:
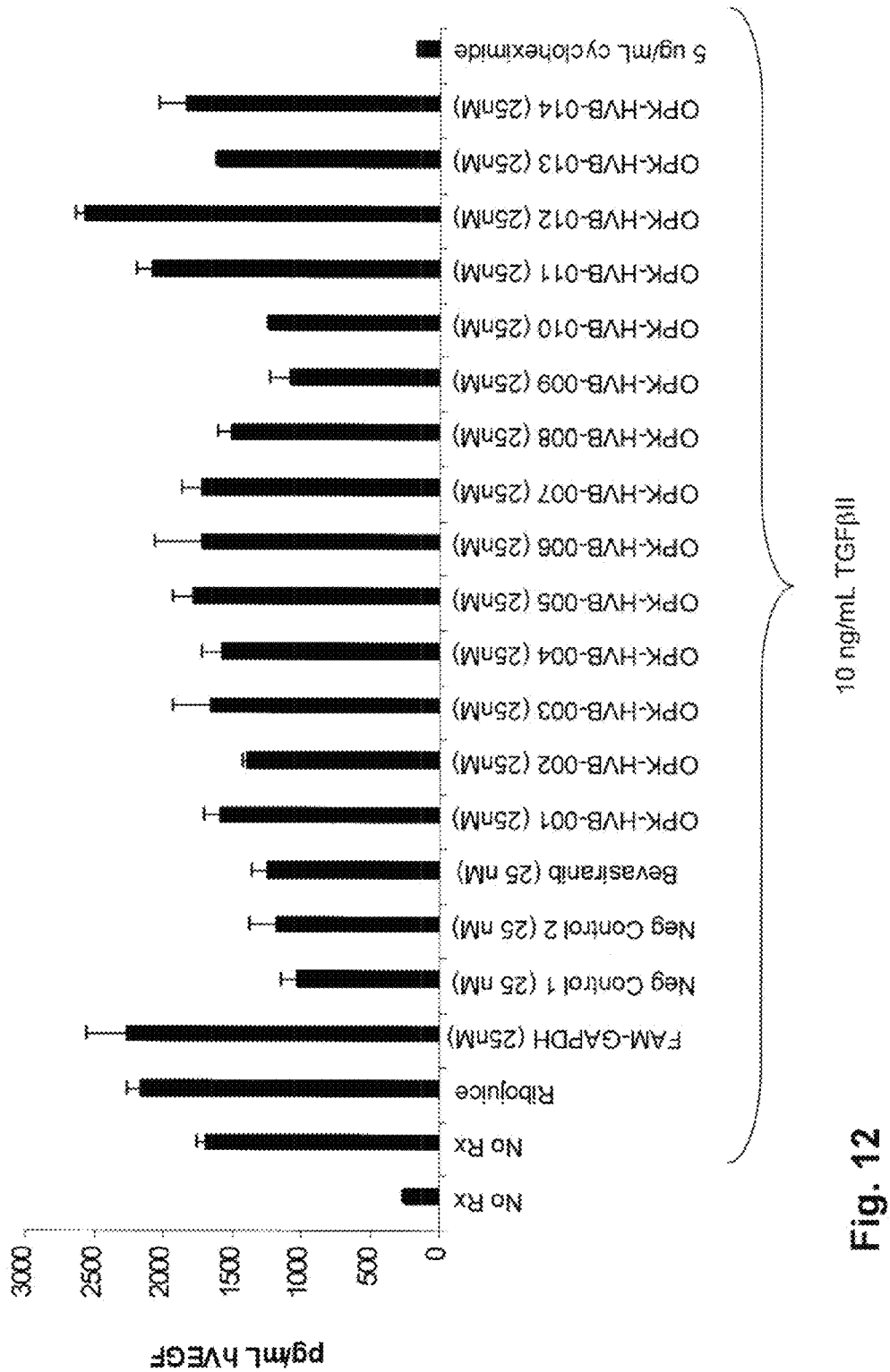
FIG. 12 depicts the amount of VEGF protein expressed for various siRNAs targeting the $VEGF_{165}$ exon 7/8 junction.
Figure 13:
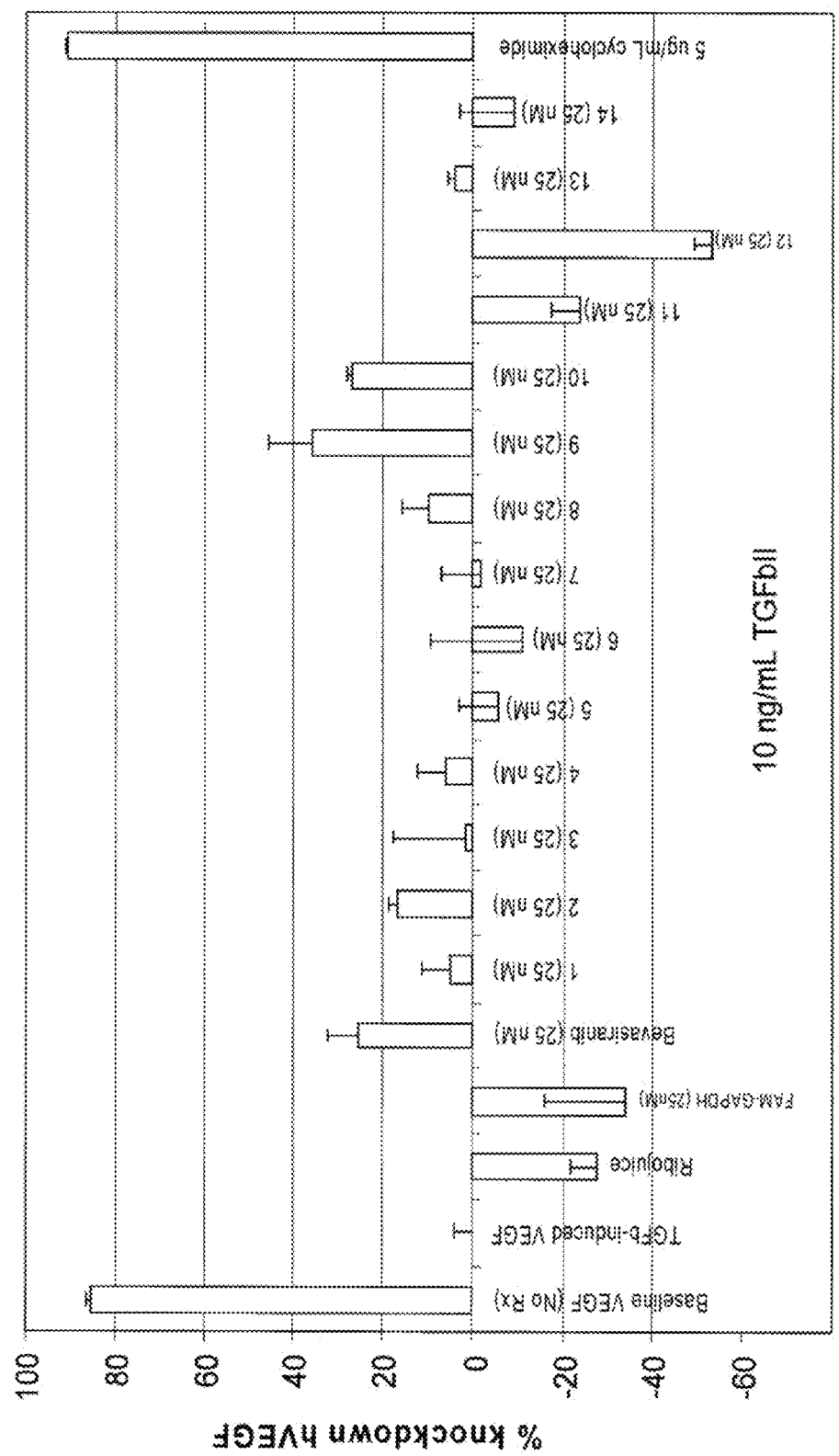
FIG. 13 depicts the percent knockdown of human VEGF protein for various siRNAs targeting the $VEGF_{165}$ exon 7/8 junction.
Figure 14:
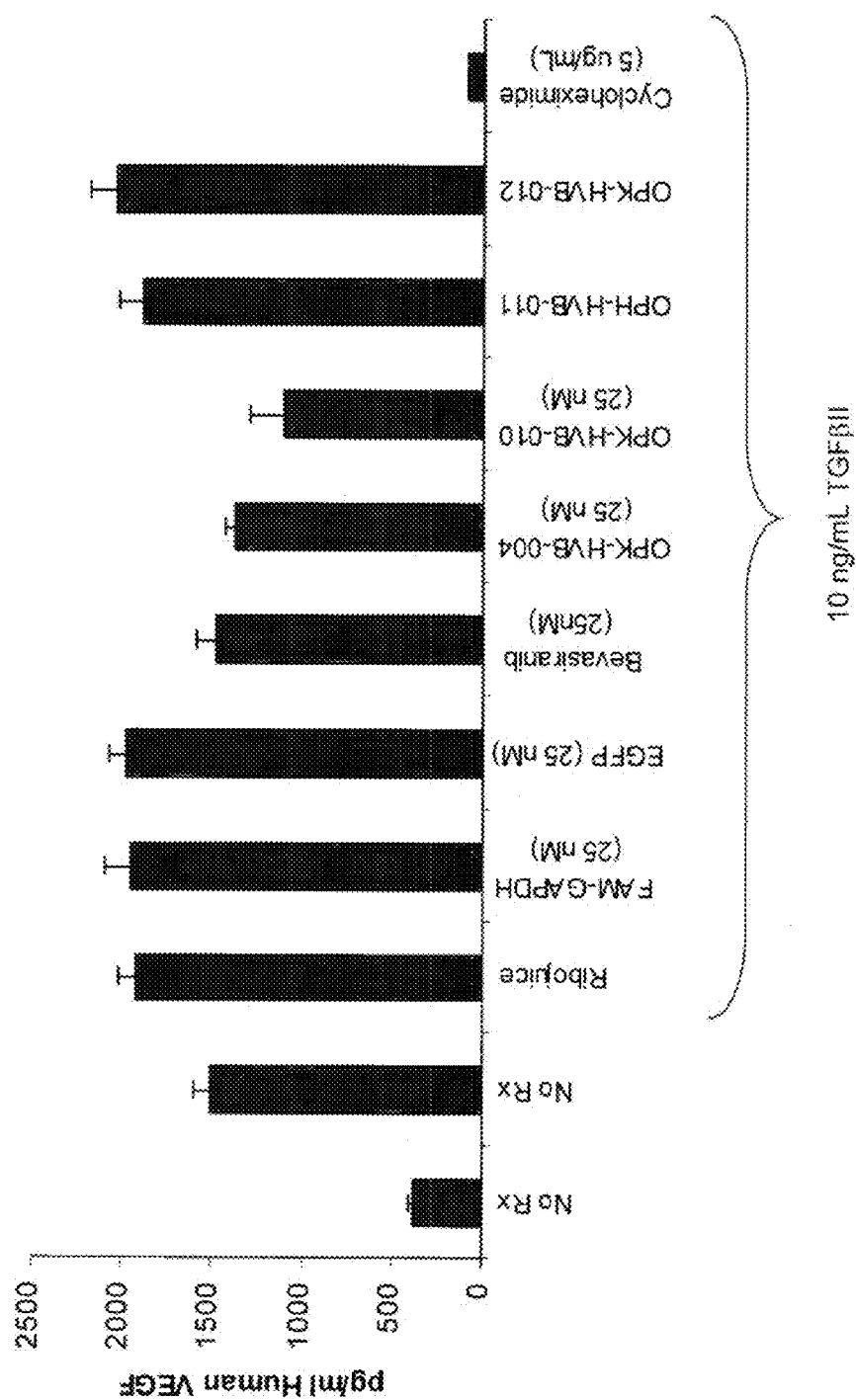
FIG. 14 depicts the amount of VEGF protein expressed for a secondary screen of siRNAs targeting the $VEGF_{165}$ exon 7/8 junction.
Figure 15:
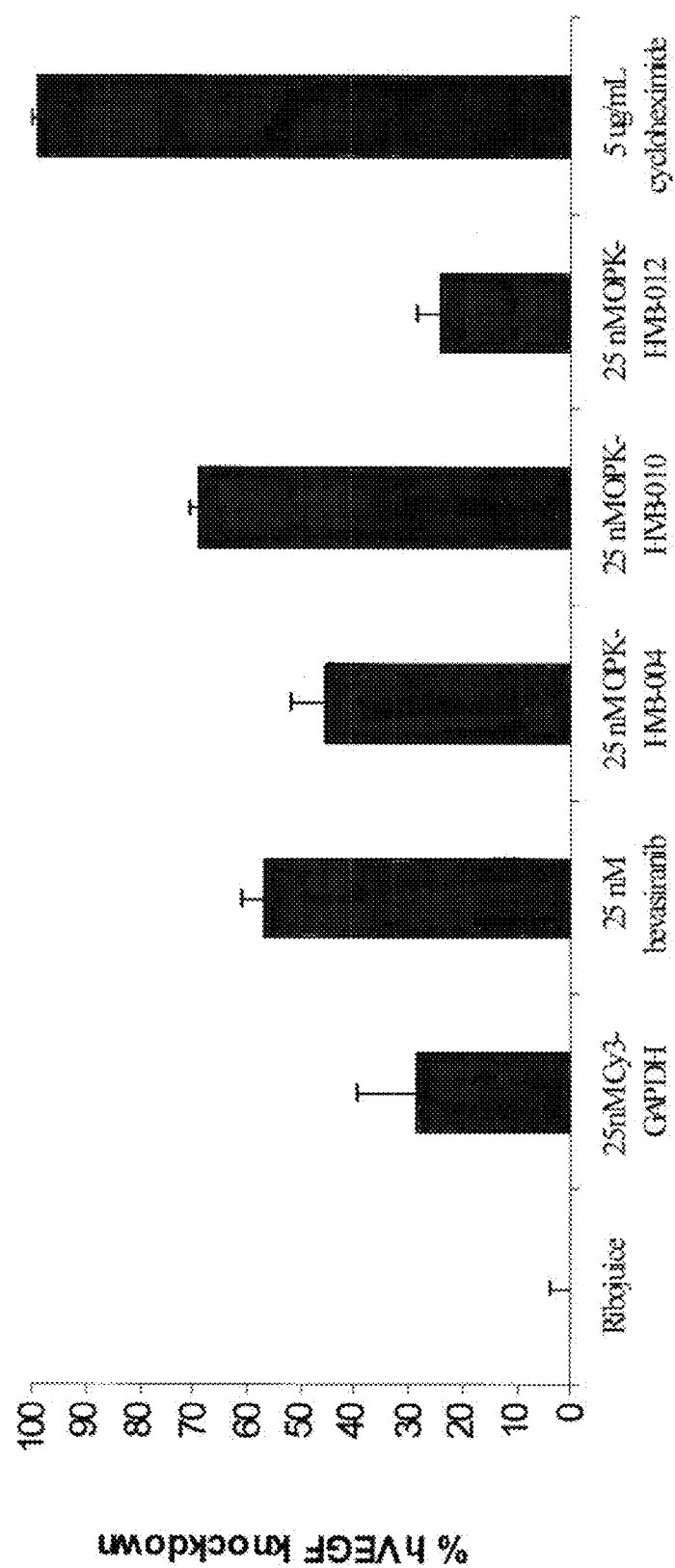
FIG. 15 depicts the percent knockdown of human VEGF protein for a secondary screen of siRNAs targeting the $VEGF_{165}$ exon 7/8 junction.

Results: Treatment of ARPE19 cells with TGFβII induced VEGF production in ARPE19 cells and ELISA results demonstrated several siRNA candidates inhibited the production of TGFβII-induced VEGF in ARPE19 cells. RT-PCR confirmed that 2 candidates inhibited production of VEGF$_{165}$, VEGF$_{121}$ and VEGF$_{189}$, but spared VEGF$_{165b}$. As shown in FIG. 12 (pg/mL hVEGF) and 13 (% knockdown hVEGF), VEGF siRNA candidates (Table 2) were screened for the ability to inhibit VEGF protein production by ARPE19 cells as tested by ELISA. Cells were treated with 10 ng/mL TGFβII to upregulate VEGF production. ELISA measured total VEGF protein and was not selective for any particular splice variant. Several candidates (OPK-HVB-004, OPK-HVB-010, and OPK-HVB-011) demonstrate an inhibitory effect and warranted further study. As shown in FIG. 14 (pg/mL hVEGF) and 15 (% knockdown hVEGF), a secondary screen of VEGF production using the same methods as in FIGS. 12 and 13 demonstrated that OPK-HVB-004 and OPK-HVB-010 inhibited VEGF protein production and warranted further investigation.

Figure 16:
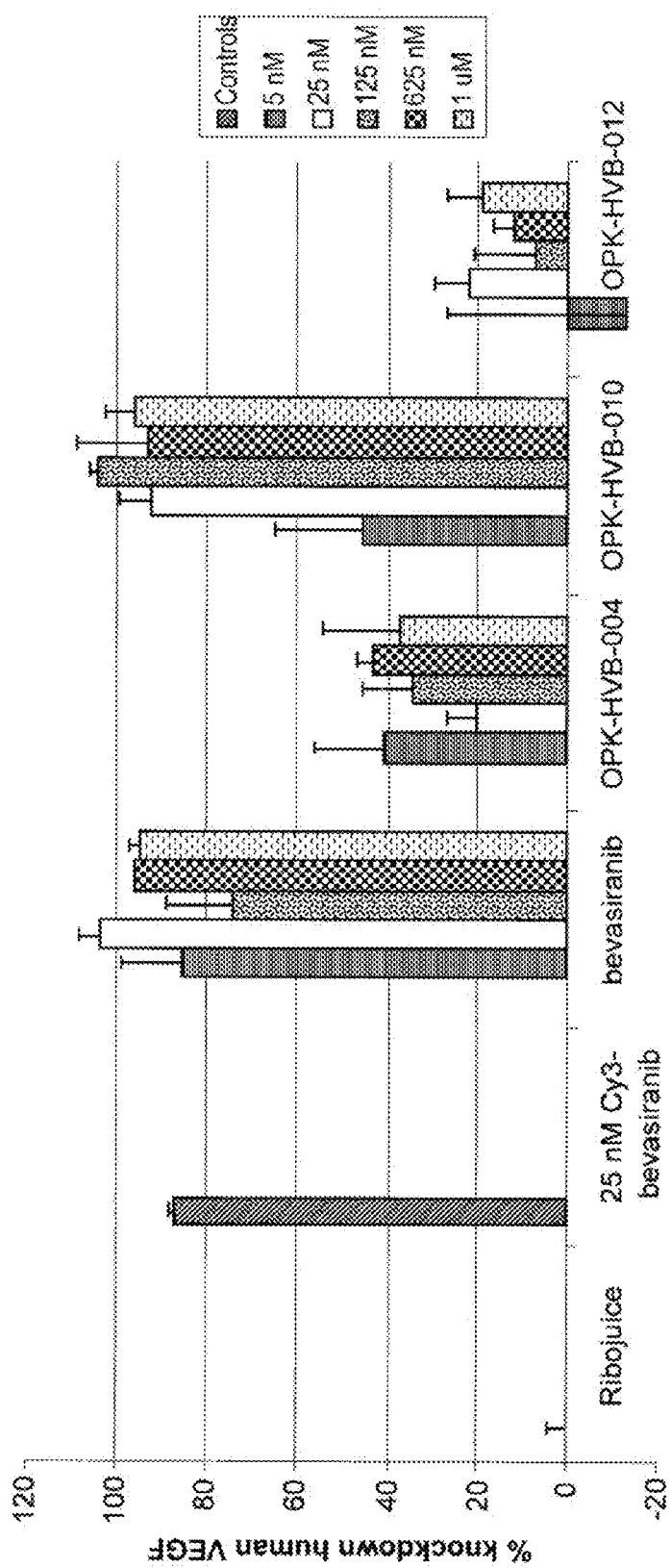
FIG. 16 depicts the percent knockdown of human VEGF protein for a secondary screen of siRNAs targeting the $VEGF_{165}$ exon 7/8 junction at varying concentrations.
Figure 24:
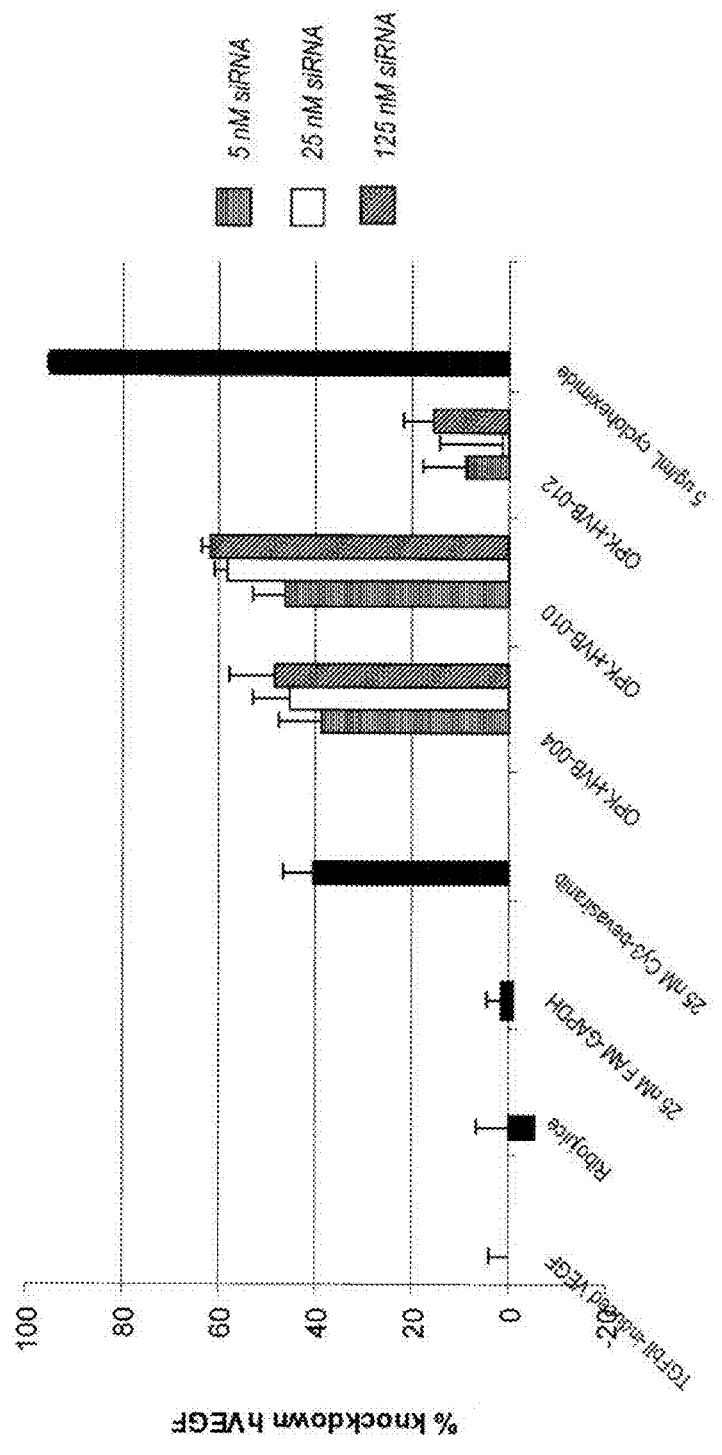
FIG. 24 depicts the effect of siRNAs on total VEGF protein secretion by ARPE19 cells.
Figure 27:
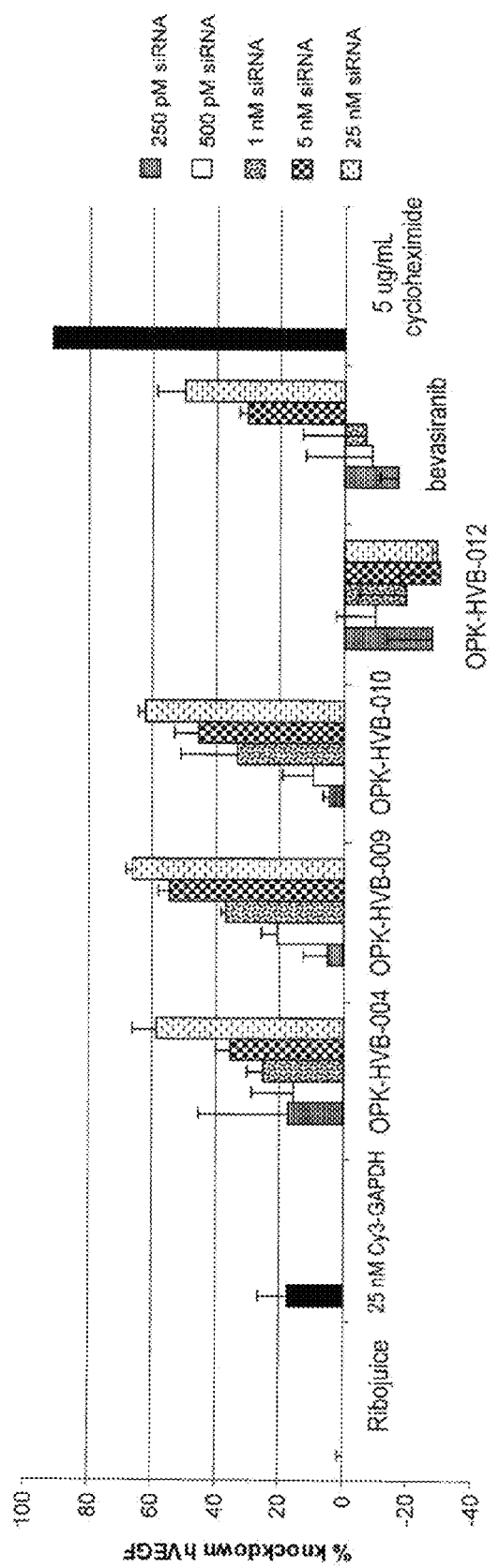
FIG. 27 depicts the effect of siRNAs on total VEGF protein secretion by ARPE19 cells.
Figure 28:
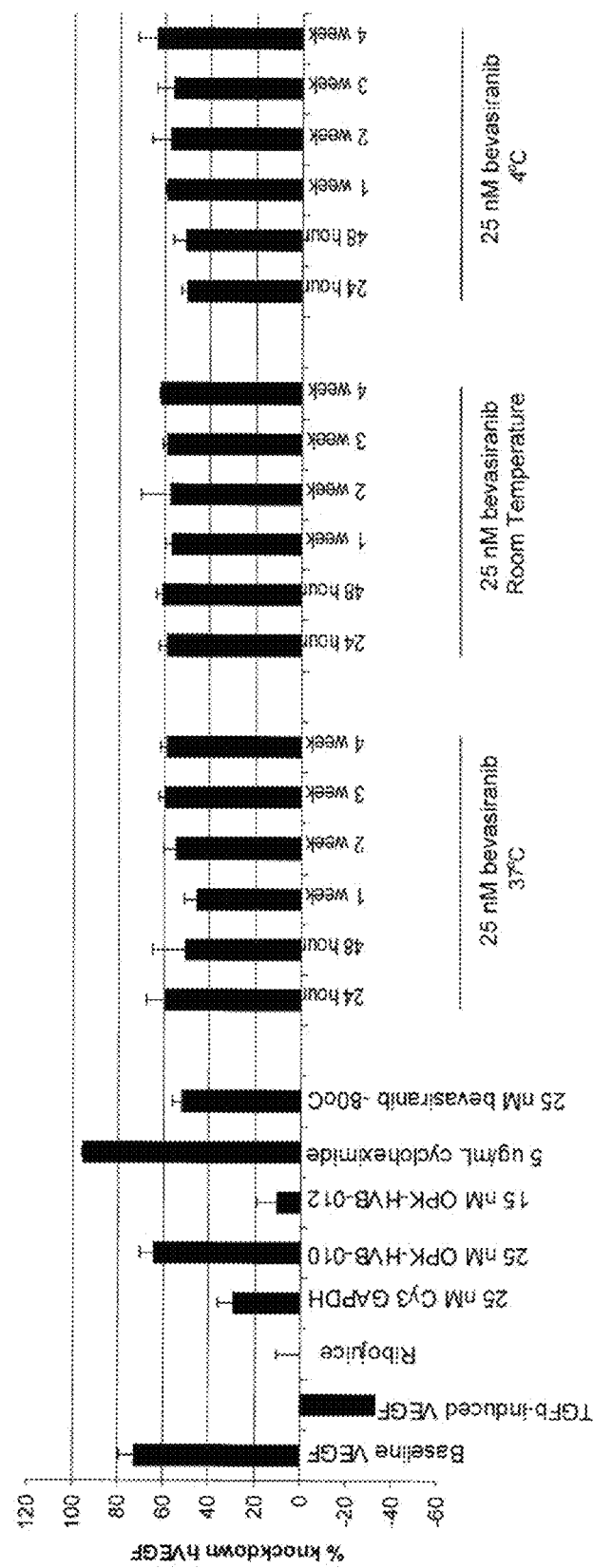
FIG. 28 depicts the stability of bevasiranib under different temperature conditions over time.
Figure 29:
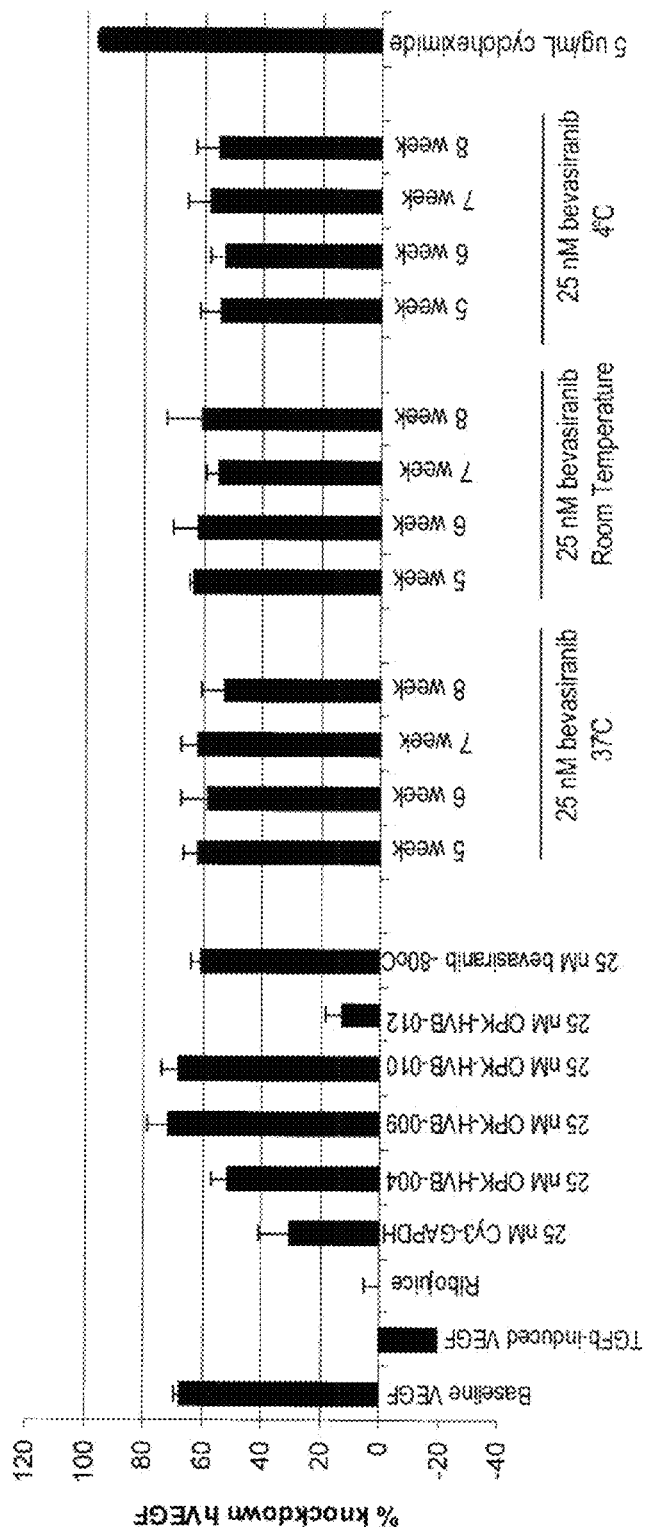
FIG. 29 depicts the stability of bevasiranib under different temperature conditions over time.
Figure 30:
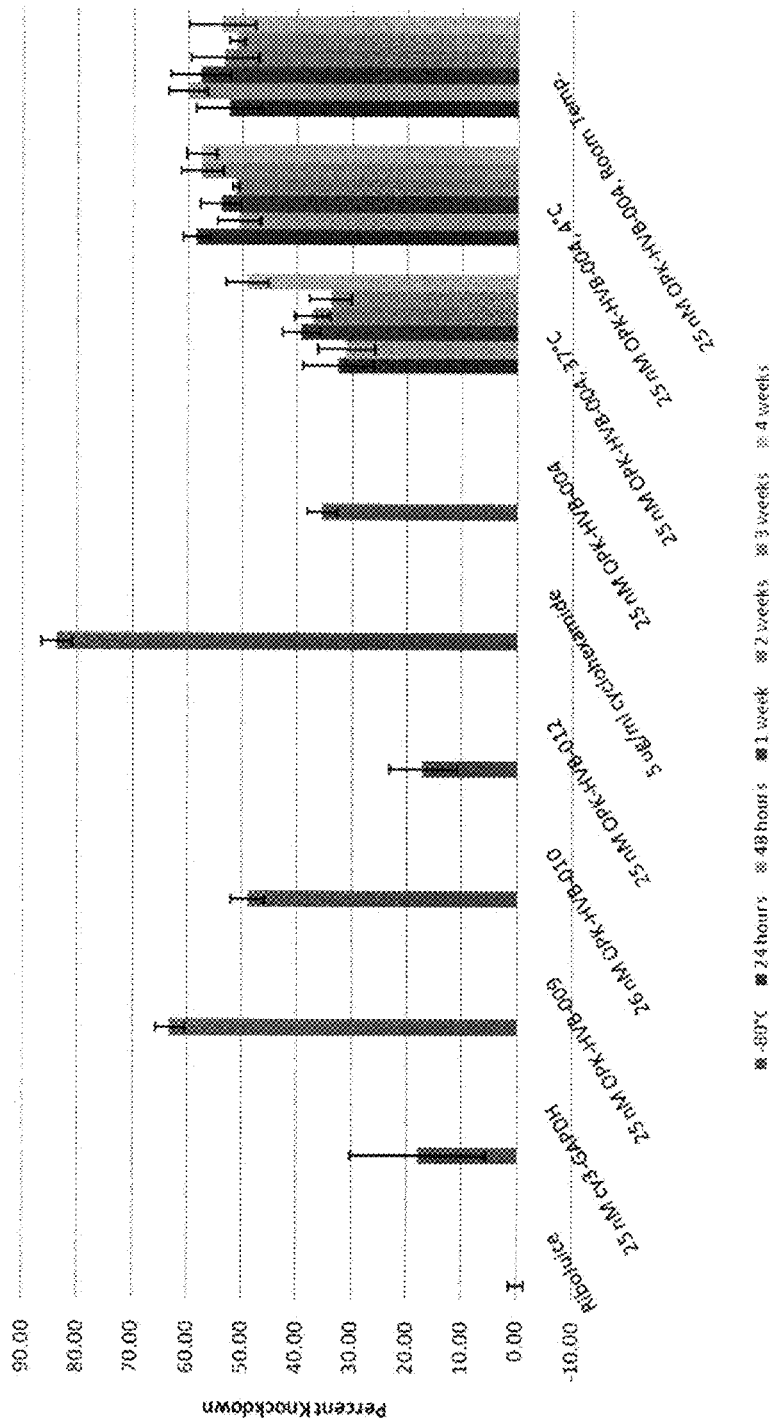
FIG. 30 depicts the stability of OPK-HVB-004 under different temperature conditions over time.
Figure 31:
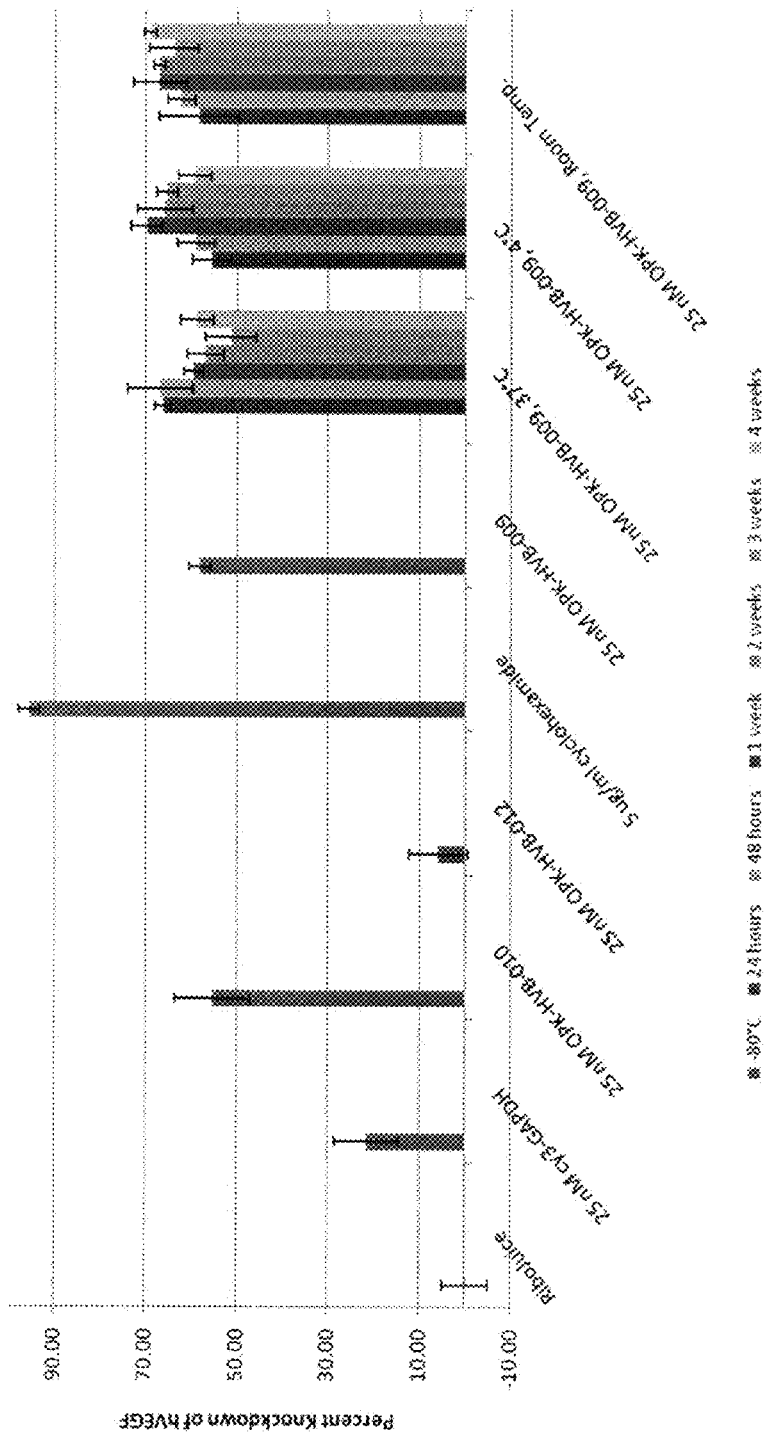
FIG. 31 depicts the stability of OPK-HVB-009 under different temperature conditions over time.

FIGS. 16, 24 and 27 demonstrate a dose response efficacy of human VEGF knockdown with several candidates (OPK-HVB-004, OPK-HVB-010, and OPK-HVB-012) at varying concentrations.

Figure 17:
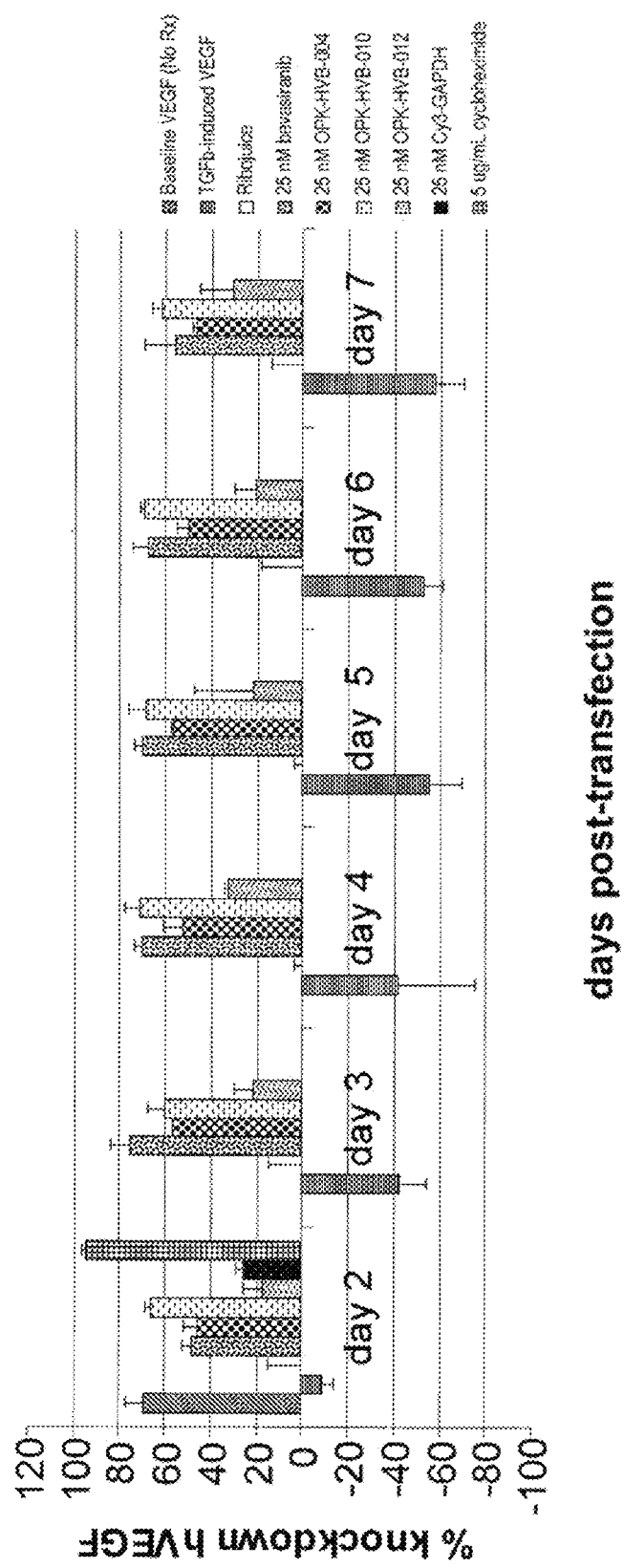
FIG. 17 depicts the percent knockdown of human VEGF protein over seven days for a secondary screen of siRNAs targeting the $VEGF_{165}$ exon 7/8 junction.

FIG. 17 demonstrates downregulation of human VEGF over one week (7 days) of several candidates (OPK-HVB-004, OPK-HVB-010, and OPK-HVB-012).

Figure 18:
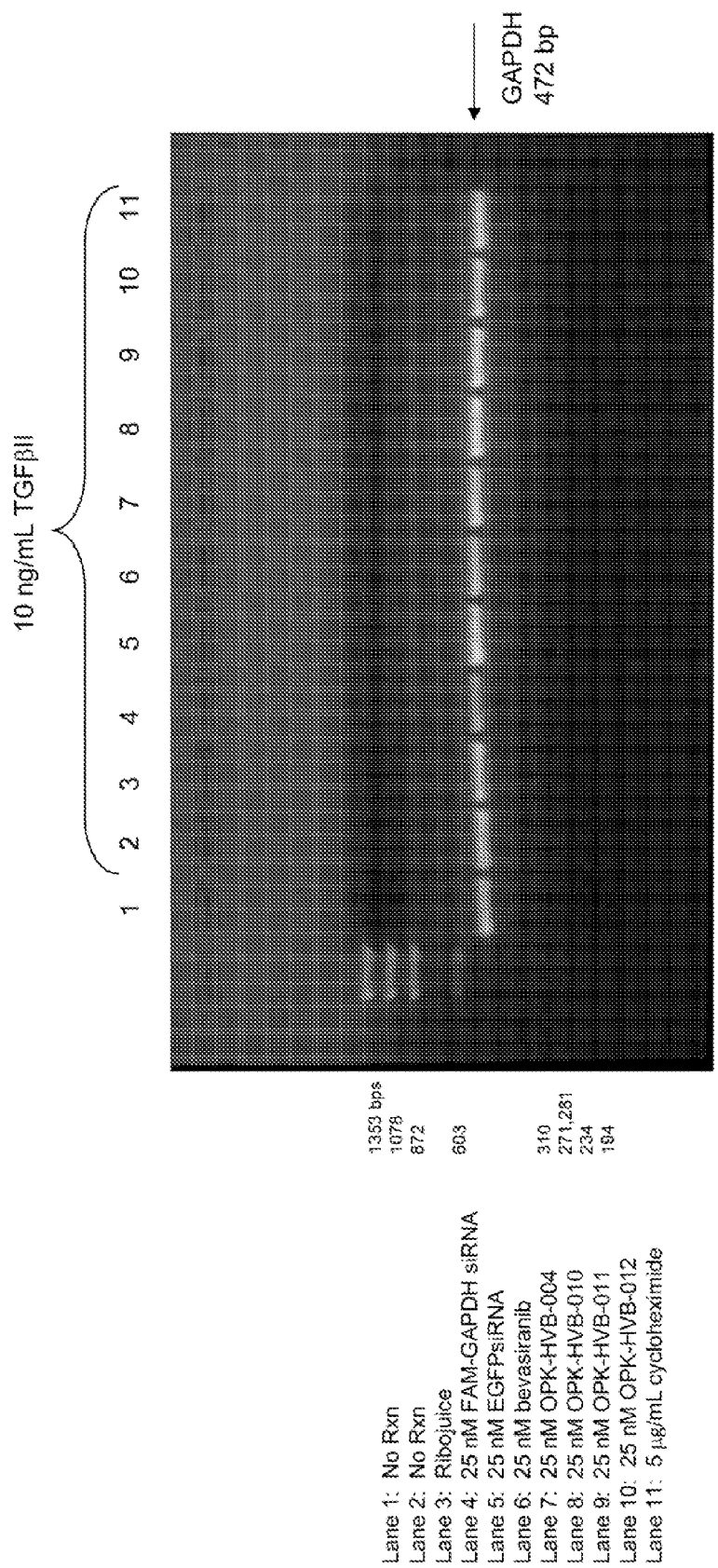
FIG. 18 depicts the effect of siRNA targeting the $VEGF_{165}$ exon 7/8 junction on GAPDH mRNA expression using RT-PCR.

As a control, GAPDH RT-PCR was performed on variously treated cells as shown in FIG. 18. Although the actual amount of RNA present was not quantified, the procedures are semi-quantitative when compared to the reference control lane 3. Specifically, downregulation of RNA production is demonstrated when a band appears fainter. In this experiment, samples in Lanes 2-11 were treated with 10 ng/mL TGFβII to upregulate the production of VEGF. The FAM-GAPDH siRNA downregulated GAPDH message (lane 4), while the other treatments have no effect on GAPDH mRNA, thus confirming that there is no variability in total RNA production in the treated cells.

Figure 19:
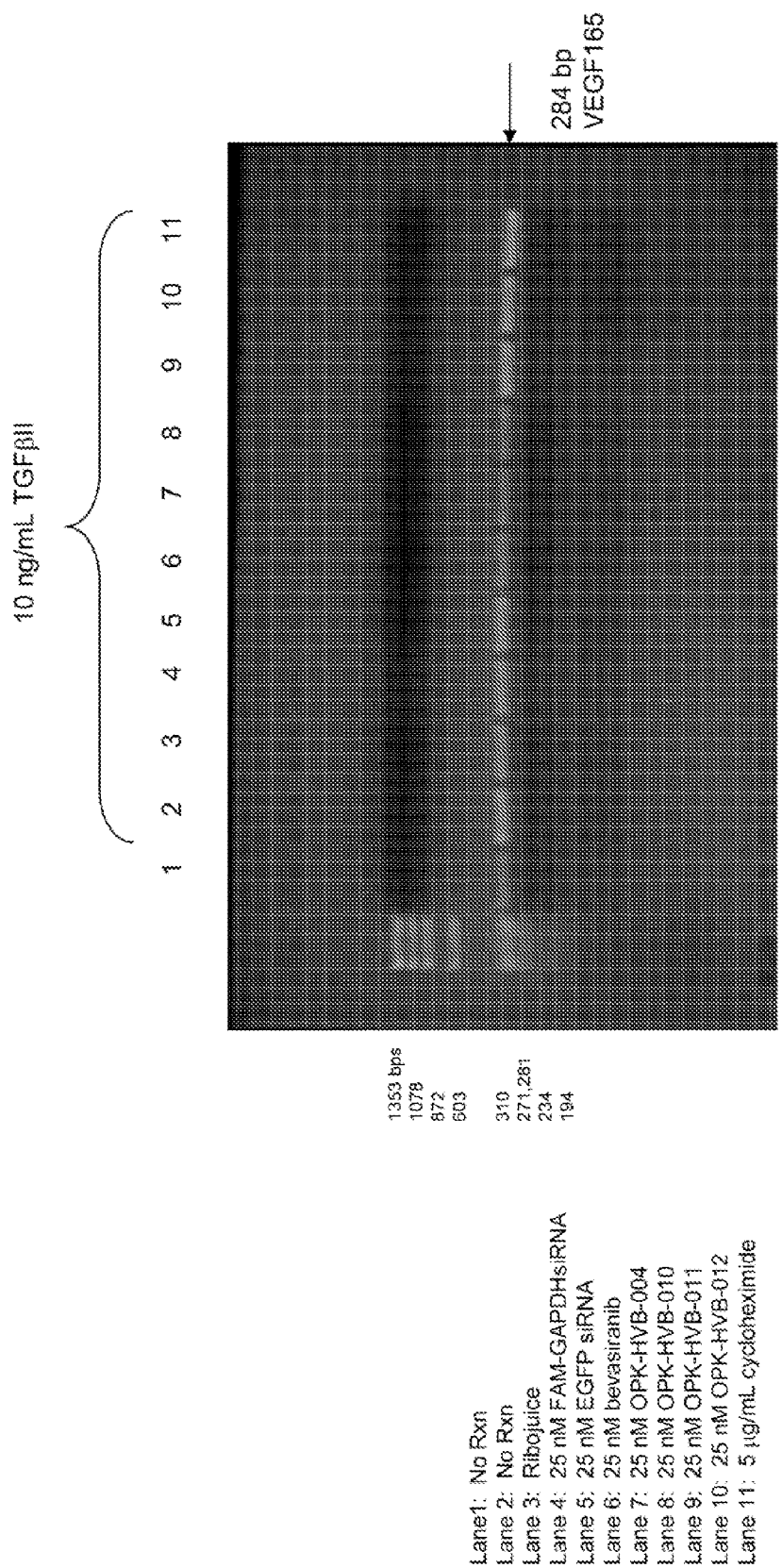
FIG. 19 depicts the effect of siRNA targeting the $VEGF_{165}$ exon 7/8 junction on $VEGF_{165}$ mRNA expression using RT-PCR.

VEGF$_{165}$ isoform RT-PCR was also performed on the treated cells as shown in FIG. 19. Samples in Lanes 2-11 were treated with 10 ng/mL TGFβII to upregulate the production of VEGF. 25 nM bevasiranib (lane 6), which is known to downregulate all VEGF isoforms, 25 nM OPK-HVB-004 (lane 7) and 25 nM OPK-HVB-010 (lane 8), down-regulated the production of VEGF$_{165}$ mRNA following induction with TGFβII (lane 2), as demonstrated by the bands being lighter than control in lane 3.

Figure 20:
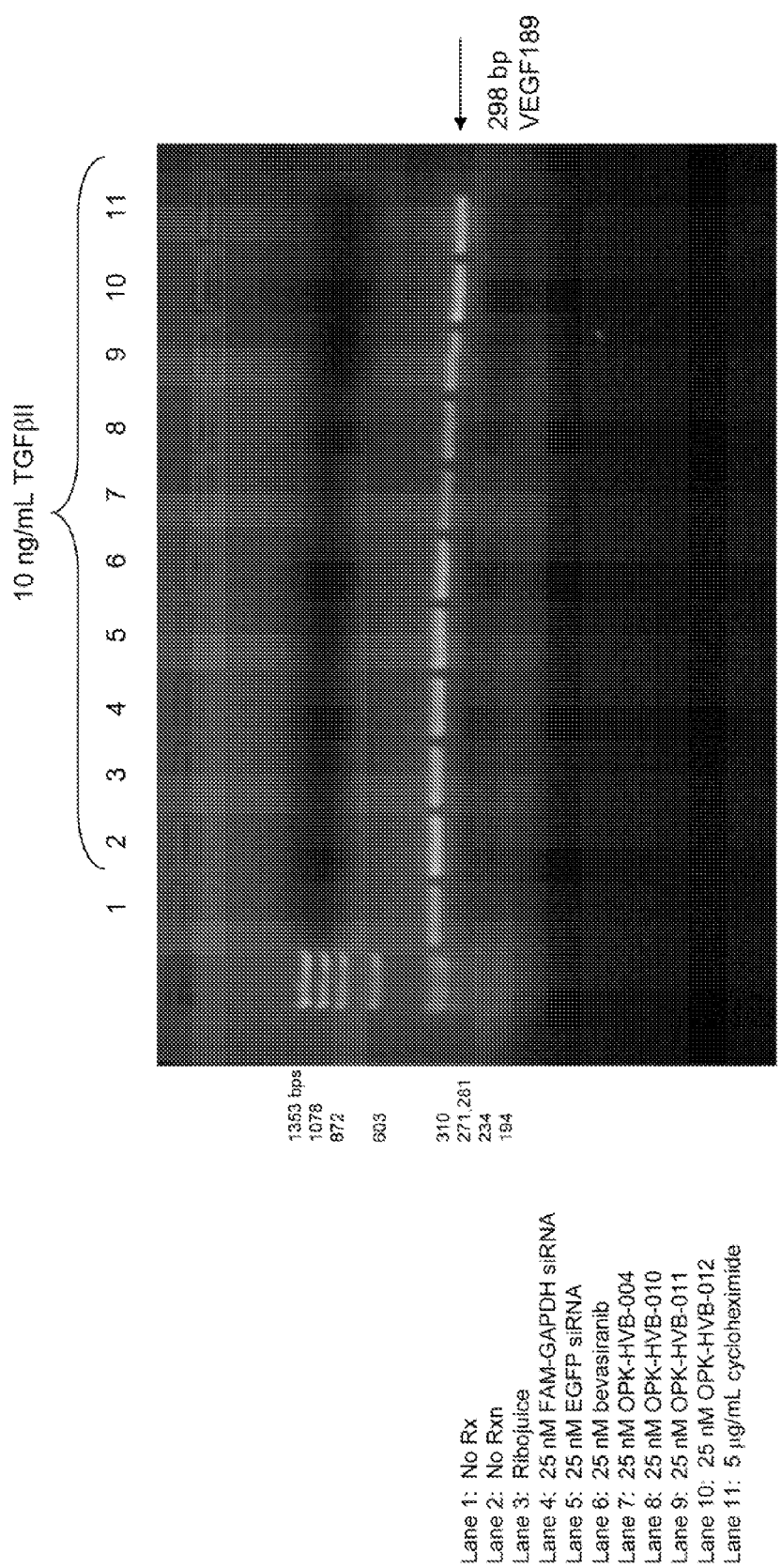
FIG. 20 depicts the effect of siRNA targeting the VEGF exon 7/8 junction on $VEGF_{189}$ mRNA expression using RT-PCR.

VEGF$_{189}$ isoform RT-PCR was also performed as shown in FIG. 20. Samples in Lanes 2-11 were treated with 10 ng/mL TGFβII to upregulate the production of VEGF.

25 nM bevasiranib (lane 6), 25 nM OPK-HVB-004 (lane 7) and 25 nM OPK-HVB-010 (lane 8) downregulated the production of VEGF$_{189}$ mRNA following induction with TGFβII (lane 2) as demonstrated by the bands being lighter than control in lane 3.

Figure 21:
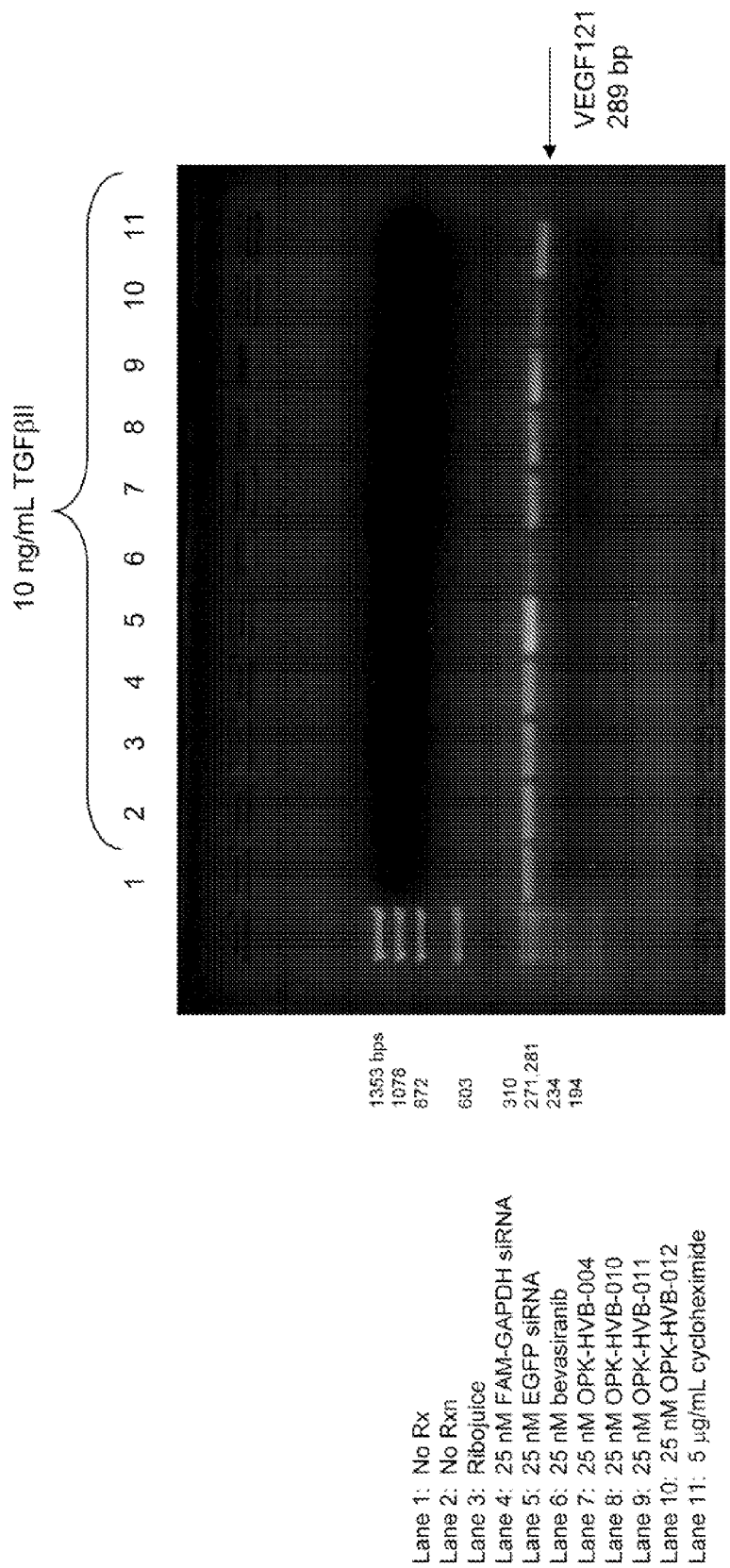
FIG. 21 depicts the effect of siRNA targeting the VEGF exon 7/8 junction on $VEGF_{121}$ mRNA expression using RT-PCR.

VEGF$_{121}$ isoform RT-PCR was then performed as shown in FIG. 21. Samples in Lanes 2-11 were treated with 10 ng/mL TGFβII to upregulate the production of VEGF.

VEGF$_{121}$ mRNA was downregulated in lane 6 (25 nM bevasiranib) as demonstrated by the bands being lighter than control in lane 3.

Figure 22:
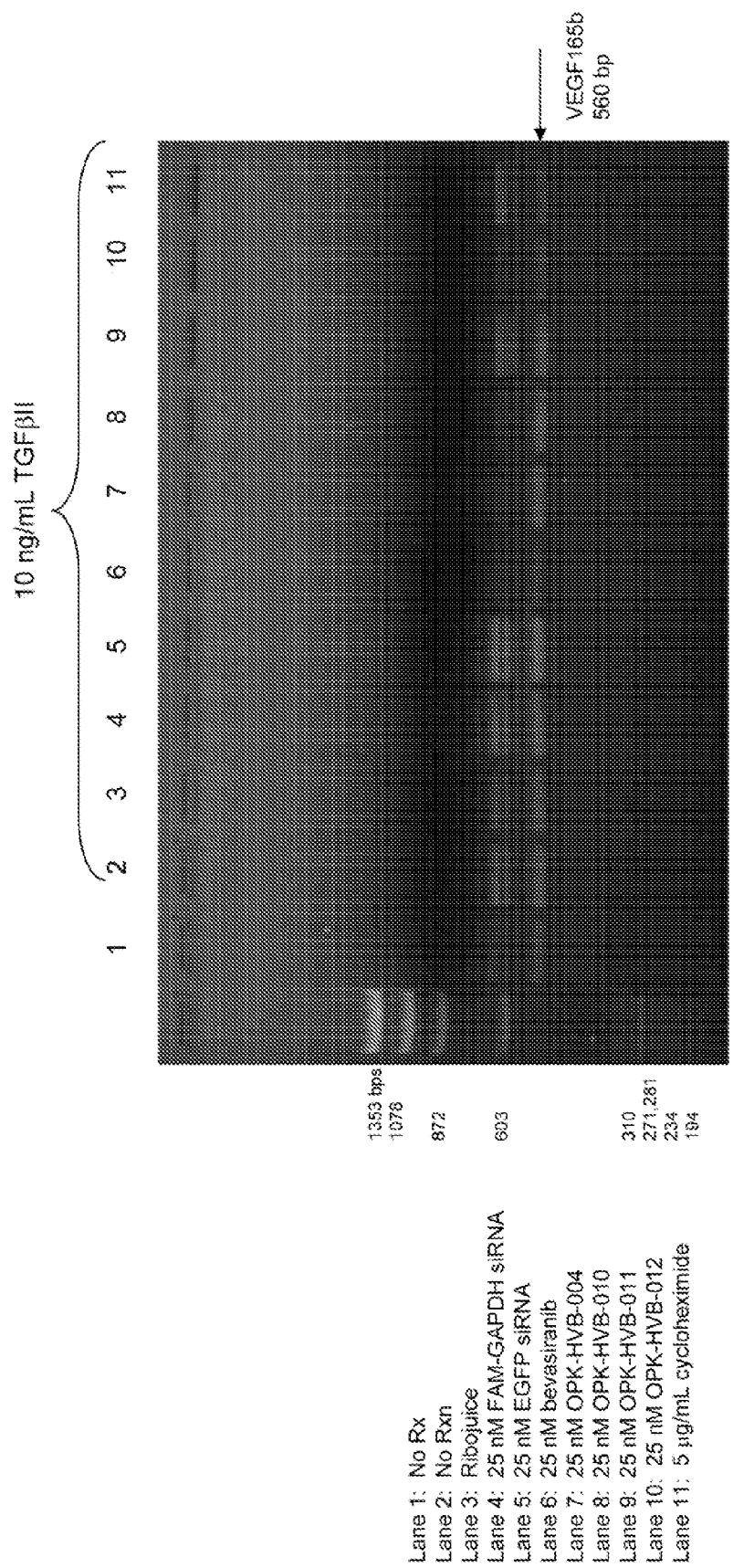
FIG. 22 depicts the effect of siRNA targeting the $VEGF_{165}$ exon 7/8 junction on $VEGF_{165b}$ mRNA expression using RT-PCR. Double banding at about 600 bp is artifactual.

Finally, VEGF$_{165b}$ isoform RTPCR was performed as shown in FIG. 22.

Samples in Lanes 2-11 were treated with 10 ng/mL TGFβII to upregulate the production of VEGF. As an initial matter, the double banding>600 bp was determined to be artifactual. However, VEGF$_{165b}$ mRNA is downregulated by bevasiranib (lane 6) as shown by the bands being fainter that the control of lane 3. In contrast, bands for OPK-HVB-004 (lane 7) and OPK-HVB-010 (lane 8) were not fainter that control in lane 3. Thus, these siRNA constructs preserved VEGF$_{165b}$ expression while also being able to inhibit various other VEGF isoforms. Thus, siRNAs sparing VEGFA$_{165b}$ can be synthesized and may be more efficacious then siRNAs that knockdown all VEGF-A isoforms. VEGF$_{165b}$ sparing siRNAs may be potent therapeutic candidates for the treatment of ocular neovascularization.

Example 13

Cytokine Profile Following Treatment with siRNAs

The cytokine secretion profile of ARPE19 cells following treatment with polyinosinic-polycytidylic acid sodium salt [Poly (I:C)], a dsRNA analogue was determined. Further tests to determined whether or not siRNAs behaved like Poly (I:C) and caused the cells to produce the same cytokines were conducted.

Methods. ARPE19 cells were seeded in 24 well plates (50,000 cells per well). Twenty-four hours later, media was removed and cells were treated with Poly (I:C); 0-1000 mg/mL (Sigma, St. Louis, Mo.) or poly deoxyinosinic-deoxycytidylic acid sodium salt [Poly (dI:dC); 50 mU/mL-800 mU/mL] (Sigma), prepared in serum free DMEM/F12 (1:1) (Invitrogen, Carlsbad, Calif.). Forty-eight hours posttreatment, media was collected from cells and analyzed for IFN-α, IFN-β, IFN-γ, IL-8, IL-6, TNFα, ICAM, IL-12 and MCP-1 via ELISA (Quantikine® Immunoassays for IFNγ, IL-8, IL-6, TNFa, ICAM, IL-12 and MCP-1, R&D Systems, Minneapolis, Minn.); Verikine® ELISA kits for IFN-α and IFN-β, PBL Biomedical Laboratories, Piscataway, N.J.) according to the manufacturers' protocols.

ARPE19 cells were transfected with bevasiranib, OPK-HVB-004, OPK-HVB-009, OPK-HVB-010 and OPK-HVB-012 (Dhamacon/Thermo Scientific, Chicago, Ill.). Cells were seeded in 24 well plates (40,000 cells per well). 24 hours later, cells were transfected with 25 nM siRNA using Ribojuice™ Transfection Reagent (Novagen/EMD. San Diego, Calif.) according to the manufacturer's protocol. 24 hours post transfection, cells were treated with 10 ng/mL human recombinant TGFβII (R&D Systems). 48 hours post-transfection (ie. 24 hours post-TGFbII treatment), media was collected and cytokine levels were analyzed, as described above. Additionally, media was analyzed for hVEGF via ELISA (R&D Systems). Results are shown in FIG. 23.

Conclusions. Based upon the foregoing it is suggested that (ii) ARPE19 cells produce several inflammatory cytokines in response to Poly (I:C), a dsRNA analogue, but do not produce three key mediators, IFN-α, IFN-β or IFN-γ; (ii) ARPE19 cells can be used to study the inflammatory potential and specific effects of dsRNAs such as siRNAs; and (iii) OPK-HVB-009 an OPK-HVB-010 did not cause ARPE19 cells to secrete any of the cytokines tested, suggesting they may have a low inflammatory potential.

Example 14

Dose Response Curves Shows Specificity of siRNAs

Figure 25:
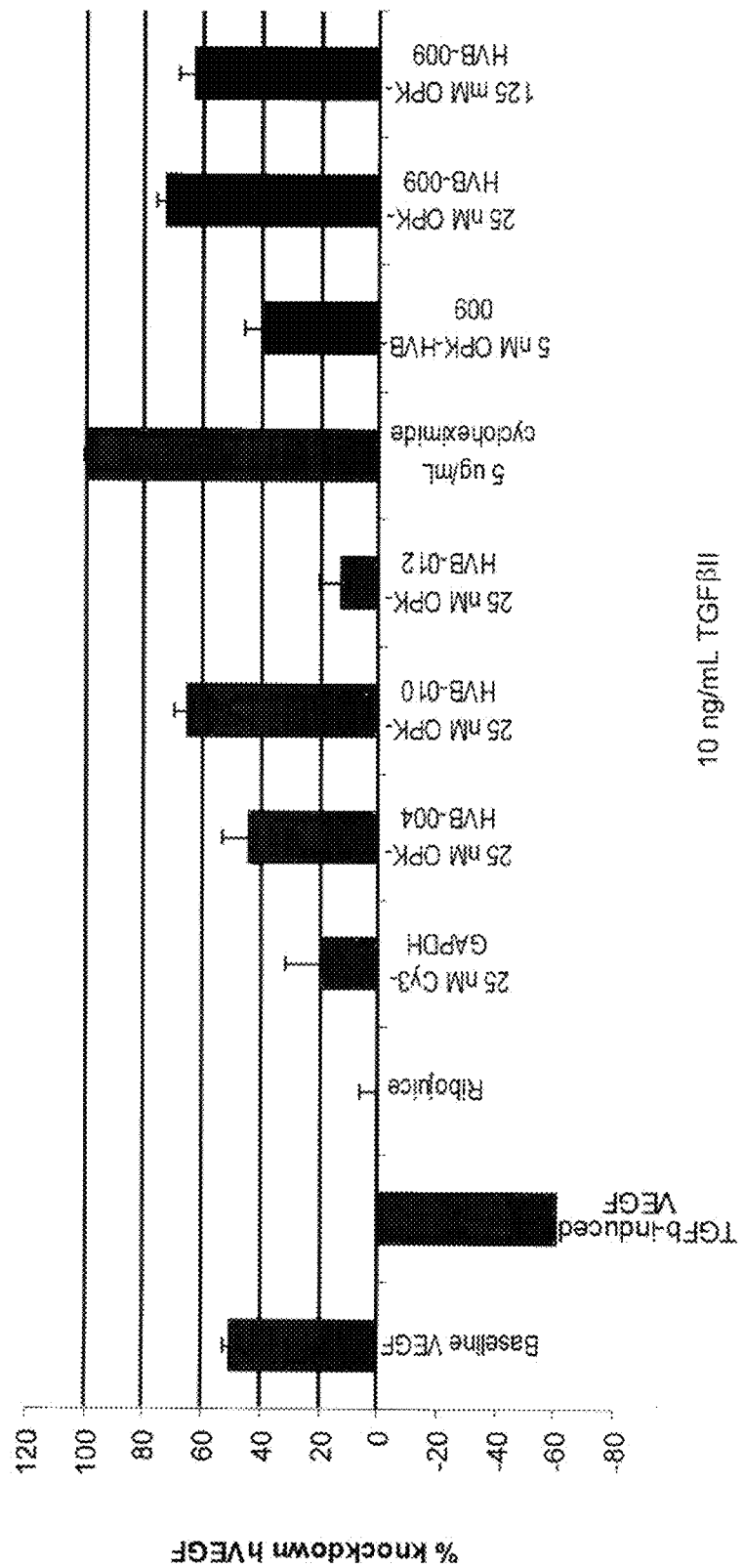
FIG. 25 depicts the effect of siRNAs on total VEGF protein secretion by ARPE19 cells.
Figure 26:
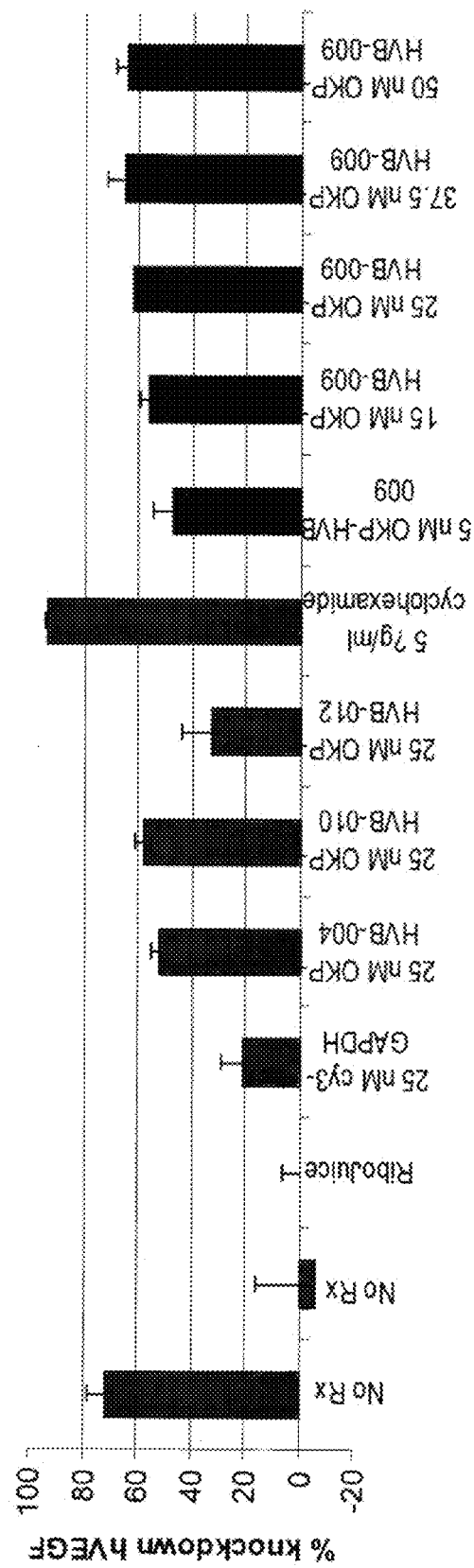
FIG. 26 depicts the effect of siRNAs on total VEGF protein secretion by ARPE19 cells.

A dose response curve was generated using various siRNAs, 21-mers, as shown in FIGS. 26 and 27. A dose response was seen with certain siRNAS indicating a specific response to the siRNAs used. A dose response curve was also generated for OPK-HVB-009 as shown in FIGS. 25 and 26. The cells were treated and transfected as described in Examples 12 and 13. Cells were seeded in 24 well plates (40,000 cells/well). Additionally, different concentrations were used, and therefore, the volumes of OPTI-MEM, Ribojuice, and siRNA were adjusted accordingly when preparing the 50 µtransfection mix.

Example 15

Stability of siRNAs

ARPE19 cells were transfected with siRNAs that had been stored under various conditions as shown in FIGS. 28, 29, 30 31, and 32. The cells were transfected as described in Examples 12 and 13. It was found that the siRNA molecules were stable under various conditions as shown in FIGS. 28, 29, 30, 31, and 32. For example, 7.5 µM siRNA was aliquoted into 3 tubes and each tube was stored at a different temperature (37° C., room temperature, 4° C.) for up to 8 weeks. Aliquots of each tube were collected at predetermined time points (24 hrs, 48 hrs and then weekly). Upon collection aliquots were stored at −80° C. Each aliquot was subsequently tested for efficacy in ARPE19 cells to see if the siRNAs maintained their stability under the different environmental conditions. siRNAs were transfected into ARPE19 cells using the methods described in Example 12 where 40,000 cells were seeded per well.

Example 16

Cross-Species Down Regulation of VEGF

C6 cells were seeded in 24 well plates (P12, 40,000 cells per well). Eighteen to twenty-four hours post-seeding, cells were 50-70% confluent and used for transfection. Cells were transfected with OPK-HVB-004, OPK-HVB-009, OPK-HVB-010 and OPK-HVB-012 using the Ribojuice™ siRNA Transfection Reagent (Novagen) following the manufacturer's protocol. Briefly, for a single well serum-free OPTI-MEM (40.5 µL-47 µL) was pipetted into an eppendorf tube and then 2 µL of Ribojuice were added to the OPTI-MEM (Gibco). The solution was mixed by gentle vortexing and centrifuged briefly to collect the contents at the bottom of the tube and incubated at room temperature for 5 min. siRNA (0.3 µL-7.5 µL of a 100 nM or 1 µM stock) was added to the Ribojuice/medium mix and gently mixed and briefly centrifuged to collect contents at the bottom of the tube. The mixture was incubated at room temperature for 15 minutes. During the incubation, media was removed from cells and replaced with 250 µL of fresh C6 growth media (F-12 Kaighn's, 2.5% fetal calf serum; 15% horse serum, 1% penicillin/streptomycin). After the 15 min incubation, the siRNA/Ribojuice/medium mixture (50 µL) was added dropwise to the cells. The plate was gently rocked to ensure the complexes were evenly dispersed throughout the well. The Final concentration of siRNA in the 300 µL volume was 250 pM, 500 pM, 1 nM, 5 nM or 25 nM. Cells were maintained at 37° C., 5% $CO_2$ for 24 hours. All volumes were scaled up such that each siRNA was tested at each concentration in triplicate. 24 hours post-transfection, the transfection mixture was removed and cells were treated with 500 µLs of fresh C6 growth media or with fresh C6 growth media supplemented with 10 ng/mL human recombinant TGFβII. The cells were returned to 37° C., 5% $CO_2$ for an additional 24 hours. Afterwards the media was removed from the cells and analyzed for protein expression by ELISA (Quantikine rat VEGF ELISA kit, R&D Systems).

NIH3T3 cells were seeded in 24 well plates (P2-P6, 40,000 cells per well). Eighteen to twenty-four hours post-seeding, cells were 50-70% confluent and used for transfection. Cells were transfected with siRNAs using Lipofectamine™ Reagent 2000 (Invitrogen) following the manufacturer's protocol. Briefly for a single well, siRNA (1 µM or 7.5 µM) was diluted in 50 µL OPTI-MEM in an eppendorf tube and gently mixed and vortexed. In a second eppendorf tube 1 µL of Lipofectamine 2000 was combined with 49 µL of OPTI-MEM. The mixture was gently mixed and vortexed and incubated for 5 minutes at room temperature. After the 5 minutes, the diluted siRNA (50 µL volume) was added to the diluted Lipofectamine 2000 (50 µL). The contents were mixed gently and incubated at room temperature for 20 minutes. During the 20 minute incubation, media was removed from the cells and replaced with 500 µLs of fresh NIH3T3 growth media (DMEM, 10% fetal calf serum). After the 20 minutes the siRNA-Lipofectamine 2000 complex (100 µL) was added dropwise to the cells. The plate was gently rocked to ensure the complexes were evenly dispersed throughout the well. The cells were then incubated at 37° C., 5% $CO_2$ for 24 hours. The final concentration of siRNA in the 500 µL volume was 1 nM, 5 nM or 25 nM. 24 hours post-transfection, the transfection mixture was removed and cells were treated with 500 µLs of fresh DMEM or with fresh DMEM supplemented with 10 ng/mL human recombinant TGFβII. The cells were returned to 37° C., 5% CO, for an additional 24 hours. Afterwards the media was removed from the cells and analyzed for protein expression by ELISA (Quantikine mouse VEGF ELISA kit, R&D Systems).

Figure 34:
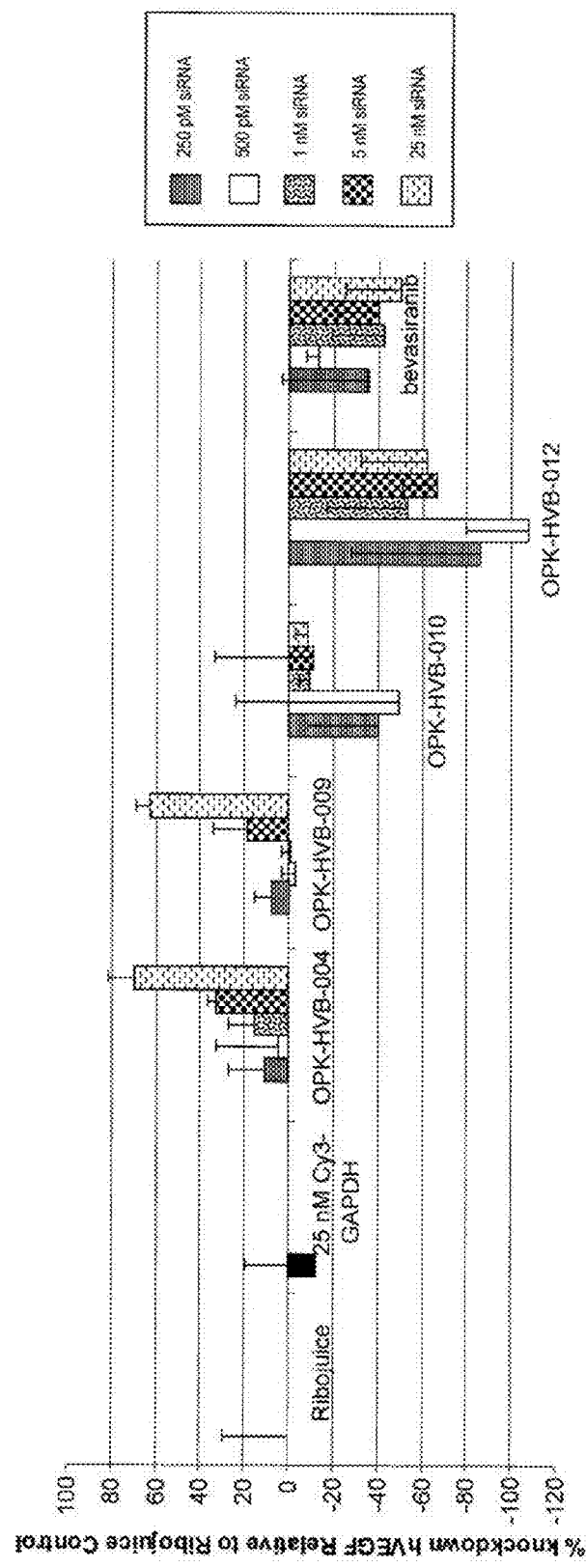
FIG. 34 depicts the effect of siRNAs on rat VEGF secretion by C6 cells.
Figure 35:
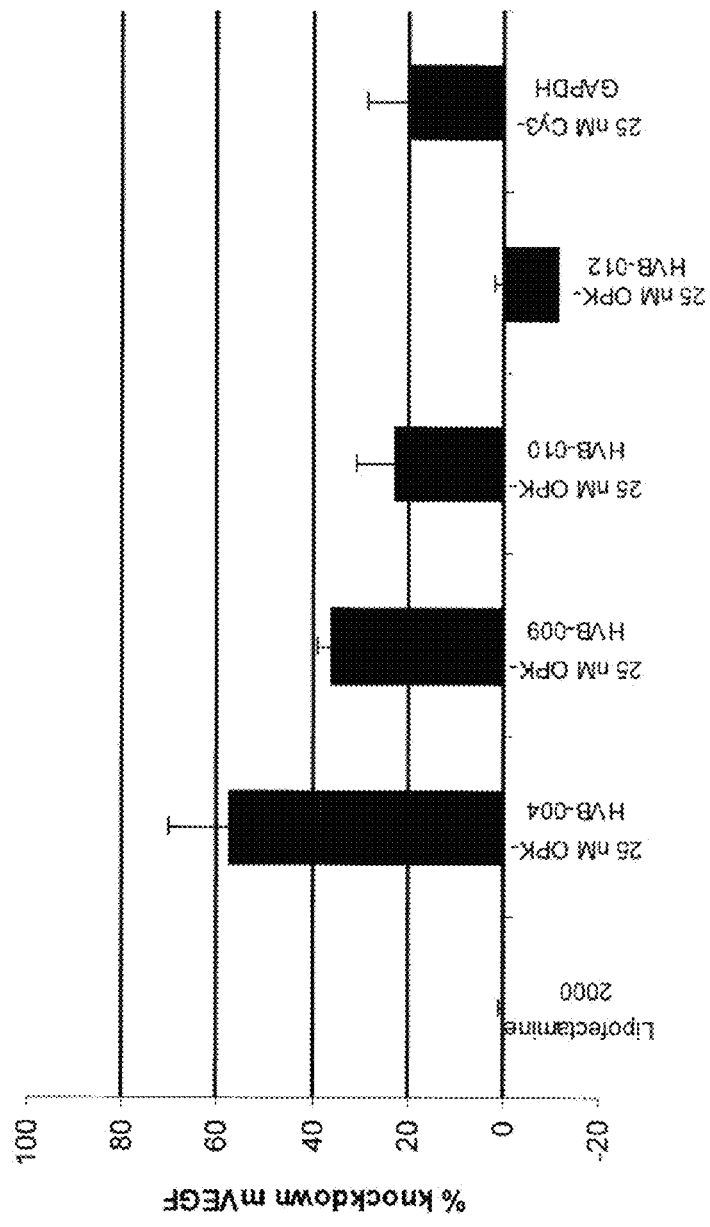
FIG. 35 depicts the effect of siRNAs on mouse VEGF secretion by NIH3T3 cells.

Results of the experiments are shown in FIGS. 34, 35 and 39. OPK-HVB-004 and OPK-HVB-009 were able to inhibit VEGF secretion by C6 cells as shown in FIG. 34. Similar experiments were done in mouse cells (NIH3T3) and OPK-HVB-004, OPK-HVB-009, and OPK-HVB-010 were able to inhibit secretion of mouse VEGF as shown in FIGS. 35 and 39.

Example 17

Figure 36:
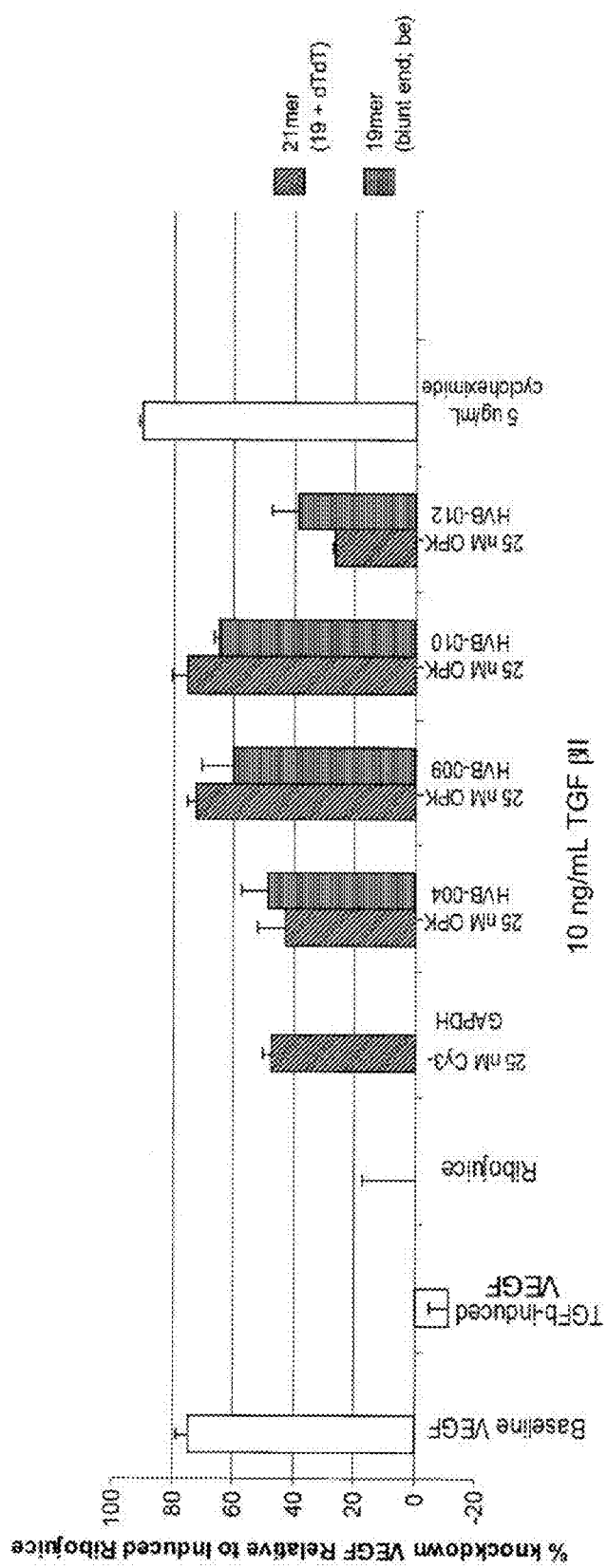
FIG. 36 depicts the effect of siRNAs on VEGF secretion by ARPE19 cells.

Comparison of Different siRNAs 21 mer siRNAs comprising an overhang were compared to a 19 mer blunt-end counterpart. ARPE19 cells were transfected with the different siRNAs as described in Examples 12, 13, and 14 and VEGF production was measured. The Blunt end counterpart was found to knockdown VEGF production in ARPE19 cells equally effective as the 21 mer as shown in FIG. 36.

Example 18

Figure 37:
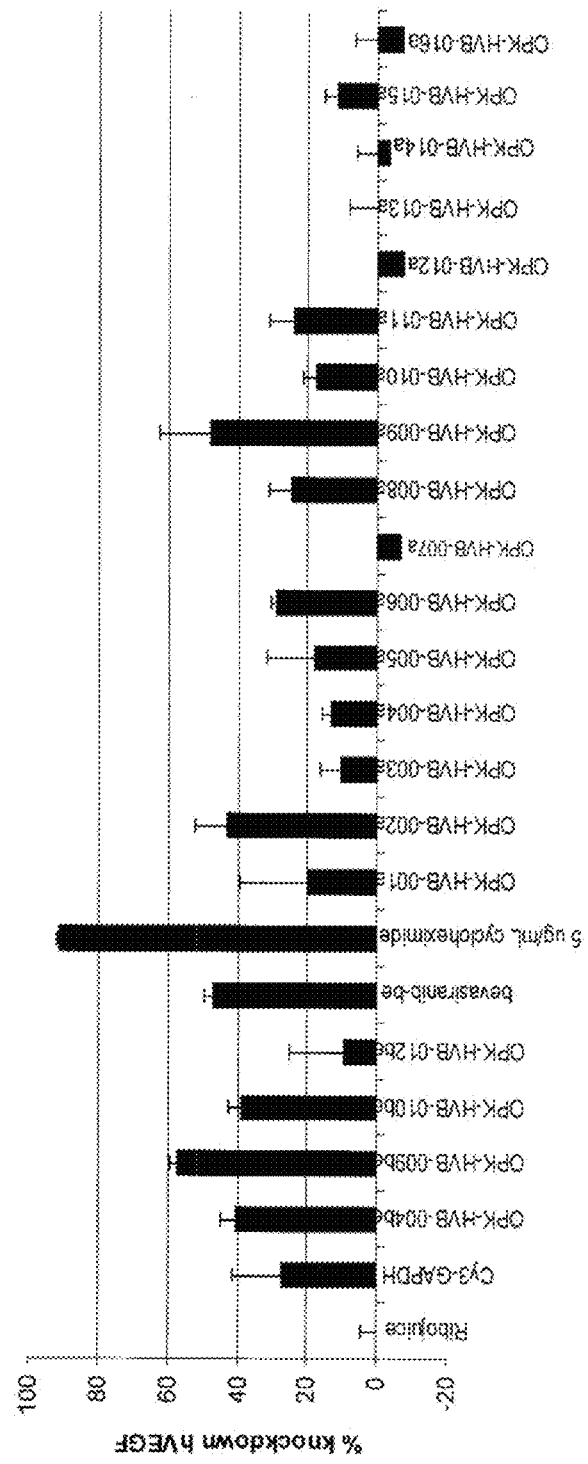
FIG. 37 depicts the effect of siRNAs on VEGF secretion by ARPE19 cells.

Screen of 19 mers Comprising 17 bp and an Overhang can Inhibit VEGF Production siRNAS comprising a 17 mer and a dTdT overhang were transfected in ARPE19 cells as described in Examples 12, 13, and 14. Several siRNAs were found to inhibit VEGF production as shown in FIG. 37.

Example 19

Figure 38:
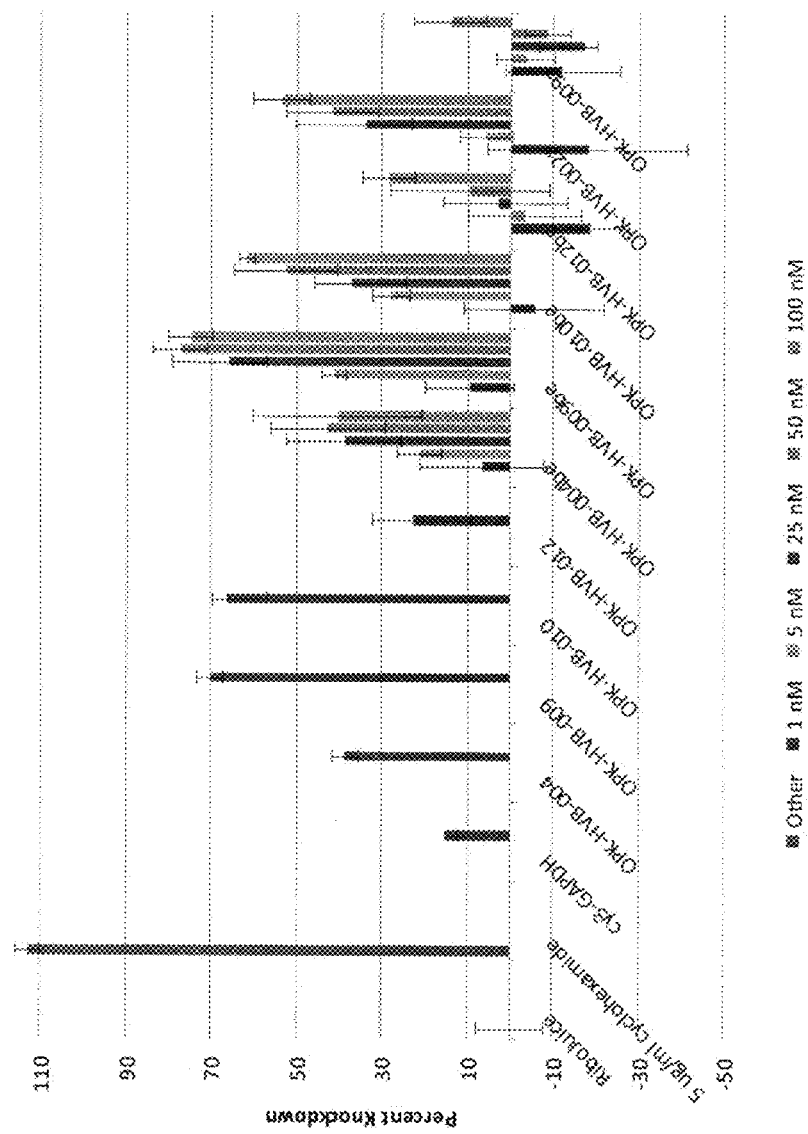
FIG. 38 depicts the effect of siRNAs on VEGF secretion by ARPE19 cells.

Dose Response of siRNAs mers comprising a blunt end or an overhang 19 mer (17 bp+dTdT over) were transfected into ARPE19 cells at various doses as shown in FIG. 38. A dose response curve was generated by measuring VEGF secretion as described in Examples 12, 13 and 16. The dose response seen indicates that the response to the siRNAs is specific to the siRNA and not generated by a non-specific siRNA response. The results can be seen in FIG. 38. Blunt end siRNAs tested in NIH3T3 cells showed a specific dose response. (See FIG. 39).

The invention claimed is:

1. An isolated siRNA comprising of a duplex of a first RNA strand and a second RNA strand, said first RNA strand comprising a nucleotide sequence identical to a target sequence of a vascular endothelial growth factor (VEGF) isoform $VEGF_{189}$, further wherein said siRNA is non-complementary to $VEGF_{165b}$, wherein the nucleotide sequence identical to a target sequence consists of a sequence selected from the group consisting of SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO 99, SEQ ID NO 100, SEQ ID NO 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, and SEQ ID NO: 118.

2. The siRNA of claim 1, wherein the first and second RNA strands forming the RNA duplex are covalently linked by a single-stranded hairpin.

3. The siRNA of claim 1, wherein the siRNA further comprises non-nucleotide material.

4. The siRNA of claim 1, wherein the first and second RNA strands are stabilized against nuclease degradation.

5. The siRNA of claim 1, further comprising a 3' overhang.

6. The siRNA of claim 5, wherein the 3' overhang comprises from 1 to about 6 nucleotides.

7. The siRNA of claim 5, wherein the 3' overhang comprises about 2 nucleotides.

8. The siRNA of claim 1, wherein the sense RNA strand comprises a first 3' overhang, and the antisense RNA strand comprises a second 3' overhang.

9. The siRNA of claim 8, wherein the first and second 3' overhangs each comprise from 1 to about 6 nucleotides.

10. The siRNA of claim 8, wherein the first 3' overhang comprises a dinucleotide and the second 3' overhang comprises a dinucleotide.

11. The siRNA of claim 10, where the dinucleotide comprising the first and second 3' overhangs is dithymidylic acid (tt) or diuridylic acid (uu).

12. The siRNA of claim 5, wherein the 3' overhang is stabilized against nuclease degradation.

13. The siRNA of claim 1, wherein said siRNA comprises at least one blunt end.

14. The siRNA of claim 1, wherein said siRNA can inhibit the production or secretion of VEGF from a human cell and a rat cell.

15. The siRNA of claim 1, wherein said siRNA can inhibit the production or secretion of VEGF from a human cell, a mouse cell, and a rat cell.

16. An isolated siRNA comprising of a duplex of a first RNA strand and a second RNA strand, said first RNA strand comprising a nucleotide sequence identical to a target sequence of a vascular endothelial growth factor (VEGF) isoform $VEGF_{189}$, further wherein said siRNA is non-complementary to $VEGF_{165b}$, wherein the nucleotide sequence identical to a target sequence consists of a sequence selected from the group consisting of SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO 99, SEQ ID NO 100, SEQ ID NO 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, and SEQ ID NO: 118, wherein the siRNA does not function to silence $VEGF_{165b}$ or form a RISC complex with $VEGF_{165b}$.

17. A pharmaceutical composition comprising a siRNA and a pharmaceutically acceptable carrier, said siRNA comprised of a duplex of a first RNA strand a second RNA strand, said first RNA strand comprising a nucleotide sequence identical to a target sequence of a vascular endothelial growth factor (VEGF) isoform $VEGF_{189}$, further wherein said siRNA is non-complementary to $VEGF_{165b}$, wherein the nucleotide sequence identical to a target sequence consists of a sequence selected from the group consisting of SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO 99, SEQ ID NO 100, SEQ ID NO 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, and SEQ ID NO: 118.

18. The pharmaceutical composition of claim 17, wherein the first and second RNA strands are stabilized against nuclease degradation.

19. The pharmaceutical composition of claim 17, further comprising at least one 3' overhang.

20. The pharmaceutical composition of claim 19, wherein the at least one 3' overhang comprises about 2 nucleotides.

21. The pharmaceutical composition of claim 19, where the at least one 3' overhang comprises a dithymidylic acid (tt) or diuridylic acid (uu).

22. The pharmaceutical composition of claim 17, wherein the sense RNA strand comprises a first 3' overhang, and the antisense RNA strand comprises a second 3' overhang.

23. The pharmaceutical composition of claim 17, wherein siRNA comprises at least one blunt end.

24. The siRNA of claim 17, wherein said siRNA can inhibit the production or secretion of VEGF from a human cell and a rat cell.

25. The siRNA of claim 17, wherein said siRNA can inhibit the production or secretion of VEGF from a human cell, a mouse cell, and a rat cell.

26. A method of treating an angiogenic disease in a subject comprising administering to the subject an effective amount of a pharmaceutical composition comprising the isolated siRNA of claim 1 and a pharmaceutically acceptable carrier.

27. The method of claim 26, wherein the angiogenic disease comprises a tumor associated with a cancer.

28. The method of claim 27, wherein the cancer is selected from the group consisting of breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, wilm's tumor, multiple myeloma, skin cancer, lymphoma, and blood cancer.

29. The method of claim 26, wherein the angiogenic disease is selected from the group consisting of diabetic retinopathy, age-related macular degeneration, and inflammatory diseases.

30. The method of claim 29, wherein the inflammatory disease is psoriasis or rheumatoid arthritis.

31. The method of claim 29, wherein the angiogenic disease is age-related macular degeneration.

32. The method of claim 26, wherein the pharmaceutical composition is administered in combination with a pharmaceutical agent for treating the angiogenic disease, which pharmaceutical agent is different from the short interfering ribonucleic acid (siRNA).

33. The method of claim 32, wherein the angiogenic disease is cancer, and the pharmaceutical agent comprises a chemotherapeutic agent.

34. The method of claim 33, wherein the chemotherapeutic agent is selected from the group consisting of cisplatin, carboplatin, cyclophosphamide, 5-fluorouracil, adriamycin, daunorubicin, and tamoxifen.

35. The method of claim 26, wherein the pharmaceutical composition is administered to a subject in combination with another therapeutic method designed to treat the angiogenic disease.

36. The method of claim 35, wherein the angiogenic disease is cancer, and the pharmaceutical composition is administered in combination with radiation therapy, chemotherapy or surgery.

37. A method for inhibiting expression of human vascular endothelial growth factor (VEGF) comprising administering to a subject an effective amount of a pharmaceutical composition comprising the isolated siRNA of claim 1 and a pharmaceutically acceptable carrier.

38. The method of claim 37, wherein the effective amount comprises from about 1 nm to about 100 nm of the short interfering ribonucleic acid (siRNA).

39. The method of claim 37, wherein the pharmaceutical composition further comprises a delivery reagent.

40. The method of claim 37, wherein the delivery agent is selected from the group consisting of lipofectin, lipofectamine, cellfectin, polycations, and liposomes.

41. The method of claim 40, wherein the delivery agent is a liposome.

42. The method of claim 41, wherein the liposome comprises a ligand which targets the liposome to cells at or near the site of angiogenesis.

43. The method of claim 42, wherein the ligand binds to receptors on tumor cells or vascular endothelial cells.

44. The method of claim 42, wherein the ligand comprises a monoclonal antibody.

45. The method of claim 41, wherein the liposome is modified with an opsonization-inhibition moiety.

46. The method of claim 45, wherein the opsonization-inhibiting moiety comprises a PEG, PPG, or derivatives thereof.

47. The method of claim 37, wherein the short interfering ribonucleic acid (siRNA) is expressed from a recombinant plasmid.

48. The method of claim 37, wherein the short interfering ribonucleic acid (siRNA) is expressed from a recombinant viral vector.

49. The method of claim 48, wherein the recombinant viral vector comprises an adenoviral vector, an adeno-associated viral vector, a lentiviral vector, a retroviral vector, or a herpes virus vector.

50. The method of claim 49, wherein the recombinant viral vector is pseudotyped with surface proteins from vesicular stomatitis virus, rabies virus, Ebola virus, or Mokola virus.

51. The method of claim 48, wherein the recombinant viral vector comprises an adeno-associated viral vector.

52. The method of claim 37, wherein the pharmaceutical composition is administered by an enteral administration route.

53. The method of claim 52, wherein the enteral administration route is selected from the group consisting of oral, rectal, and intranasal.

54. The method of claim 37, wherein the pharmaceutical composition is administered by a parenteral administration route.

55. The method of claim 54, wherein the parenteral administration route is selected from the group consisting of intravascular administration, peri- and intra-tissue injection, subcutaneous injection or deposition, subcutaneous infusion, and direct application at or near the site of neovascularization.

56. The method of claim 55, wherein the intravascular administration is selected from the group consisting of intravenous bolus injection, intravenous infusion, intra-arterial bolus injection, intra-arterial infusion and catheter instillation into the vasculature.

57. The isolated siRNA of claim 1, wherein the siRNA does not silence $VEGF_{165b}$ or form a RISC complex with $VEGF_{165b}$.

58. The pharmaceutical composition of claim 17, wherein the siRNA does not silence $VEGF_{165b}$ or form a RISC complex with $VEGF_{165b}$.

* * * * *